(12) United States Patent
Suzuki et al.

(10) Patent No.: US 10,004,739 B2
(45) Date of Patent: Jun. 26, 2018

(54) METHODS FOR TREATING CANCER BY INHIBITING FGFR3/TACC3 FUSION PROTEIN

(71) Applicant: Astellas Pharma Inc., Chuo-ku, Tokyo (JP)

(72) Inventors: Atsushi Suzuki, Tokyo (JP); Makoto Asaumi, Tokyo (JP); Kazuhisa Tsunoyama, Tokyo (JP); Kouichi Nishimura, Tokyo (JP); Akifumi Morinaka, Tokyo (JP); Tomohiro Yamauchi, Tokyo (JP); Masayasu Yoshino, Tokyo (JP); Hiroaki Yoshizaki, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days. days.

(21) Appl. No.: 15/264,900

(22) Filed: Sep. 14, 2016

(65) Prior Publication Data
US 2016/0375023 A1 Dec. 29, 2016

Related U.S. Application Data

(62) Division of application No. 14/383,199, filed as application No. PCT/JP2013/056225 on Mar. 7, 2013, now Pat. No. 9,481,911.

(30) Foreign Application Priority Data

Mar. 8, 2012 (JP) .................................. 2012-052147
Sep. 5, 2012 (JP) .................................. 2012-195451
Dec. 21, 2012 (JP) .................................. 2012-280325

(51) Int. Cl.
| | |
|---|---|
| A61K 31/506 | (2006.01) |
| G01N 33/574 | (2006.01) |
| G01N 33/74 | (2006.01) |
| C12Q 1/68 | (2018.01) |
| A61K 31/4439 | (2006.01) |
| A61K 31/496 | (2006.01) |
| C07K 14/71 | (2006.01) |
| C07K 14/47 | (2006.01) |
| C12Q 1/6886 | (2018.01) |

(52) U.S. Cl.
CPC ........ *A61K 31/506* (2013.01); *A61K 31/4439* (2013.01); *A61K 31/496* (2013.01); *C07K 14/47* (2013.01); *C07K 14/71* (2013.01); *C12Q 1/6886* (2013.01); *G01N 33/57407* (2013.01); *G01N 33/57423* (2013.01); *G01N 33/74* (2013.01); *C07K 2319/00* (2013.01); *C12Q 2600/118* (2013.01); *C12Q 2600/156* (2013.01); *C12Q 2600/158* (2013.01); *G01N 2333/50* (2013.01)

(58) Field of Classification Search
CPC .............. A61K 31/4439; A61K 31/496; A61K 31/506; C07K 14/47; C07K 14/71; C07K 2319/00; C12Q 1/6886; C12Q 2600/118; C12Q 2600/156; C12Q 2600/158; G01N 33/57407; G01N 33/57423; G01N 33/74; G01N 2333/50
See application file for complete search history.

(56) References Cited

FOREIGN PATENT DOCUMENTS

| | | |
|---|---|---|
| CN | 1976706 A | 6/2007 |
| EP | 2821402 A1 | 1/2015 |
| WO | WO 2005/047244 A2 | 5/2005 |
| WO | WO 2013/089882 A2 | 6/2013 |
| WO | WO 2014/018673 A2 | 1/2014 |
| WO | WO 2014/051022 A1 | 4/2014 |
| WO | WO 2014/071419 A2 | 5/2014 |

OTHER PUBLICATIONS

Costa R, et al. Oncotarget. 7:55924-55938. 2016. Available online at—doi.org/10.18632/oncotarget.10482).*
https://clinicaltrials.gov/ (Trial No. NCT01457846; Oct. 24, 2011).*
https://clinicaltrials.gov/ (Trial No. NCT01213160; Oct. 1, 2010).*
https://clinicaltrials.gov/ (Trial No. NCT01004224); Dec. 11, 2001).*
https://clinicaltrials.gov/ (Trial No. NCT00958971; Aug. 11, 2009).*
https://clinicaltrials.gov/ (Trial No. NCT01379534; Jun. 23, 2011).*
https://clinicaltrials.gov/ (Trial No. NCT00790426; Nov. 13, 2008).*
Office Action dated Nov. 8, 2016, in corresponding Japanese patent application No. 2014-503528, with English translation.
Avet-Loiseau et al., "High Incidence of Translocations t(11;14)(q13;q32) and t(4;14)(p16;q32) in Patients with Plasma Cell Malignancies," Cancer Research, Dec. 15, 1988, 58(24):5640-5645.
Govindan, Ramaswamy M.D., "Summary of Presentation from the Targeted Therapy in Lung Cancer Meeting," Journal of Thoracic Oncology, Nov. 2011, 6(11,Supp4):S1757-S1785.
Greulich et al., "Targeting mutant fibroblast growth factor receptors in cancer," Trends in Molecular Medicine, May 2011, 17(5):283-292.

(Continued)

*Primary Examiner* — Robert S Landsman
(74) *Attorney, Agent, or Firm* — Foley & Lardner LLP

(57) ABSTRACT

The present invention aims to elucidate a polynucleotide as a novel responsible gene for cancer and aims to thus provide a method for detecting the polynucleotide and a polypeptide encoded by the polynucleotide and a detection kit, a probe set, and a primer set for the detection. The present invention also aims to provide a pharmaceutical composition for treating cancer. The method detects a fusion gene composed of a portion of an FGFR3 gene and a portion of a TACC3 gene or a fusion protein encoded by the fusion gene. The primer set, the probe set, or the detection kit comprises a sense primer and a probe set designed from the portion encoding FGFR3 and an antisense primer and a probe set designed from the portion encoding TACC3. Since an inhibitor of the polypeptide exhibits antitumor effect, a pharmaceutical composition for treating cancer which is positive for either the fusion gene or the polypeptide is provided.

10 Claims, No Drawings

(56) References Cited

OTHER PUBLICATIONS

Jarvius et al., "In situ Detection of Phosphorylated Platelet-derived Growth Factor Receptor Beta Using a Generalized Proximity Ligation Method," Molecular & Cellular Proteomics, 2007, 6(9):1500-1509.

Nilsson et al., "VEGF receptor 2/-3 heterodimers detected in situ by proximity ligation on angiogenic sprouts," The EMBO Journal, 2010, 29(8):1377-1388.

Parker et al., "The tumorigenic FGFR3-TACC3 gene fusion escapes miR-99a regulation in glioblastoma," The Journal of Clinical Investigation, Feb. 1, 2013, 123(2)855-865.

Singh et al., "Transforming Fusions of FGFR and TACC Genes in Human Glioblastoma," Science, Sep. 7, 2012, epub Jul. 26, 2012, 337(6099):1231-1235.

Soederberg et al., "Characterizing proteins and their interactions in cells and tissues using the in situ proximity ligation assay," Methods, 2008, 45(3):227-232.

Williams et al., "Oncogenic FGFR3 gene fusions in bladder cancer," Human Molecular Genetics, Feb. 15, 2013, epub Nov. 21, 2012, 22(4):795-803.

Yagasaki et al., "Fusion of ETV6 to Fibroblast Growth Factor Receptor 3 in Peripheral T-Cell Lymphoma with a t(4;12)(p16;p13) Chromosomal Translocation," Cancer Research, Dec. 1, 2001, 61(23):8371-8374.

Zhao et al., "A Novel, Selective Inhibitor of Fibroblast Growth Factor Receptors That Shows a Potent Broad Spectrum of Antitumor Activity in Several Tumor Xenograft Models," Mol. Cancer Ther., 2011, 10(11):2200-2210.

Office Action dated Nov. 4, 2015, in corresponding Chinese application No. 201380012774.X, with English translation.

Office Action dated May 5, 2016, in corresponding Eurasian patent application No. 201491655, with English translation.

Office Action dated Jul. 15, 2016, in corresponding Chinese application No. 201380012774.X, with English translation.

Office Action dated Feb. 4, 2017, in Chinese Application No. 201380012774.X, with English translation.

Office Action dated Oct. 12, 2017, in EP 13757006.5.

Office Action dated Aug. 29, 2017, in Chinese Application No. 201380012774.X, with English translation.

\* cited by examiner

SEQUENCE LISTING

```
<160> NUMBER OF SEQ ID NOS: 28

<210> SEQ ID NO 1
<211> LENGTH: 2856
<212> TYPE: DNA
<213> ORGANISM: Homo sapiens
<220> FEATURE:
<221> NAME/KEY: CDS
<222> LOCATION: (1)..(2856)

<400> SEQUENCE: 1 atg ggc gcc cct gcc tgc gcc ctc gcg ctc tgc gtg gcc gtg gcc atc        48
Met Gly Ala Pro Ala Cys Ala Leu Ala Leu Cys Val Ala Val Ala Ile
1               5                   10                  15 gtg gcc ggc gcc tcc tcg gag tcc ttg ggg acg gag cag cgc gtc gtg        96
Val Ala Gly Ala Ser Ser Glu Ser Leu Gly Thr Glu Gln Arg Val Val
            20                  25                  30 ggg cga gcg gca gaa gtc ccg ggc cca gag ccc ggc cag cag gag cag       144
Gly Arg Ala Ala Glu Val Pro Gly Pro Glu Pro Gly Gln Gln Glu Gln
```

-continued

|  |  |  |  |  |  |  |  |  |  |  |  |  |  |  |  |
|---|---|---|---|---|---|---|---|---|---|---|---|---|---|---|---|
|  | 35 |  |  |  | 40 |  |  |  | 45 |  |  |  |  |  |  |

```
ttg gtc ttc ggc agc ggg gat gct gtg gag ctg agc tgt ccc ccg ccc       192
Leu Val Phe Gly Ser Gly Asp Ala Val Glu Leu Ser Cys Pro Pro Pro
    50                  55                  60 ggg ggt ggt ccc atg ggg ccc act gtc tgg gtc aag gat gga aca ggg       240
Gly Gly Gly Pro Met Gly Pro Thr Val Trp Val Lys Asp Gly Thr Gly
65                  70                  75                  80 ctg gtg ccc tcg gag cgt gtc ctg gtg ggg ccc cag cgg ctg cag gtg       288
Leu Val Pro Ser Glu Arg Val Leu Val Gly Pro Gln Arg Leu Gln Val
                85                  90                  95 ctg aat gcc tcc cac gag gac tcc ggg gcc tac agc tgc cgg cag cgg       336
Leu Asn Ala Ser His Glu Asp Ser Gly Ala Tyr Ser Cys Arg Gln Arg
            100                 105                 110 ctc acg cag cgc gta ctg tgc cac ttc agt gtg cgg gtg aca gac gct       384
Leu Thr Gln Arg Val Leu Cys His Phe Ser Val Arg Val Thr Asp Ala
        115                 120                 125 cca tcc tcg gga gat gac gaa gac ggg gag gac gag gct gag gac aca       432
Pro Ser Ser Gly Asp Asp Glu Asp Gly Glu Asp Glu Ala Glu Asp Thr
    130                 135                 140 ggt gtg gac aca ggg gcc cct tac tgg aca cgg ccc gag cgg atg gac       480
Gly Val Asp Thr Gly Ala Pro Tyr Trp Thr Arg Pro Glu Arg Met Asp
145                 150                 155                 160 aag aag ctg ctg gcc gtg ccg gcc gcc aac acc gtc cgc ttc cgc tgc       528
Lys Lys Leu Leu Ala Val Pro Ala Ala Asn Thr Val Arg Phe Arg Cys
                165                 170                 175 cca gcc gct ggc aac ccc act ccc tcc atc tcc tgg ctg aag aac ggc       576
Pro Ala Ala Gly Asn Pro Thr Pro Ser Ile Ser Trp Leu Lys Asn Gly
            180                 185                 190 agg gag ttc cgc ggc gag cac cgc att gga ggc atc aag ctg cgg cat       624
Arg Glu Phe Arg Gly Glu His Arg Ile Gly Gly Ile Lys Leu Arg His
        195                 200                 205 cag cag tgg agc ctg gtc atg gaa agc gtg gtg ccc tcg gac cgc ggc       672
Gln Gln Trp Ser Leu Val Met Glu Ser Val Val Pro Ser Asp Arg Gly
    210                 215                 220 aac tac acc tgc gtc gtg gag aac aag ttt ggc agc atc cgg cag acg       720
Asn Tyr Thr Cys Val Val Glu Asn Lys Phe Gly Ser Ile Arg Gln Thr
225                 230                 235                 240 tac acg ctg gac gtg ctg gag cgc tcc ccg cac cgg ccc atc ctg cag       768
Tyr Thr Leu Asp Val Leu Glu Arg Ser Pro His Arg Pro Ile Leu Gln
                245                 250                 255 gcg ggg ctg ccg gcc aac cag acg gcg gtg ctg ggc agc gac gtg gag       816
Ala Gly Leu Pro Ala Asn Gln Thr Ala Val Leu Gly Ser Asp Val Glu
            260                 265                 270 ttc cac tgc aag gtg tac agt gac gca cag ccc cac atc cag tgg ctc       864
Phe His Cys Lys Val Tyr Ser Asp Ala Gln Pro His Ile Gln Trp Leu
        275                 280                 285 aag cac gtg gag gtg aat ggc agc aag gtg ggc ccg gac ggc aca ccc       912
Lys His Val Glu Val Asn Gly Ser Lys Val Gly Pro Asp Gly Thr Pro
    290                 295                 300 tac gtt acc gtg ctc aag tcc tgg atc agt gag agt gtg gag gcc gac       960
Tyr Val Thr Val Leu Lys Ser Trp Ile Ser Glu Ser Val Glu Ala Asp
305                 310                 315                 320 gtg cgc ctc cgc ctg gcc aat gtg tcg gag cgg gac ggg ggc gag tac      1008
Val Arg Leu Arg Leu Ala Asn Val Ser Glu Arg Asp Gly Gly Glu Tyr
                325                 330                 335 ctc tgt cga gcc acc aat ttc ata ggc gtg gcc gag aag gcc ttt tgg      1056
Leu Cys Arg Ala Thr Asn Phe Ile Gly Val Ala Glu Lys Ala Phe Trp
            340                 345                 350 ctg agc gtt cac ggg ccc cga gca gcc gag gag gag ctg gtg gag gct      1104
```

```
Leu Ser Val His Gly Pro Arg Ala Glu Glu Leu Val Glu Ala
        355             360             365 gac gag gcg ggc agt gtg tat gca ggc atc ctc agc tac ggg gtg ggc    1152
Asp Glu Ala Gly Ser Val Tyr Ala Gly Ile Leu Ser Tyr Gly Val Gly
        370             375             380 ttc ttc ctg ttc atc ctg gtg gtg gcg gct gtg acg ctc tgc cgc ctg    1200
Phe Phe Leu Phe Ile Leu Val Val Ala Ala Val Thr Leu Cys Arg Leu
385             390             395             400 cgc agc ccc ccc aag aaa ggc ctg ggc tcc ccc acc gtg cac aag atc    1248
Arg Ser Pro Pro Lys Lys Gly Leu Gly Ser Pro Thr Val His Lys Ile
            405             410             415 tcc cgc ttc ccg ctc aag cga cag gtg tcc ctg gag tcc aac gcg tcc    1296
Ser Arg Phe Pro Leu Lys Arg Gln Val Ser Leu Glu Ser Asn Ala Ser
        420             425             430 atg agc tcc aac aca cca ctg gtg cgc atc gca agg ctg tcc tca ggg    1344
Met Ser Ser Asn Thr Pro Leu Val Arg Ile Ala Arg Leu Ser Ser Gly
        435             440             445 gag ggc ccc acg ctg gcc aat gtc tcc gag ctc gag ctg cct gcc gac    1392
Glu Gly Pro Thr Leu Ala Asn Val Ser Glu Leu Glu Leu Pro Ala Asp
        450             455             460 ccc aaa tgg gag ctg tct cgg gcc cgg ctg acc ctg ggc aag ccc ctt    1440
Pro Lys Trp Glu Leu Ser Arg Ala Arg Leu Thr Leu Gly Lys Pro Leu
465             470             475             480 ggg gag ggc tgc ttc ggc cag gtg gtc atg gcg gag gcc atc ggc att    1488
Gly Glu Gly Cys Phe Gly Gln Val Val Met Ala Glu Ala Ile Gly Ile
                485             490             495 gac aag gac cgg gcc gcc aag cct gtc acc gta gcc gtg aag atg ctg    1536
Asp Lys Asp Arg Ala Ala Lys Pro Val Thr Val Ala Val Lys Met Leu
            500             505             510 aaa gac gat gcc act gac aag gac ctg tcg gac ctg gtg tct gag atg    1584
Lys Asp Asp Ala Thr Asp Lys Asp Leu Ser Asp Leu Val Ser Glu Met
        515             520             525 gag atg atg aag atg atc ggg aaa cac aaa aac atc atc aac ctg ctg    1632
Glu Met Met Lys Met Ile Gly Lys His Lys Asn Ile Ile Asn Leu Leu
530             535             540 ggc gcc tgc acg cag ggc ggg ccc ctg tac gtg ctg gtg gag tac gcg    1680
Gly Ala Cys Thr Gln Gly Gly Pro Leu Tyr Val Leu Val Glu Tyr Ala
545             550             555             560 gcc aag ggt aac ctg cgg gag ttt ctg cgg gcg cgg cgg ccc ccg ggc    1728
Ala Lys Gly Asn Leu Arg Glu Phe Leu Arg Ala Arg Arg Pro Pro Gly
                565             570             575 ctg gac tac tcc ttc gac acc tgc aag ccg ccc gag gag cag ctc acc    1776
Leu Asp Tyr Ser Phe Asp Thr Cys Lys Pro Pro Glu Glu Gln Leu Thr
            580             585             590 ttc aag gac ctg gtg tcc tgt gcc tac cag gtg gcc cgg ggc atg gag    1824
Phe Lys Asp Leu Val Ser Cys Ala Tyr Gln Val Ala Arg Gly Met Glu
        595             600             605 tac ttg gcc tcc cag aag tgc atc cac agg gac ctg gct gcc cgc aat    1872
Tyr Leu Ala Ser Gln Lys Cys Ile His Arg Asp Leu Ala Ala Arg Asn
610             615             620 gtg ctg gtg acc gag gac aac gtg atg aag atc gca gac ttc ggg ctg    1920
Val Leu Val Thr Glu Asp Asn Val Met Lys Ile Ala Asp Phe Gly Leu
625             630             635             640 gcc cgg gac gtg cac aac ctc gac tac tac aag aag aca acc aac ggc    1968
Ala Arg Asp Val His Asn Leu Asp Tyr Tyr Lys Lys Thr Thr Asn Gly
                645             650             655 cgg ctg ccc gtg aag tgg atg gcg cct gag gcc ttg ttt gac cga gtc    2016
Arg Leu Pro Val Lys Trp Met Ala Pro Glu Ala Leu Phe Asp Arg Val
            660             665             670
```

```
tac act cac cag agt gac gtc tgg tcc ttt ggg gtc ctg ctc tgg gag    2064
Tyr Thr His Gln Ser Asp Val Trp Ser Phe Gly Val Leu Leu Trp Glu
            675                 680                 685 atc ttc acg ctg ggg ggc tcc ccg tac ccc ggc atc cct gtg gag gag    2112
Ile Phe Thr Leu Gly Gly Ser Pro Tyr Pro Gly Ile Pro Val Glu Glu
        690                 695                 700 ctc ttc aag ctg ctg aag gag ggc cac cgc atg gac aag ccc gcc aac    2160
Leu Phe Lys Leu Leu Lys Glu Gly His Arg Met Asp Lys Pro Ala Asn
705                 710                 715                 720 tgc aca cac gac ctg tac atg atc atg cgg gag tgc tgg cat gcc gcg    2208
Cys Thr His Asp Leu Tyr Met Ile Met Arg Glu Cys Trp His Ala Ala
                725                 730                 735 ccc tcc cag agg ccc acc ttc aag cag ctg gtg gag gac ctg gac cgt    2256
Pro Ser Gln Arg Pro Thr Phe Lys Gln Leu Val Glu Asp Leu Asp Arg
            740                 745                 750 gtc ctt acc gtg acg tcc acc gac gta aag gcg aca cag gag gag aac    2304
Val Leu Thr Val Thr Ser Thr Asp Val Lys Ala Thr Gln Glu Glu Asn
        755                 760                 765 cgg gag ctg agg agc agg tgt gag gag ctc cac ggg aag aac ctg gaa    2352
Arg Glu Leu Arg Ser Arg Cys Glu Glu Leu His Gly Lys Asn Leu Glu
770                 775                 780 ctg ggg aag atc atg gac agg ttc gaa gag gtt gtg tac cag gcc atg    2400
Leu Gly Lys Ile Met Asp Arg Phe Glu Glu Val Val Tyr Gln Ala Met
785                 790                 795                 800 gag gaa gtt cag aag cag aag gaa ctt tcc aaa gct gaa atc cag aaa    2448
Glu Glu Val Gln Lys Gln Lys Glu Leu Ser Lys Ala Glu Ile Gln Lys
                805                 810                 815 gtt cta aaa gaa aaa gac caa ctt acc aca gat ctg aac tcc atg gag    2496
Val Leu Lys Glu Lys Asp Gln Leu Thr Thr Asp Leu Asn Ser Met Glu
            820                 825                 830 aag tcc ttc tcc gac ctc ttc aag cgt ttt gag aaa cag aaa gag gtg    2544
Lys Ser Phe Ser Asp Leu Phe Lys Arg Phe Glu Lys Gln Lys Glu Val
        835                 840                 845 atc gag ggc tac cgc aag aac gaa gag tca ctg aag aag tgc gtg gag    2592
Ile Glu Gly Tyr Arg Lys Asn Glu Glu Ser Leu Lys Lys Cys Val Glu
850                 855                 860 gat tac ctg gca agg atc acc cag gag ggc cag agg tac caa gcc ctg    2640
Asp Tyr Leu Ala Arg Ile Thr Gln Glu Gly Gln Arg Tyr Gln Ala Leu
865                 870                 875                 880 aag gcc cac gcg gag gag aag ctg cag ctg gca aac gag gag atc gcc    2688
Lys Ala His Ala Glu Glu Lys Leu Gln Leu Ala Asn Glu Glu Ile Ala
                885                 890                 895 cag gtc cgg agc aag gcc cag gcg gaa gcg ttg gcc ctc cag gcc agc    2736
Gln Val Arg Ser Lys Ala Gln Ala Glu Ala Leu Ala Leu Gln Ala Ser
            900                 905                 910 ctg agg aag gag cag atg cgc atc cag tcg ctg gag aag aca gtg gag    2784
Leu Arg Lys Glu Gln Met Arg Ile Gln Ser Leu Glu Lys Thr Val Glu
        915                 920                 925 cag aag act aaa gag aac gag gag ctg acc agg atc tgc gac gac ctc    2832
Gln Lys Thr Lys Glu Asn Glu Glu Leu Thr Arg Ile Cys Asp Asp Leu
930                 935                 940 atc tcc aag atg gag aag atc tga                                    2856
Ile Ser Lys Met Glu Lys Ile
945                 950

<210> SEQ ID NO 2
<211> LENGTH: 951
<212> TYPE: PRT
<213> ORGANISM: Homo sapiens

<400> SEQUENCE: 2
```

```
Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65              70                  75                  80

Leu Val Pro Ser Glu Arg Val Leu Val Gly Pro Gln Arg Leu Gln Val
            85                  90                  95

Leu Asn Ala Ser His Glu Asp Ser Gly Ala Tyr Ser Cys Arg Gln Arg
        100                 105                 110

Leu Thr Gln Arg Val Leu Cys His Phe Ser Val Arg Val Thr Asp Ala
    115                 120                 125

Pro Ser Ser Gly Asp Asp Glu Asp Gly Glu Asp Glu Ala Glu Asp Thr
130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
            165                 170                 175

Pro Ala Ala Gly Asn Pro Thr Pro Ser Ile Ser Trp Leu Lys Asn Gly
        180                 185                 190

Arg Glu Phe Arg Gly Glu His Arg Ile Gly Gly Ile Lys Leu Arg His
    195                 200                 205

Gln Gln Trp Ser Leu Val Met Glu Ser Val Val Pro Ser Asp Arg Gly
210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
            245                 250                 255

Ala Gly Leu Pro Ala Asn Gln Thr Ala Val Leu Gly Ser Asp Val Glu
        260                 265                 270

Phe His Cys Lys Val Tyr Ser Asp Ala Gln Pro His Ile Gln Trp Leu
    275                 280                 285

Lys His Val Glu Val Asn Gly Ser Lys Val Gly Pro Asp Gly Thr Pro
290                 295                 300

Tyr Val Thr Val Leu Lys Ser Trp Ile Ser Glu Ser Val Glu Ala Asp
305                 310                 315                 320

Val Arg Leu Arg Leu Ala Asn Val Ser Glu Arg Asp Gly Gly Glu Tyr
            325                 330                 335

Leu Cys Arg Ala Thr Asn Phe Ile Gly Val Ala Glu Lys Ala Phe Trp
        340                 345                 350

Leu Ser Val His Gly Pro Arg Ala Ala Glu Glu Glu Leu Val Glu Ala
    355                 360                 365

Asp Glu Ala Gly Ser Val Tyr Ala Gly Ile Leu Ser Tyr Gly Val Gly
370                 375                 380

Phe Phe Leu Phe Ile Leu Val Val Ala Ala Val Thr Leu Cys Arg Leu
385                 390                 395                 400

Arg Ser Pro Pro Lys Lys Gly Leu Gly Ser Pro Thr Val His Lys Ile
            405                 410                 415
```

```
Ser Arg Phe Pro Leu Lys Arg Gln Val Ser Leu Glu Ser Asn Ala Ser
            420                 425                 430

Met Ser Ser Asn Thr Pro Leu Val Arg Ile Ala Arg Leu Ser Ser Gly
        435                 440                 445

Glu Gly Pro Thr Leu Ala Asn Val Ser Glu Leu Glu Leu Pro Ala Asp
    450                 455                 460

Pro Lys Trp Glu Leu Ser Arg Ala Arg Leu Thr Leu Gly Lys Pro Leu
465                 470                 475                 480

Gly Glu Gly Cys Phe Gly Gln Val Val Met Ala Glu Ala Ile Gly Ile
                485                 490                 495

Asp Lys Asp Arg Ala Ala Lys Pro Val Thr Val Ala Val Lys Met Leu
                500                 505                 510

Lys Asp Asp Ala Thr Asp Lys Asp Leu Ser Asp Leu Val Ser Glu Met
            515                 520                 525

Glu Met Met Lys Met Ile Gly Lys His Lys Asn Ile Ile Asn Leu Leu
530                 535                 540

Gly Ala Cys Thr Gln Gly Gly Pro Leu Tyr Val Leu Val Glu Tyr Ala
545                 550                 555                 560

Ala Lys Gly Asn Leu Arg Glu Phe Leu Arg Ala Arg Arg Pro Pro Gly
                565                 570                 575

Leu Asp Tyr Ser Phe Asp Thr Cys Lys Pro Pro Glu Glu Gln Leu Thr
                580                 585                 590

Phe Lys Asp Leu Val Ser Cys Ala Tyr Gln Val Ala Arg Gly Met Glu
            595                 600                 605

Tyr Leu Ala Ser Gln Lys Cys Ile His Arg Asp Leu Ala Ala Arg Asn
            610                 615                 620

Val Leu Val Thr Glu Asp Asn Val Met Lys Ile Ala Asp Phe Gly Leu
625                 630                 635                 640

Ala Arg Asp Val His Asn Leu Asp Tyr Tyr Lys Lys Thr Thr Asn Gly
                645                 650                 655

Arg Leu Pro Val Lys Trp Met Ala Pro Glu Ala Leu Phe Asp Arg Val
                660                 665                 670

Tyr Thr His Gln Ser Asp Val Trp Ser Phe Gly Val Leu Leu Trp Glu
            675                 680                 685

Ile Phe Thr Leu Gly Gly Ser Pro Tyr Pro Gly Ile Pro Val Glu Glu
            690                 695                 700

Leu Phe Lys Leu Leu Lys Glu Gly His Arg Met Asp Lys Pro Ala Asn
705                 710                 715                 720

Cys Thr His Asp Leu Tyr Met Ile Met Arg Glu Cys Trp His Ala Ala
                725                 730                 735

Pro Ser Gln Arg Pro Thr Phe Lys Gln Leu Val Glu Asp Leu Asp Arg
            740                 745                 750

Val Leu Thr Val Thr Ser Thr Asp Val Lys Ala Thr Gln Glu Glu Asn
            755                 760                 765

Arg Glu Leu Arg Ser Arg Cys Glu Glu Leu His Gly Lys Asn Leu Glu
        770                 775                 780

Leu Gly Lys Ile Met Asp Arg Phe Glu Val Val Tyr Gln Ala Met
785                 790                 795                 800

Glu Glu Val Gln Lys Gln Lys Glu Leu Ser Lys Ala Glu Ile Gln Lys
                805                 810                 815

Val Leu Lys Glu Lys Asp Gln Leu Thr Thr Asp Leu Asn Ser Met Glu
            820                 825                 830

Lys Ser Phe Ser Asp Leu Phe Lys Arg Phe Glu Lys Gln Lys Glu Val
```

```
                  835                 840                 845
Ile Glu Gly Tyr Arg Lys Asn Glu Glu Ser Leu Lys Lys Cys Val Glu
850                 855                 860

Asp Tyr Leu Ala Arg Ile Thr Gln Glu Gly Gln Arg Tyr Gln Ala Leu
865                 870                 875                 880

Lys Ala His Ala Glu Lys Leu Gln Leu Ala Asn Glu Glu Ile Ala
                885                 890                 895

Gln Val Arg Ser Lys Ala Gln Ala Glu Leu Ala Leu Gln Ala Ser
                900                 905                 910

Leu Arg Lys Glu Gln Met Arg Ile Gln Ser Leu Glu Lys Thr Val Glu
                915                 920                 925

Gln Lys Thr Lys Glu Asn Glu Glu Leu Thr Arg Ile Cys Asp Asp Leu
930                 935                 940

Ile Ser Lys Met Glu Lys Ile
945                 950

<210> SEQ ID NO 3
<211> LENGTH: 2961
<212> TYPE: DNA
<213> ORGANISM: Homo sapiens
<220> FEATURE:
<221> NAME/KEY: CDS
<222> LOCATION: (1)..(2961)

<400> SEQUENCE: 3 atg ggc gcc cct gcc tgc gcc ctc gcg ctc tgc gtg gcc gtg gcc atc     48
Met Gly Ala Pro Ala Cys Ala Leu Ala Leu Cys Val Ala Val Ala Ile
1               5                   10                  15 gtg gcc ggc gcc tcc tcg gag tcc ttg ggg acg gag cag cgc gtc gtg     96
Val Ala Gly Ala Ser Ser Glu Ser Leu Gly Thr Glu Gln Arg Val Val
                20                  25                  30 ggg cga gcg gca gaa gtc ccg ggc cca gag ccc ggc cag cag gag cag    144
Gly Arg Ala Ala Glu Val Pro Gly Pro Glu Pro Gly Gln Gln Glu Gln
            35                  40                  45 ttg gtc ttc ggc agc ggg gat gct gtg gag ctg agc tgt ccc ccg ccc    192
Leu Val Phe Gly Ser Gly Asp Ala Val Glu Leu Ser Cys Pro Pro Pro
        50                  55                  60 ggg ggt ggt ccc atg ggg ccc act gtc tgg gtc aag gat ggc aca ggg    240
Gly Gly Gly Pro Met Gly Pro Thr Val Trp Val Lys Asp Gly Thr Gly
65                  70                  75                  80 ctg gtg ccc tcg gag cgt gtc ctg gtg ggg ccc cag cgg ctg cag gtg    288
Leu Val Pro Ser Glu Arg Val Leu Val Gly Pro Gln Arg Leu Gln Val
                85                  90                  95 ctg aat gcc tcc cac gag gac tcc ggg gcc tac agc tgc cgg cag cgg    336
Leu Asn Ala Ser His Glu Asp Ser Gly Ala Tyr Ser Cys Arg Gln Arg
            100                 105                 110 ctc acg cag cgc gta ctg tgc cac ttc agt gtg cgg gtg aca gac gct    384
Leu Thr Gln Arg Val Leu Cys His Phe Ser Val Arg Val Thr Asp Ala
        115                 120                 125 cca tcc tcg gga gat gac gaa gac ggg gag gac gag gct gag gac aca    432
Pro Ser Ser Gly Asp Asp Glu Asp Gly Glu Asp Glu Ala Glu Asp Thr
    130                 135                 140 ggt gtg gac aca ggg gcc cct tac tgg aca cgg ccc gag cgg atg gac    480
Gly Val Asp Thr Gly Ala Pro Tyr Trp Thr Arg Pro Glu Arg Met Asp
145                 150                 155                 160 aag aag ctg ctg gcc gtg ccg gcc gcc aac acc gtc cgc ttc cgc tgc    528
Lys Lys Leu Leu Ala Val Pro Ala Ala Asn Thr Val Arg Phe Arg Cys
                165                 170                 175 cca gcc gct ggc aac ccc act ccc tcc atc tcc tgg ctg aag aac ggc    576
```

```
                Pro Ala Ala Gly Asn Pro Thr Pro Ser Ile Ser Trp Leu Lys Asn Gly
                            180                 185                 190 agg gag ttc cgc ggc gag cac cgc att gga ggc atc aag ctg cgg cat        624
Arg Glu Phe Arg Gly Glu His Arg Ile Gly Gly Ile Lys Leu Arg His
            195                 200                 205 cag cag tgg agc ctg gtc atg gaa agc gtg gtg ccc tcg gac cgc ggc        672
Gln Gln Trp Ser Leu Val Met Glu Ser Val Val Pro Ser Asp Arg Gly
        210                 215                 220 aac tac acc tgc gtc gtg gag aac aag ttt ggc agc atc cgg cag acg        720
Asn Tyr Thr Cys Val Val Glu Asn Lys Phe Gly Ser Ile Arg Gln Thr
225                 230                 235                 240 tac acg ctg gac gtg ctg gag cgc tcc ccg cac cgg ccc atc ctg cag        768
Tyr Thr Leu Asp Val Leu Glu Arg Ser Pro His Arg Pro Ile Leu Gln
                245                 250                 255 gcg ggg ctg ccg gcc aac cag acg gcg gtg ctg ggc agc gac gtg gag        816
Ala Gly Leu Pro Ala Asn Gln Thr Ala Val Leu Gly Ser Asp Val Glu
            260                 265                 270 ttc cac tgc aag gtg tac agt gac gca cag ccc cac atc cag tgg ctc        864
Phe His Cys Lys Val Tyr Ser Asp Ala Gln Pro His Ile Gln Trp Leu
        275                 280                 285 aag cac gtg gag gtg aat ggc agc aag gtg ggc ccg gac ggc aca ccc        912
Lys His Val Glu Val Asn Gly Ser Lys Val Gly Pro Asp Gly Thr Pro
    290                 295                 300 tac gtt acc gtg ctc aag tcc tgg atc agt gag agt gtg gag gcc gac        960
Tyr Val Thr Val Leu Lys Ser Trp Ile Ser Glu Ser Val Glu Ala Asp
305                 310                 315                 320 gtg cgc ctc cgc ctg gcc aat gtg tcg gag cgg gac ggg ggc gag tac       1008
Val Arg Leu Arg Leu Ala Asn Val Ser Glu Arg Asp Gly Gly Glu Tyr
                325                 330                 335 ctc tgt cga gcc acc aat ttc ata ggc gtg gcc gag aag gcc ttt tgg       1056
Leu Cys Arg Ala Thr Asn Phe Ile Gly Val Ala Glu Lys Ala Phe Trp
            340                 345                 350 ctg agc gtt cac ggg ccc cga gca gcc gag gag gag ctg gtg gag gct       1104
Leu Ser Val His Gly Pro Arg Ala Ala Glu Glu Glu Leu Val Glu Ala
        355                 360                 365 gac gag gcg ggc agt gtg tat gca ggc atc ctc agc tac ggg gtg ggc       1152
Asp Glu Ala Gly Ser Val Tyr Ala Gly Ile Leu Ser Tyr Gly Val Gly
    370                 375                 380 ttc ctc ctg ttc atc ctg gtg gtg gcg gct gtg acg ctc tgc cgc ctg       1200
Phe Leu Leu Phe Ile Leu Val Val Ala Ala Val Thr Leu Cys Arg Leu
385                 390                 395                 400 cgc agc ccc ccc aag aaa ggc ctg ggc tcc ccc acc gtg cac aag atc       1248
Arg Ser Pro Pro Lys Lys Gly Leu Gly Ser Pro Thr Val His Lys Ile
                405                 410                 415 tcc cgc ttc ccg ctc aag cga cag gtg tcc ctg gag tcc aac gcg tcc       1296
Ser Arg Phe Pro Leu Lys Arg Gln Val Ser Leu Glu Ser Asn Ala Ser
            420                 425                 430 atg agc tcc aac aca cca ctg gtg cgc atc gca agg ctg tcc tca ggg       1344
Met Ser Ser Asn Thr Pro Leu Val Arg Ile Ala Arg Leu Ser Ser Gly
        435                 440                 445 gag ggc ccc acg ctg gcc aat gtc tcc gag ctc gag ctg cct gcc gac       1392
Glu Gly Pro Thr Leu Ala Asn Val Ser Glu Leu Glu Leu Pro Ala Asp
    450                 455                 460 ccc aaa tgg gag ctg tct cgg gcc cgg ctg acc ctg ggc aag ccc ctt       1440
Pro Lys Trp Glu Leu Ser Arg Ala Arg Leu Thr Leu Gly Lys Pro Leu
465                 470                 475                 480 ggg gag ggc tgc ttc ggc cag gtg gtc atg gcg gag gcc atc ggc att       1488
Gly Glu Gly Cys Phe Gly Gln Val Val Met Ala Glu Ala Ile Gly Ile
                485                 490                 495
```

```
gac aag gac cgg gcc gcc aag cct gtc acc gta gcc gtg aag atg ctg    1536
Asp Lys Asp Arg Ala Ala Lys Pro Val Thr Val Ala Val Lys Met Leu
            500                 505                 510 aaa gac gat gcc act gac aag gac ctg tcg gac ctg gtg tct gag atg    1584
Lys Asp Asp Ala Thr Asp Lys Asp Leu Ser Asp Leu Val Ser Glu Met
        515                 520                 525 gag atg atg aag atg atc ggg aaa cac aaa aac atc atc aac ctg ctg    1632
Glu Met Met Lys Met Ile Gly Lys His Lys Asn Ile Ile Asn Leu Leu
    530                 535                 540 ggc gcc tgc acg cag ggc ggg ccc ctg tac gtg ctg gtg gag tac gcg    1680
Gly Ala Cys Thr Gln Gly Gly Pro Leu Tyr Val Leu Val Glu Tyr Ala
545                 550                 555                 560 gcc aag ggt aac ctg cgg gag ttt ctg cgg gcg cgg cgg ccc ccg ggc    1728
Ala Lys Gly Asn Leu Arg Glu Phe Leu Arg Ala Arg Arg Pro Pro Gly
                565                 570                 575 ctg gac tac tcc ttc gac acc tgc aag ccg ccc gag gag cag ctc acc    1776
Leu Asp Tyr Ser Phe Asp Thr Cys Lys Pro Pro Glu Glu Gln Leu Thr
            580                 585                 590 ttc aag gac ctg gtg tcc tgt gcc tac cag gtg gcc cgg ggc atg gag    1824
Phe Lys Asp Leu Val Ser Cys Ala Tyr Gln Val Ala Arg Gly Met Glu
        595                 600                 605 tac ttg gcc tcc cag aag tgc atc cac agg gac ctg gct gcc cgc aat    1872
Tyr Leu Ala Ser Gln Lys Cys Ile His Arg Asp Leu Ala Ala Arg Asn
    610                 615                 620 gtg ctg gtg acc gag gac aac gtg atg aag atc gca gac ttc ggg ctg    1920
Val Leu Val Thr Glu Asp Asn Val Met Lys Ile Ala Asp Phe Gly Leu
625                 630                 635                 640 gcc cgg gac gtg cac aac ctc gac tac tac aag aag aca acc aac ggc    1968
Ala Arg Asp Val His Asn Leu Asp Tyr Tyr Lys Lys Thr Thr Asn Gly
                645                 650                 655 cgg ctg ccc gtg aag tgg atg gcg cct gag gcc ttg ttt gac cga gtc    2016
Arg Leu Pro Val Lys Trp Met Ala Pro Glu Ala Leu Phe Asp Arg Val
            660                 665                 670 tac act cac cag agt gac gtc tgg tcc ttt ggg gtc ctg ctc tgg gag    2064
Tyr Thr His Gln Ser Asp Val Trp Ser Phe Gly Val Leu Leu Trp Glu
        675                 680                 685 atc ttc acg ctg ggg ggc tcc ccg tac ccc ggc atc cct gtg gag gag    2112
Ile Phe Thr Leu Gly Gly Ser Pro Tyr Pro Gly Ile Pro Val Glu Glu
    690                 695                 700 ctc ttc aag ctg ctg aag gag ggc cac cgc atg gac aag ccc gcc aac    2160
Leu Phe Lys Leu Leu Lys Glu Gly His Arg Met Asp Lys Pro Ala Asn
705                 710                 715                 720 tgc aca cac gac ctg tac atg atc atg cgg gag tgc tgg cat gcc gcg    2208
Cys Thr His Asp Leu Tyr Met Ile Met Arg Glu Cys Trp His Ala Ala
                725                 730                 735 ccc tcc cag agg ccc acc ttc aag cag ctg gtg gag gac ctg gac cgt    2256
Pro Ser Gln Arg Pro Thr Phe Lys Gln Leu Val Glu Asp Leu Asp Arg
            740                 745                 750 gtc ctt acc gtg acg tcc acc gac gtg cca ggc cca ccc cca ggt gtt    2304
Val Leu Thr Val Thr Ser Thr Asp Val Pro Gly Pro Pro Pro Gly Val
        755                 760                 765 ccc gcg cct ggg ggc cca ccc ctg tcc acc gga cct ata gtg gac ctg    2352
Pro Ala Pro Gly Gly Pro Pro Leu Ser Thr Gly Pro Ile Val Asp Leu
    770                 775                 780 ctc cag tac agc cag aag gac ctg gat gca gtg gta aag gcg aca cag    2400
Leu Gln Tyr Ser Gln Lys Asp Leu Asp Ala Val Val Lys Ala Thr Gln
785                 790                 795                 800 gag gag aac cgg gag ctg agg agc agg tgt gag gag ctc cac ggg aag    2448
Glu Glu Asn Arg Glu Leu Arg Ser Arg Cys Glu Glu Leu His Gly Lys
                805                 810                 815
```

```
aac ctg gaa ctg ggg aag atc atg gac agg ttc gaa gag gtt gtg tac      2496
Asn Leu Glu Leu Gly Lys Ile Met Asp Arg Phe Glu Glu Val Val Tyr
            820                 825                 830 cag gcc atg gag gaa gtt cag aag cag aag gaa ctt tcc aaa gct gaa      2544
Gln Ala Met Glu Glu Val Gln Lys Gln Lys Glu Leu Ser Lys Ala Glu
        835                 840                 845 atc cag aaa gtt cta aaa gaa aaa gac caa ctt acc aca gat ctg aac      2592
Ile Gln Lys Val Leu Lys Glu Lys Asp Gln Leu Thr Thr Asp Leu Asn
850                 855                 860 tcc atg gag aag tcc ttc tcc gac ctc ttc aag cgt ttt gag aaa cag      2640
Ser Met Glu Lys Ser Phe Ser Asp Leu Phe Lys Arg Phe Glu Lys Gln
865                 870                 875                 880 aaa gag gtg atc gag ggc tac cgc aag aac gaa gag tca ctg aag aag      2688
Lys Glu Val Ile Glu Gly Tyr Arg Lys Asn Glu Glu Ser Leu Lys Lys
                885                 890                 895 tgc gtg gag gat tac ctg gca agg atc acc cag gag ggc cag agg tac      2736
Cys Val Glu Asp Tyr Leu Ala Arg Ile Thr Gln Glu Gly Gln Arg Tyr
            900                 905                 910 caa gcc ctg aag gcc cac gcg gag gag aag ctg cag ctg gca aac gag      2784
Gln Ala Leu Lys Ala His Ala Glu Glu Lys Leu Gln Leu Ala Asn Glu
        915                 920                 925 gag atc gcc cag gtc cgg agc aag gcc cag gcg gaa gcg ttg gcc ctc      2832
Glu Ile Ala Gln Val Arg Ser Lys Ala Gln Ala Glu Ala Leu Ala Leu
930                 935                 940 cag gcc agc ctg agg aag gag cag atg cgc atc cag tcg ctg gag aag      2880
Gln Ala Ser Leu Arg Lys Glu Gln Met Arg Ile Gln Ser Leu Glu Lys
945                 950                 955                 960 aca gtg gag cag aag act aaa gag aac gag gag ctg acc agg atc tgc      2928
Thr Val Glu Gln Lys Thr Lys Glu Asn Glu Glu Leu Thr Arg Ile Cys
                965                 970                 975 gac gac ctc atc tcc aag atg gag aag atc tga                          2961
Asp Asp Leu Ile Ser Lys Met Glu Lys Ile
            980                 985

<210> SEQ ID NO 4
<211> LENGTH: 986
<212> TYPE: PRT
<213> ORGANISM: Homo sapiens

<400> SEQUENCE: 4

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140
```

```
Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
            165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Ile Lys Leu Arg His
        195                 200                 205

Gln Gln Trp Ser Leu Val Met Glu Ser Val Val Pro Ser Asp Arg Gly
        210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
            245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
290                 295                 300

Tyr Val Thr Val Leu Lys Ser Trp Ile Ser Glu Ser Val Glu Ala Asp
305                 310                 315                 320

Val Arg Leu Arg Leu Ala Asn Val Ser Glu Arg Asp Gly Gly Glu Tyr
            325                 330                 335

Leu Cys Arg Ala Thr Asn Phe Ile Gly Val Ala Glu Lys Ala Phe Trp
            340                 345                 350

Leu Ser Val His Gly Pro Arg Ala Ala Glu Glu Leu Val Glu Ala
            355                 360                 365

Asp Glu Ala Gly Ser Val Tyr Ala Gly Ile Leu Ser Tyr Gly Val Gly
    370                 375                 380

Phe Leu Leu Phe Ile Leu Val Val Ala Ala Val Thr Leu Cys Arg Leu
385                 390                 395                 400

Arg Ser Pro Pro Lys Lys Gly Leu Gly Ser Pro Thr Val His Lys Ile
            405                 410                 415

Ser Arg Phe Pro Leu Lys Arg Gln Val Ser Leu Glu Ser Asn Ala Ser
            420                 425                 430

Met Ser Ser Asn Thr Pro Leu Val Arg Ile Ala Arg Leu Ser Ser Gly
            435                 440                 445

Glu Gly Pro Thr Leu Ala Asn Val Ser Glu Leu Glu Leu Pro Ala Asp
    450                 455                 460

Pro Lys Trp Glu Leu Ser Arg Ala Arg Leu Thr Leu Gly Lys Pro Leu
465                 470                 475                 480

Gly Glu Gly Cys Phe Gly Gln Val Val Met Ala Glu Ala Ile Gly Ile
            485                 490                 495

Asp Lys Asp Arg Ala Ala Lys Pro Val Thr Val Ala Val Lys Met Leu
            500                 505                 510

Lys Asp Asp Ala Thr Asp Lys Asp Leu Ser Asp Leu Val Ser Glu Met
            515                 520                 525

Glu Met Met Lys Met Ile Gly Lys His Lys Asn Ile Ile Asn Leu Leu
    530                 535                 540

Gly Ala Cys Thr Gln Gly Gly Pro Leu Tyr Val Leu Val Glu Tyr Ala
545                 550                 555                 560
```

```
Ala Lys Gly Asn Leu Arg Glu Phe Leu Arg Ala Arg Pro Pro Gly
            565                 570                 575

Leu Asp Tyr Ser Phe Asp Thr Cys Lys Pro Pro Glu Glu Gln Leu Thr
            580                 585                 590

Phe Lys Asp Leu Val Ser Cys Ala Tyr Gln Val Ala Arg Gly Met Glu
            595                 600                 605

Tyr Leu Ala Ser Gln Lys Cys Ile His Arg Asp Leu Ala Ala Arg Asn
            610                 615                 620

Val Leu Val Thr Glu Asp Asn Val Met Lys Ile Ala Asp Phe Gly Leu
625                 630                 635                 640

Ala Arg Asp Val His Asn Leu Asp Tyr Tyr Lys Lys Thr Thr Asn Gly
                645                 650                 655

Arg Leu Pro Val Lys Trp Met Ala Pro Glu Ala Leu Phe Asp Arg Val
            660                 665                 670

Tyr Thr His Gln Ser Asp Val Trp Ser Phe Gly Val Leu Leu Trp Glu
            675                 680                 685

Ile Phe Thr Leu Gly Gly Ser Pro Tyr Pro Gly Ile Pro Val Glu Glu
            690                 695                 700

Leu Phe Lys Leu Leu Lys Glu Gly His Arg Met Asp Lys Pro Ala Asn
705                 710                 715                 720

Cys Thr His Asp Leu Tyr Met Ile Met Arg Glu Cys Trp His Ala Ala
                725                 730                 735

Pro Ser Gln Arg Pro Thr Phe Lys Gln Leu Val Glu Asp Leu Asp Arg
                740                 745                 750

Val Leu Thr Val Thr Ser Thr Asp Val Pro Gly Pro Pro Gly Val
            755                 760                 765

Pro Ala Pro Gly Gly Pro Pro Leu Ser Thr Gly Pro Ile Val Asp Leu
770                 775                 780

Leu Gln Tyr Ser Gln Lys Asp Leu Asp Ala Val Val Lys Ala Thr Gln
785                 790                 795                 800

Glu Glu Asn Arg Glu Leu Arg Ser Arg Cys Glu Glu Leu His Gly Lys
                805                 810                 815

Asn Leu Glu Leu Gly Lys Ile Met Asp Arg Phe Glu Glu Val Val Tyr
            820                 825                 830

Gln Ala Met Glu Glu Val Gln Lys Gln Lys Glu Leu Ser Lys Ala Glu
            835                 840                 845

Ile Gln Lys Val Leu Lys Glu Lys Asp Gln Leu Thr Thr Asp Leu Asn
850                 855                 860

Ser Met Glu Lys Ser Phe Ser Asp Leu Phe Lys Arg Phe Glu Lys Gln
865                 870                 875                 880

Lys Glu Val Ile Glu Gly Tyr Arg Lys Asn Glu Glu Ser Leu Lys Lys
                885                 890                 895

Cys Val Glu Asp Tyr Leu Ala Arg Ile Thr Gln Glu Gly Gln Arg Tyr
                900                 905                 910

Gln Ala Leu Lys Ala His Ala Glu Glu Lys Leu Gln Leu Ala Asn Glu
            915                 920                 925

Glu Ile Ala Gln Val Arg Ser Lys Ala Gln Ala Glu Ala Leu Ala Leu
            930                 935                 940

Gln Ala Ser Leu Arg Lys Glu Gln Met Arg Ile Gln Ser Leu Glu Lys
945                 950                 955                 960

Thr Val Glu Gln Lys Thr Lys Glu Asn Glu Glu Leu Thr Arg Ile Cys
                965                 970                 975

Asp Asp Leu Ile Ser Lys Met Glu Lys Ile
```

<210> SEQ ID NO 5
<211> LENGTH: 3003
<212> TYPE: DNA
<213> ORGANISM: Homo sapiens
<220> FEATURE:
<221> NAME/KEY: CDS
<222> LOCATION: (1)..(3003)

<400> SEQUENCE: 5

| | | | | | | | | | | | | | | | | |
|---|---|---|---|---|---|---|---|---|---|---|---|---|---|---|---|---|
| atg | ggc | gcc | cct | gcc | tgc | gcc | ctc | gcg | ctc | tgc | gtg | gcc | gtg | gcc | atc | 48 |
| Met | Gly | Ala | Pro | Ala | Cys | Ala | Leu | Ala | Leu | Cys | Val | Ala | Val | Ala | Ile | |
| 1 | | | 5 | | | | | 10 | | | | | 15 | | | |
| gtg | gcc | ggc | gcc | tcc | tcg | gag | tcc | ttg | ggg | acg | gag | cag | cgc | gtc | gtg | 96 |
| Val | Ala | Gly | Ala | Ser | Ser | Glu | Ser | Leu | Gly | Thr | Glu | Gln | Arg | Val | Val | |
| | | | 20 | | | | 25 | | | | | 30 | | | | |
| ggg | cga | gcg | gca | gaa | gtc | ccg | ggc | cca | gag | ccc | ggc | cag | cag | gag | cag | 144 |
| Gly | Arg | Ala | Ala | Glu | Val | Pro | Gly | Pro | Glu | Pro | Gly | Gln | Gln | Glu | Gln | |
| | | 35 | | | | | 40 | | | | | 45 | | | | |
| ttg | gtc | ttc | ggc | agc | ggg | gat | gct | gtg | gag | ctg | agc | tgt | ccc | ccg | ccc | 192 |
| Leu | Val | Phe | Gly | Ser | Gly | Asp | Ala | Val | Glu | Leu | Ser | Cys | Pro | Pro | Pro | |
| 50 | | | | | 55 | | | | | 60 | | | | | | |
| ggg | ggt | ggt | ccc | atg | ggg | ccc | act | gtc | tgg | gtc | aag | gat | ggc | aca | ggg | 240 |
| Gly | Gly | Gly | Pro | Met | Gly | Pro | Thr | Val | Trp | Val | Lys | Asp | Gly | Thr | Gly | |
| 65 | | | | | 70 | | | | | 75 | | | | | 80 | |
| ctg | gtg | ccc | tcg | gag | cgt | gtc | ctg | gtg | ggg | ccc | cag | cgg | ctg | cag | gtg | 288 |
| Leu | Val | Pro | Ser | Glu | Arg | Val | Leu | Val | Gly | Pro | Gln | Arg | Leu | Gln | Val | |
| | | | | 85 | | | | | 90 | | | | | 95 | | |
| ctg | aat | gcc | tcc | cac | gag | gac | tcc | ggg | gcc | tac | agc | tgc | cgg | cag | cgg | 336 |
| Leu | Asn | Ala | Ser | His | Glu | Asp | Ser | Gly | Ala | Tyr | Ser | Cys | Arg | Gln | Arg | |
| | | | 100 | | | | | 105 | | | | | 110 | | | |
| ctc | acg | cag | cgc | gta | ctg | tgc | cac | ttc | agt | gtg | cgg | gtg | aca | gac | gct | 384 |
| Leu | Thr | Gln | Arg | Val | Leu | Cys | His | Phe | Ser | Val | Arg | Val | Thr | Asp | Ala | |
| | | 115 | | | | | 120 | | | | | 125 | | | | |
| cca | tcc | tcg | gga | gat | gac | gaa | gac | ggg | gag | gac | gag | gct | gag | gac | aca | 432 |
| Pro | Ser | Ser | Gly | Asp | Asp | Glu | Asp | Gly | Glu | Asp | Glu | Ala | Glu | Asp | Thr | |
| 130 | | | | | 135 | | | | | 140 | | | | | | |
| ggt | gtg | gac | aca | ggg | gcc | cct | tac | tgg | aca | cgg | ccc | gag | cgg | atg | gac | 480 |
| Gly | Val | Asp | Thr | Gly | Ala | Pro | Tyr | Trp | Thr | Arg | Pro | Glu | Arg | Met | Asp | |
| 145 | | | | | 150 | | | | | 155 | | | | | 160 | |
| aag | aag | ctg | ctg | gcc | gtg | ccg | gcc | gcc | aac | acc | gtc | cgc | ttc | cgc | tgc | 528 |
| Lys | Lys | Leu | Leu | Ala | Val | Pro | Ala | Ala | Asn | Thr | Val | Arg | Phe | Arg | Cys | |
| | | | | 165 | | | | | 170 | | | | | 175 | | |
| cca | gcc | gct | ggc | aac | ccc | act | ccc | tcc | atc | tcc | tgg | ctg | aag | aac | ggc | 576 |
| Pro | Ala | Ala | Gly | Asn | Pro | Thr | Pro | Ser | Ile | Ser | Trp | Leu | Lys | Asn | Gly | |
| | | | 180 | | | | | 185 | | | | | 190 | | | |
| agg | gag | ttc | cgc | ggc | gag | cac | cgc | att | gga | ggc | atc | aag | ctg | cgg | cat | 624 |
| Arg | Glu | Phe | Arg | Gly | Glu | His | Arg | Ile | Gly | Gly | Ile | Lys | Leu | Arg | His | |
| | | 195 | | | | | 200 | | | | | 205 | | | | |
| cag | cag | tgg | agc | ctg | gtc | atg | gaa | agc | gtg | gtg | ccc | tcg | gac | cgc | ggc | 672 |
| Gln | Gln | Trp | Ser | Leu | Val | Met | Glu | Ser | Val | Val | Pro | Ser | Asp | Arg | Gly | |
| | | 210 | | | | | 215 | | | | | 220 | | | | |
| aac | tac | acc | tgc | gtc | gtg | gag | aac | aag | ttt | ggc | agc | atc | cgg | cag | acg | 720 |
| Asn | Tyr | Thr | Cys | Val | Val | Glu | Asn | Lys | Phe | Gly | Ser | Ile | Arg | Gln | Thr | |
| 225 | | | | | 230 | | | | | 235 | | | | | 240 | |
| tac | acg | ctg | gac | gtg | ctg | gag | cgc | tcc | ccg | cac | cgg | ccc | atc | ctg | cag | 768 |
| Tyr | Thr | Leu | Asp | Val | Leu | Glu | Arg | Ser | Pro | His | Arg | Pro | Ile | Leu | Gln | |
| | | | | 245 | | | | | 250 | | | | | 255 | | |
| gcg | ggg | ctg | ccg | gcc | aac | cag | acg | gcg | gtg | ctg | ggc | agc | gac | gtg | gag | 816 |
| Ala | Gly | Leu | Pro | Ala | Asn | Gln | Thr | Ala | Val | Leu | Gly | Ser | Asp | Val | Glu | |

-continued

| | | |
|---|---|---|
| ttc cac tgc aag gtg tac agt gac gca cag ccc cac atc cag tgg ctc<br>Phe His Cys Lys Val Tyr Ser Asp Ala Gln Pro His Ile Gln Trp Leu<br>275                       280                   285 | 864 |
| aag cac gtg gag gtg aat ggc agc aag gtg ggc ccg gac ggc aca ccc<br>Lys His Val Glu Val Asn Gly Ser Lys Val Gly Pro Asp Gly Thr Pro<br>290                       295                   300 | 912 |
| tac gtt acc gtg ctc aag tcc tgg atc agt gag agt gtg gag gcc gac<br>Tyr Val Thr Val Leu Lys Ser Trp Ile Ser Glu Ser Val Glu Ala Asp<br>305                       310                   315                   320 | 960 |
| gtg cgc ctc cgc ctg gcc aat gtg tcg gag cgg gac ggg ggc gag tac<br>Val Arg Leu Arg Leu Ala Asn Val Ser Glu Arg Asp Gly Gly Glu Tyr<br>325                     330                   335 | 1008 |
| ctc tgt cga gcc acc aat ttc ata ggc gtg gcc gag aag gcc ttt tgg<br>Leu Cys Arg Ala Thr Asn Phe Ile Gly Val Ala Glu Lys Ala Phe Trp<br>340                     345                   350 | 1056 |
| ctg agc gtt cac ggg ccc cga gca gcc gag gag gag ctg gtg gag gct<br>Leu Ser Val His Gly Pro Arg Ala Ala Glu Glu Glu Leu Val Glu Ala<br>355                     360                   365 | 1104 |
| gac gag gcg ggc agt gtg tat gca ggc atc ctc agc tac ggg gtg ggc<br>Asp Glu Ala Gly Ser Val Tyr Ala Gly Ile Leu Ser Tyr Gly Val Gly<br>370                     375                   380 | 1152 |
| ttc ttc ctg ttc atc ctg gtg gtg gcg gct gtg acg ctc tgc cgc ctg<br>Phe Phe Leu Phe Ile Leu Val Val Ala Ala Val Thr Leu Cys Arg Leu<br>385                     390                   395                   400 | 1200 |
| cgc agc ccc ccc aag aaa ggc ctg ggc tcc ccc acc gtg cac aag atc<br>Arg Ser Pro Pro Lys Lys Gly Leu Gly Ser Pro Thr Val His Lys Ile<br>405                     410                   415 | 1248 |
| tcc cgc ttc ccg ctc aag cga cag gtg tcc ctg gag tcc aac gcg tcc<br>Ser Arg Phe Pro Leu Lys Arg Gln Val Ser Leu Glu Ser Asn Ala Ser<br>420                     425                   430 | 1296 |
| atg agc tcc aac aca cca ctg gtg cgc atc gca agg ctg tcc tca ggg<br>Met Ser Ser Asn Thr Pro Leu Val Arg Ile Ala Arg Leu Ser Ser Gly<br>435                     440                   445 | 1344 |
| gag ggc ccc acg ctg gcc aat gtc tcc gag ctc gag ctg cct gcc gac<br>Glu Gly Pro Thr Leu Ala Asn Val Ser Glu Leu Glu Leu Pro Ala Asp<br>450                     455                   460 | 1392 |
| ccc aaa tgg gag ctg tct cgg gcc cgg ctg acc ctg ggc aag ccc ctt<br>Pro Lys Trp Glu Leu Ser Arg Ala Arg Leu Thr Leu Gly Lys Pro Leu<br>465                     470                   475                   480 | 1440 |
| ggg gag ggc tgc ttc ggc cag gtg gtc atg gcg gag gcc atc ggc att<br>Gly Glu Gly Cys Phe Gly Gln Val Val Met Ala Glu Ala Ile Gly Ile<br>485                     490                   495 | 1488 |
| gac aag gac cgg gcc gcc aag cct gtc acc gta gcc gtg aag atg ctg<br>Asp Lys Asp Arg Ala Ala Lys Pro Val Thr Val Ala Val Lys Met Leu<br>500                     505                   510 | 1536 |
| aaa gac gat gcc act gac aag gac ctg tcg gac ctg gtg tct gag atg<br>Lys Asp Asp Ala Thr Asp Lys Asp Leu Ser Asp Leu Val Ser Glu Met<br>515                     520                   525 | 1584 |
| gag atg atg aaa atg atc ggg aaa cac aaa aac atc atc aac ctg ctg<br>Glu Met Met Lys Met Ile Gly Lys His Lys Asn Ile Ile Asn Leu Leu<br>530                     535                   540 | 1632 |
| ggc gcc tgc acg cag ggc ggg ccc ctg tac gtg ctg gtg gag tac gcg<br>Gly Ala Cys Thr Gln Gly Gly Pro Leu Tyr Val Leu Val Glu Tyr Ala<br>545                     550                   555                   560 | 1680 |
| gcc aag ggt aac ctg cgg gag ttt ctg cgg gcg cgg cgg ccc ccg ggc<br>Ala Lys Gly Asn Leu Arg Glu Phe Leu Arg Ala Arg Arg Pro Pro Gly<br>565                     570                   575 | 1728 |
| ctg gac tac tcc ttc gac acc tgc aag ccg ccc gag gag cag ctc acc | 1776 |

```
Leu Asp Tyr Ser Phe Asp Thr Cys Lys Pro Pro Glu Glu Gln Leu Thr
            580                 585                 590 ttc aag gac ctg gtg tcc tgt gcc tac cag gtg gcc cgg ggc atg gag        1824
Phe Lys Asp Leu Val Ser Cys Ala Tyr Gln Val Ala Arg Gly Met Glu
        595                 600                 605 tac ttg gcc tcc cag aag tgc atc cac agg gac ctg gct gcc cgc aat        1872
Tyr Leu Ala Ser Gln Lys Cys Ile His Arg Asp Leu Ala Ala Arg Asn
610                 615                 620 gtg ctg gtg acc gag gac aac gtg atg aag atc gca gac ttc ggg ctg        1920
Val Leu Val Thr Glu Asp Asn Val Met Lys Ile Ala Asp Phe Gly Leu
625                 630                 635                 640 gcc cgg gac gtg cac aac ctc gac tac tac aag aag aca acc aac ggc        1968
Ala Arg Asp Val His Asn Leu Asp Tyr Tyr Lys Lys Thr Thr Asn Gly
                645                 650                 655 cgg ctg ccc gtg aag tgg atg gcg cct gag gcc ttg ttt gac cga gtc        2016
Arg Leu Pro Val Lys Trp Met Ala Pro Glu Ala Leu Phe Asp Arg Val
            660                 665                 670 tac act cac cag agt gac gtc tgg tcc ttt ggg gtc ctg ctc tgg gag        2064
Tyr Thr His Gln Ser Asp Val Trp Ser Phe Gly Val Leu Leu Trp Glu
        675                 680                 685 atc ttc acg ctg ggg ggc tcc ccg tac ccc ggc atc cct gtg gag gag        2112
Ile Phe Thr Leu Gly Gly Ser Pro Tyr Pro Gly Ile Pro Val Glu Glu
690                 695                 700 ctc ttc aag ctg ctg aag gag ggc cac cgc atg gac aag ccc gcc aac        2160
Leu Phe Lys Leu Leu Lys Glu Gly His Arg Met Asp Lys Pro Ala Asn
705                 710                 715                 720 tgc aca cac gac ctg tac atg atc atg cgg gag tgc tgg cat gcc gcg        2208
Cys Thr His Asp Leu Tyr Met Ile Met Arg Glu Cys Trp His Ala Ala
                725                 730                 735 ccc tcc cag agg ccc acc ttc aag cag ctg gtg gag gac ctg gac cgt        2256
Pro Ser Gln Arg Pro Thr Phe Lys Gln Leu Val Glu Asp Leu Asp Arg
            740                 745                 750 gtc ctt acc gtg acg tcc acc gac gag tac ctg gac ctg tcg gcg cct        2304
Val Leu Thr Val Thr Ser Thr Asp Glu Tyr Leu Asp Leu Ser Ala Pro
        755                 760                 765 ttc gag cag tac tcc ccg ggt ggc cag gac acc ccc agc tcc agc tcc        2352
Phe Glu Gln Tyr Ser Pro Gly Gly Gln Asp Thr Pro Ser Ser Ser Ser
770                 775                 780 tca ggg gac gac tcc gag gtc ctg gga ggg tca gtc tgg ccc gcc tgc        2400
Ser Gly Asp Asp Ser Glu Val Leu Gly Gly Ser Val Trp Pro Ala Cys
785                 790                 795                 800 ctg ctg act tgg gtg tgg cct gag cag gta aag gcg aca cag gag gag        2448
Leu Leu Thr Trp Val Trp Pro Glu Gln Val Lys Ala Thr Gln Glu Glu
                805                 810                 815 aac cgg gag ctg agg agc agg tgt gag gag ctc cac ggg aag aac ctg        2496
Asn Arg Glu Leu Arg Ser Arg Cys Glu Glu Leu His Gly Lys Asn Leu
            820                 825                 830 gaa ctg ggg aag atc atg gac agg ttc gaa gag gtt gtg tac cag gcc        2544
Glu Leu Gly Lys Ile Met Asp Arg Phe Glu Glu Val Val Tyr Gln Ala
        835                 840                 845 atg gag gaa gtt cag aag cag aag gaa ctt tcc aaa gct gaa atc cag        2592
Met Glu Glu Val Gln Lys Gln Lys Glu Leu Ser Lys Ala Glu Ile Gln
850                 855                 860 aaa gtt cta aaa gaa aaa gac caa ctt acc aca gat ctg aac tcc atg        2640
Lys Val Leu Lys Glu Lys Asp Gln Leu Thr Thr Asp Leu Asn Ser Met
865                 870                 875                 880 gag aag tcc ttc tcc gac ctc ttc aag cgt ttt gag aaa cag aaa gag        2688
Glu Lys Ser Phe Ser Asp Leu Phe Lys Arg Phe Glu Lys Gln Lys Glu
                885                 890                 895
```

-continued

```
gtg atc gag ggc tac cgc aag aac gaa gag tca ctg aag aag tgc gtg      2736
Val Ile Glu Gly Tyr Arg Lys Asn Glu Glu Ser Leu Lys Lys Cys Val
                900                 905                 910 gag gat tac ctg gca agg atc acc cag gag ggc cag agg tac caa gcc      2784
Glu Asp Tyr Leu Ala Arg Ile Thr Gln Glu Gly Gln Arg Tyr Gln Ala
    915                 920                 925 ctg aag gcc cac gcg gag gag aag ctg cag ctg gca aac gag gag atc      2832
Leu Lys Ala His Ala Glu Glu Lys Leu Gln Leu Ala Asn Glu Glu Ile
930                 935                 940 gcc cag gtc cgg agc aag gcc cag gcg gaa gcg ttg gcc ctc cag gcc      2880
Ala Gln Val Arg Ser Lys Ala Gln Ala Glu Ala Leu Ala Leu Gln Ala
945                 950                 955                 960 agc ctg agg aag gag cag atg cgc atc cag tcg ctg gag aag aca gtg      2928
Ser Leu Arg Lys Glu Gln Met Arg Ile Gln Ser Leu Glu Lys Thr Val
                965                 970                 975 gag cag aag act aaa gag aac gag gag ctg acc agg atc tgc gac gac      2976
Glu Gln Lys Thr Lys Glu Asn Glu Glu Leu Thr Arg Ile Cys Asp Asp
    980                 985                 990 ctc atc tcc aag atg gag aag atc tga                                   3003
Leu Ile Ser Lys Met Glu Lys Ile
        995                 1000

<210> SEQ ID NO 6
<211> LENGTH: 1000
<212> TYPE: PRT
<213> ORGANISM: Homo sapiens

<400> SEQUENCE: 6

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
                20                  25                  30

Gly Arg Ala Ala Glu Val Pro Gly Pro Glu Pro Gly Gln Gln Glu Gln
            35                  40                  45

Leu Val Phe Gly Ser Gly Asp Ala Val Glu Leu Ser Cys Pro Pro Pro
        50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
```

```
                225                 230                 235                 240
Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
                260                 265                 270

Phe His Cys Lys Val Tyr Ser Asp Ala Gln Pro His Ile Gln Trp Leu
                275                 280                 285

Lys His Val Glu Val Asn Gly Ser Lys Val Gly Pro Asp Gly Thr Pro
                290                 295                 300

Tyr Val Thr Val Leu Lys Ser Trp Ile Ser Glu Ser Val Glu Ala Asp
305                 310                 315                 320

Val Arg Leu Arg Leu Ala Asn Val Ser Glu Arg Asp Gly Gly Glu Tyr
                325                 330                 335

Leu Cys Arg Ala Thr Asn Phe Ile Gly Val Ala Glu Lys Ala Phe Trp
                340                 345                 350

Leu Ser Val His Gly Pro Arg Ala Ala Glu Glu Glu Leu Val Glu Ala
                355                 360                 365

Asp Glu Ala Gly Ser Val Tyr Ala Gly Ile Leu Ser Tyr Gly Val Gly
                370                 375                 380

Phe Phe Leu Phe Ile Leu Val Val Ala Ala Val Thr Leu Cys Arg Leu
385                 390                 395                 400

Arg Ser Pro Pro Lys Lys Gly Leu Gly Ser Pro Thr Val His Lys Ile
                405                 410                 415

Ser Arg Phe Pro Leu Lys Arg Gln Val Ser Leu Glu Ser Asn Ala Ser
                420                 425                 430

Met Ser Ser Asn Thr Pro Leu Val Arg Ile Ala Arg Leu Ser Ser Gly
                435                 440                 445

Glu Gly Pro Thr Leu Ala Asn Val Ser Glu Leu Glu Leu Pro Ala Asp
                450                 455                 460

Pro Lys Trp Glu Leu Ser Arg Ala Arg Leu Thr Leu Gly Lys Pro Leu
465                 470                 475                 480

Gly Glu Gly Cys Phe Gly Gln Val Val Met Ala Glu Ala Ile Gly Ile
                485                 490                 495

Asp Lys Asp Arg Ala Ala Lys Pro Val Thr Val Ala Val Lys Met Leu
                500                 505                 510

Lys Asp Asp Ala Thr Asp Lys Asp Leu Ser Asp Leu Val Ser Glu Met
                515                 520                 525

Glu Met Met Lys Met Ile Gly Lys His Lys Asn Ile Ile Asn Leu Leu
                530                 535                 540

Gly Ala Cys Thr Gln Gly Gly Pro Leu Tyr Val Leu Val Glu Tyr Ala
545                 550                 555                 560

Ala Lys Gly Asn Leu Arg Glu Phe Leu Arg Ala Arg Arg Pro Pro Gly
                565                 570                 575

Leu Asp Tyr Ser Phe Asp Thr Cys Lys Pro Pro Glu Glu Gln Leu Thr
                580                 585                 590

Phe Lys Asp Leu Val Ser Cys Ala Tyr Gln Val Ala Arg Gly Met Glu
                595                 600                 605

Tyr Leu Ala Ser Gln Lys Cys Ile His Arg Asp Leu Ala Ala Arg Asn
                610                 615                 620

Val Leu Val Thr Glu Asp Asn Val Met Lys Ile Ala Asp Phe Gly Leu
625                 630                 635                 640

Ala Arg Asp Val His Asn Leu Asp Tyr Tyr Lys Lys Thr Thr Asn Gly
                645                 650                 655
```

Arg Leu Pro Val Lys Trp Met Ala Pro Glu Ala Leu Phe Asp Arg Val
            660                 665                 670

Tyr Thr His Gln Ser Asp Val Trp Ser Phe Gly Val Leu Leu Trp Glu
        675                 680                 685

Ile Phe Thr Leu Gly Gly Ser Pro Tyr Pro Gly Ile Pro Val Glu Glu
690                 695                 700

Leu Phe Lys Leu Leu Lys Glu Gly His Arg Met Asp Lys Pro Ala Asn
705                 710                 715                 720

Cys Thr His Asp Leu Tyr Met Ile Met Arg Glu Cys Trp His Ala Ala
                725                 730                 735

Pro Ser Gln Arg Pro Thr Phe Lys Gln Leu Val Glu Asp Leu Asp Arg
            740                 745                 750

Val Leu Thr Val Thr Ser Thr Asp Glu Tyr Leu Asp Leu Ser Ala Pro
        755                 760                 765

Phe Glu Gln Tyr Ser Pro Gly Gly Gln Asp Thr Pro Ser Ser Ser Ser
770                 775                 780

Ser Gly Asp Asp Ser Glu Val Leu Gly Gly Ser Val Trp Pro Ala Cys
785                 790                 795                 800

Leu Leu Thr Trp Val Trp Pro Glu Gln Val Lys Ala Thr Gln Glu Glu
                805                 810                 815

Asn Arg Glu Leu Arg Ser Arg Cys Glu Glu Leu His Gly Lys Asn Leu
            820                 825                 830

Glu Leu Gly Lys Ile Met Asp Arg Phe Glu Glu Val Val Tyr Gln Ala
        835                 840                 845

Met Glu Glu Val Gln Lys Gln Lys Glu Leu Ser Lys Ala Glu Ile Gln
850                 855                 860

Lys Val Leu Lys Glu Lys Asp Gln Leu Thr Thr Asp Leu Asn Ser Met
865                 870                 875                 880

Glu Lys Ser Phe Ser Asp Leu Phe Lys Arg Phe Glu Lys Gln Lys Glu
                885                 890                 895

Val Ile Glu Gly Tyr Arg Lys Asn Glu Glu Ser Leu Lys Lys Cys Val
            900                 905                 910

Glu Asp Tyr Leu Ala Arg Ile Thr Gln Glu Gly Gln Arg Tyr Gln Ala
        915                 920                 925

Leu Lys Ala His Ala Glu Glu Lys Leu Gln Leu Ala Asn Glu Glu Ile
930                 935                 940

Ala Gln Val Arg Ser Lys Ala Gln Ala Glu Ala Leu Ala Leu Gln Ala
945                 950                 955                 960

Ser Leu Arg Lys Glu Gln Met Arg Ile Gln Ser Leu Glu Lys Thr Val
                965                 970                 975

Glu Gln Lys Thr Lys Glu Asn Glu Glu Leu Thr Arg Ile Cys Asp Asp
            980                 985                 990

Leu Ile Ser Lys Met Glu Lys Ile
        995                 1000

<210> SEQ ID NO 7
<211> LENGTH: 20
<212> TYPE: DNA
<213> ORGANISM: Homo sapiens

<400> SEQUENCE: 7
cctggactac tccttcgaca                                                  20

<210> SEQ ID NO 8

```
<211> LENGTH: 23
<212> TYPE: DNA
<213> ORGANISM: Homo sapiens

<400> SEQUENCE: 8
tcttctccat cttggagatg agg                                              23

<210> SEQ ID NO 9
<211> LENGTH: 23
<212> TYPE: DNA
<213> ORGANISM: Homo sapiens

<400> SEQUENCE: 9
tgtttgaccg agtctacact cac                                              23

<210> SEQ ID NO 10
<211> LENGTH: 24
<212> TYPE: DNA
<213> ORGANISM: Homo sapiens

<400> SEQUENCE: 10
ttctccatgg agttcagatc tgtg                                             24

<210> SEQ ID NO 11
<211> LENGTH: 20
<212> TYPE: DNA
<213> ORGANISM: Homo sapiens

<400> SEQUENCE: 11
tcctgctctg ccggtcgcac                                                  20

<210> SEQ ID NO 12
<211> LENGTH: 20
<212> TYPE: DNA
<213> ORGANISM: Homo sapiens

<400> SEQUENCE: 12
cagcggctcc gtggaggtca                                                  20

<210> SEQ ID NO 13
<211> LENGTH: 27
<212> TYPE: DNA
<213> ORGANISM: Artificial
<220> FEATURE:
<223> OTHER INFORMATION: Description of Artificial Sequence: an
      artificially synthesized primer sequence

<400> SEQUENCE: 13
ggatccgcca ccatgggcgc ccctgcc                                          27

<210> SEQ ID NO 14
<211> LENGTH: 26
<212> TYPE: DNA
<213> ORGANISM: Artificial
<220> FEATURE:
<223> OTHER INFORMATION: Description of Artificial Sequence: an
      artificially synthesized primer sequence

<400> SEQUENCE: 14
gaattctcag atcttctcca tcttgg                                           26

<210> SEQ ID NO 15
<211> LENGTH: 20
<212> TYPE: DNA
<213> ORGANISM: Homo sapiens
```

```
<400> SEQUENCE: 15
ggacctggac cgtgtcctta                                              20

<210> SEQ ID NO 16
<211> LENGTH: 20
<212> TYPE: DNA
<213> ORGANISM: Homo sapiens

<400> SEQUENCE: 16
tctcctcctg tgtcgccttt                                              20

<210> SEQ ID NO 17
<211> LENGTH: 17
<212> TYPE: DNA
<213> ORGANISM: Homo sapiens

<400> SEQUENCE: 17
ctggaccgtg tccttac                                                 17

<210> SEQ ID NO 18
<211> LENGTH: 17
<212> TYPE: DNA
<213> ORGANISM: Homo sapiens

<400> SEQUENCE: 18
ccttctggct gtactgg                                                 17

<210> SEQ ID NO 19
<211> LENGTH: 17
<212> TYPE: DNA
<213> ORGANISM: Homo sapiens

<400> SEQUENCE: 19
ctttcgagca gtactcc                                                 17

<210> SEQ ID NO 20
<211> LENGTH: 20
<212> TYPE: DNA
<213> ORGANISM: Homo sapiens

<400> SEQUENCE: 20
aggccacacc caagtcagca                                              20

<210> SEQ ID NO 21
<211> LENGTH: 60
<212> TYPE: DNA
<213> ORGANISM: Artificial
<220> FEATURE:
<223> OTHER INFORMATION: Description of Artificial Sequence: an
      artificially synthesized primer sequence

<400> SEQUENCE: 21
ggatccgcca ccatggacta caaggacgac gatgacaagg gcgcccctgc ctgcgccctc   60

<210> SEQ ID NO 22
<211> LENGTH: 27
<212> TYPE: DNA
<213> ORGANISM: Artificial
<220> FEATURE:
<223> OTHER INFORMATION: Description of Artificial Sequence: an
      artificially synthesized FLAG tag sequence

<400> SEQUENCE: 22
```

```
atggactaca aggacgacga tgacaag                                              27
```

<210> SEQ ID NO 23
<211> LENGTH: 27
<212> TYPE: DNA
<213> ORGANISM: Homo sapiens

<400> SEQUENCE: 23

```
cctgaggacg ccgcggcccc cgccccc                                              27
```

<210> SEQ ID NO 24
<211> LENGTH: 27
<212> TYPE: DNA
<213> ORGANISM: Homo sapiens

<400> SEQUENCE: 24

```
gcggggacag cggctccgtg gaggtca                                              27
```

<210> SEQ ID NO 25
<211> LENGTH: 3144
<212> TYPE: DNA
<213> ORGANISM: Homo sapiens
<220> FEATURE:
<221> NAME/KEY: CDS
<222> LOCATION: (1)..(3144)

<400> SEQUENCE: 25

```
atg ggc gcc cct gcc tgc gcc ctc gcg ctc tgc gtg gcc gtg gcc atc      48
Met Gly Ala Pro Ala Cys Ala Leu Ala Leu Cys Val Ala Val Ala Ile
1               5                   10                  15 gtg gcc ggc gcc tcc tcg gag tcc ttg ggg acg gag cag cgc gtc gtg      96
Val Ala Gly Ala Ser Ser Glu Ser Leu Gly Thr Glu Gln Arg Val Val
            20                  25                  30 ggg cga gcg gca gaa gtc ccg ggc cca gag ccc ggc cag cag gag cag     144
Gly Arg Ala Ala Glu Val Pro Gly Pro Glu Pro Gly Gln Gln Glu Gln
        35                  40                  45 ttg gtc ttc ggc agc ggg gat gct gtg gag ctg agc tgt ccc ccg ccc     192
Leu Val Phe Gly Ser Gly Asp Ala Val Glu Leu Ser Cys Pro Pro Pro
    50                  55                  60 ggg ggt ggt ccc atg ggg ccc act gtc tgg gtc aag gat ggc aca ggg     240
Gly Gly Gly Pro Met Gly Pro Thr Val Trp Val Lys Asp Gly Thr Gly
65                  70                  75                  80 ctg gtg ccc tcg gag cgt gtc ctg gtg ggg ccc cag cgg ctg cag gtg     288
Leu Val Pro Ser Glu Arg Val Leu Val Gly Pro Gln Arg Leu Gln Val
                85                  90                  95 ctg aat gcc tcc cac gag gac tcc ggg gcc tac agc tgc cgg cag cgg     336
Leu Asn Ala Ser His Glu Asp Ser Gly Ala Tyr Ser Cys Arg Gln Arg
            100                 105                 110 ctc acg cag cgc gta ctg tgc cac ttc agt gtg cgg gtg aca gac gct     384
Leu Thr Gln Arg Val Leu Cys His Phe Ser Val Arg Val Thr Asp Ala
        115                 120                 125 cca tcc tcg gga gat gac gaa gac ggg gag gac gag gct gag gac aca     432
Pro Ser Ser Gly Asp Asp Glu Asp Gly Glu Asp Glu Ala Glu Asp Thr
    130                 135                 140 ggt gtg gac aca ggg gcc cct tac tgg aca cgg ccc gag cgg atg gac     480
Gly Val Asp Thr Gly Ala Pro Tyr Trp Thr Arg Pro Glu Arg Met Asp
145                 150                 155                 160 aag aag ctg ctg gcc gtg ccg gcc gcc aac acc gtc cgc ttc cgc tgc     528
Lys Lys Leu Leu Ala Val Pro Ala Ala Asn Thr Val Arg Phe Arg Cys
                165                 170                 175 cca gcc gct ggc aac ccc act ccc tcc atc tcc tgg ctg aag aac ggc     576
Pro Ala Ala Gly Asn Pro Thr Pro Ser Ile Ser Trp Leu Lys Asn Gly
```

180                 185                 190
agg gag ttc cgc ggc gag cac cgc att gga ggc atc aag ctg cgg cat         624
Arg Glu Phe Arg Gly Glu His Arg Ile Gly Gly Ile Lys Leu Arg His
            195                 200                 205 cag cag tgg agc ctg gtc atg gaa agc gtg gtg ccc tcg gac cgc ggc         672
Gln Gln Trp Ser Leu Val Met Glu Ser Val Val Pro Ser Asp Arg Gly
    210                 215                 220 aac tac acc tgc gtc gtg gag aac aag ttt ggc agc atc cgg cag acg         720
Asn Tyr Thr Cys Val Val Glu Asn Lys Phe Gly Ser Ile Arg Gln Thr
225                 230                 235                 240 tac acg ctg gac gtg ctg gag cgc tcc ccg cac cgg ccc atc ctg cag         768
Tyr Thr Leu Asp Val Leu Glu Arg Ser Pro His Arg Pro Ile Leu Gln
                245                 250                 255 gcg ggg ctg ccg gcc aac cag acg gcg gtg ctg ggc agc gac gtg gag         816
Ala Gly Leu Pro Ala Asn Gln Thr Ala Val Leu Gly Ser Asp Val Glu
            260                 265                 270 ttc cac tgc aag gtg tac agt gac gca cag ccc cac atc cag tgg ctc         864
Phe His Cys Lys Val Tyr Ser Asp Ala Gln Pro His Ile Gln Trp Leu
    275                 280                 285 aag cac gtg gag gtg aat ggc agc aag gtg ggc ccg gac ggc aca ccc         912
Lys His Val Glu Val Asn Gly Ser Lys Val Gly Pro Asp Gly Thr Pro
290                 295                 300 tac gtt acc gtg ctc aag tcc tgg atc agt gag agt gtg gag gcc gac         960
Tyr Val Thr Val Leu Lys Ser Trp Ile Ser Glu Ser Val Glu Ala Asp
305                 310                 315                 320 gtg cgc ctc cgc ctg gcc aat gtg tcg gag cgg gac ggg ggc gag tac        1008
Val Arg Leu Arg Leu Ala Asn Val Ser Glu Arg Asp Gly Gly Glu Tyr
                325                 330                 335 ctc tgt cga gcc acc aat ttc ata ggc gtg gcc gag aag gcc ttt tgg        1056
Leu Cys Arg Ala Thr Asn Phe Ile Gly Val Ala Glu Lys Ala Phe Trp
            340                 345                 350 ctg agc gtt cac ggg ccc cga gca gcc gag gag gag ctg gtg gag gct        1104
Leu Ser Val His Gly Pro Arg Ala Ala Glu Glu Glu Leu Val Glu Ala
    355                 360                 365 gac gag gcg ggc agt gtg tat gca ggc atc ctc agc tac ggg gtg ggc        1152
Asp Glu Ala Gly Ser Val Tyr Ala Gly Ile Leu Ser Tyr Gly Val Gly
370                 375                 380 ttc ttc ctg ttc atc ctg gtg gtg gcg gct gtg acg ctc tgc cgc ctg        1200
Phe Phe Leu Phe Ile Leu Val Val Ala Ala Val Thr Leu Cys Arg Leu
385                 390                 395                 400 cgc agc ccc ccc aag aaa ggc ctg ggc tcc ccc acc gtg cac aag atc        1248
Arg Ser Pro Pro Lys Lys Gly Leu Gly Ser Pro Thr Val His Lys Ile
                405                 410                 415 tcc cgc ttc ccg ctc aag cga cag gtg tcc ctg gag tcc aac gcg tcc        1296
Ser Arg Phe Pro Leu Lys Arg Gln Val Ser Leu Glu Ser Asn Ala Ser
            420                 425                 430 atg agc tcc aac aca cca ctg gtg cgc atc gca agg ctg tcc tca ggg        1344
Met Ser Ser Asn Thr Pro Leu Val Arg Ile Ala Arg Leu Ser Ser Gly
    435                 440                 445 gag ggc ccc acg ctg gcc aat gtc tcc gag ctc gag ctg cct gcc gac        1392
Glu Gly Pro Thr Leu Ala Asn Val Ser Glu Leu Glu Leu Pro Ala Asp
450                 455                 460 ccc aaa tgg gag ctg tct cgg gcc cgg ctg acc ctg ggc aag ccc ctt        1440
Pro Lys Trp Glu Leu Ser Arg Ala Arg Leu Thr Leu Gly Lys Pro Leu
465                 470                 475                 480 ggg gag ggc tgc ttc ggc cag gtg gtc atg gcg gag gcc atc ggc att        1488
Gly Glu Gly Cys Phe Gly Gln Val Val Met Ala Glu Ala Ile Gly Ile
                485                 490                 495 gac aag gac cgg gcc gcc aag cct gtc acc gta gcc gtg aag atg ctg        1536

```
                     Asp Lys Asp Arg Ala Ala Lys Pro Val Thr Val Ala Val Lys Met Leu
                                 500                 505                 510 aaa gac gat gcc act gac aag gac ctg tcg gac ctg gtg tct gag atg                       1584
Lys Asp Asp Ala Thr Asp Lys Asp Leu Ser Asp Leu Val Ser Glu Met
            515                 520                 525 gag atg atg aag atg atc ggg aaa cac aaa aac atc atc aac ctg ctg                       1632
Glu Met Met Lys Met Ile Gly Lys His Lys Asn Ile Ile Asn Leu Leu
        530                 535                 540 ggc gcc tgc acg cag ggc ggg ccc ctg tac gtg ctg gtg gag tac gcg                       1680
Gly Ala Cys Thr Gln Gly Gly Pro Leu Tyr Val Leu Val Glu Tyr Ala
545                 550                 555                 560 gcc aag ggt aac ctg cgg gag ttt ctg cgg gcg cgg cgg ccc cgg ggc                       1728
Ala Lys Gly Asn Leu Arg Glu Phe Leu Arg Ala Arg Arg Pro Arg Gly
                565                 570                 575 ctg gac tac tcc ttc gac acc tgc aag ccg ccc gag gag cag ctc acc                       1776
Leu Asp Tyr Ser Phe Asp Thr Cys Lys Pro Pro Glu Glu Gln Leu Thr
            580                 585                 590 ttc aag gac ctg gtg tcc tgt gcc tac cag gtg gcc cgg ggc atg gag                       1824
Phe Lys Asp Leu Val Ser Cys Ala Tyr Gln Val Ala Arg Gly Met Glu
        595                 600                 605 tac ttg gcc tcc cag aag tgc atc cac agg gac ctg gct gcc cgc aat                       1872
Tyr Leu Ala Ser Gln Lys Cys Ile His Arg Asp Leu Ala Ala Arg Asn
610                 615                 620 gtg ctg gtg acc gag gac aac gtg atg aag atc gca gac ttc ggg ctg                       1920
Val Leu Val Thr Glu Asp Asn Val Met Lys Ile Ala Asp Phe Gly Leu
625                 630                 635                 640 gcc cgg gac gtg cac aac ctc gac tac tac aag aag aca acc aac ggc                       1968
Ala Arg Asp Val His Asn Leu Asp Tyr Tyr Lys Lys Thr Thr Asn Gly
                645                 650                 655 cgg ctg ccc gtg aag tgg atg gcg cct gag gcc ttg ttt gac cga gtc                       2016
Arg Leu Pro Val Lys Trp Met Ala Pro Glu Ala Leu Phe Asp Arg Val
            660                 665                 670 tac act cac cag agt gac gtc tgg tcc ttt ggg gtc ctg ctc tgg gag                       2064
Tyr Thr His Gln Ser Asp Val Trp Ser Phe Gly Val Leu Leu Trp Glu
        675                 680                 685 atc ttc acg ctg ggg ggc tcc ccg tac ccc ggc atc cct gtg gag gag                       2112
Ile Phe Thr Leu Gly Gly Ser Pro Tyr Pro Gly Ile Pro Val Glu Glu
690                 695                 700 ctc ttc aag ctg ctg aag gag ggc cac cgc atg gac aag ccc gcc aac                       2160
Leu Phe Lys Leu Leu Lys Glu Gly His Arg Met Asp Lys Pro Ala Asn
705                 710                 715                 720 tgc aca cac gac ctg tac atg atc atg cgg gag tgc tgg cat gcc gcg                       2208
Cys Thr His Asp Leu Tyr Met Ile Met Arg Glu Cys Trp His Ala Ala
                725                 730                 735 ccc tcc cag agg ccc acc ttc aag cag ctg gtg gat tac ctg gag cag                       2256
Pro Ser Gln Arg Pro Thr Phe Lys Gln Leu Val Asp Tyr Leu Glu Gln
            740                 745                 750 ttt gga act tcc tcg ttt aag gag tcg gcc ttg agg aag cag tcc tta                       2304
Phe Gly Thr Ser Ser Phe Lys Glu Ser Ala Leu Arg Lys Gln Ser Leu
        755                 760                 765 tac ctc aag ttt gac ccc ctc ctg agg gac agt cct ggt aga cca gtg                       2352
Tyr Leu Lys Phe Asp Pro Leu Leu Arg Asp Ser Pro Gly Arg Pro Val
770                 775                 780 ccc gtg gcc acc gag acc agc agc atg cac ggt gca aat gag act ccc                       2400
Pro Val Ala Thr Glu Thr Ser Ser Met His Gly Ala Asn Glu Thr Pro
785                 790                 795                 800 tca gga cgt ccg cgg gaa gcc aag ctt gtg gag ttc gat ttc ttg gga                       2448
Ser Gly Arg Pro Arg Glu Ala Lys Leu Val Glu Phe Asp Phe Leu Gly
                805                 810                 815
```

```
gca ctg gac att cct gtg cca ggc cca ccc cca ggt gtt ccc gcg cct      2496
Ala Leu Asp Ile Pro Val Pro Gly Pro Pro Pro Gly Val Pro Ala Pro
            820                 825                 830 ggg ggc cca ccc ctg tcc acc gga cct ata gtg gac ctg ctc cag tac      2544
Gly Gly Pro Pro Leu Ser Thr Gly Pro Ile Val Asp Leu Leu Gln Tyr
835                 840                 845 agc cag aag gac ctg gat gca gtg gta aag gcg aca cag gag gag aac      2592
Ser Gln Lys Asp Leu Asp Ala Val Val Lys Ala Thr Gln Glu Glu Asn
    850                 855                 860 cgg gag ctg agg agc agg tgt gag gag ctc cac ggg aag aac ctg gaa      2640
Arg Glu Leu Arg Ser Arg Cys Glu Glu Leu His Gly Lys Asn Leu Glu
865                 870                 875                 880 ctg ggg aag atc atg gac agg ttc gaa gag gtt gtg tac cag gcc atg      2688
Leu Gly Lys Ile Met Asp Arg Phe Glu Glu Val Val Tyr Gln Ala Met
                885                 890                 895 gag gaa gtt cag aag cag aag gaa ctt tcc aaa gct gaa atc cag aaa      2736
Glu Glu Val Gln Lys Gln Lys Glu Leu Ser Lys Ala Glu Ile Gln Lys
            900                 905                 910 gtt cta aaa gaa aaa gac caa ctt acc aca gat ctg aac tcc atg gag      2784
Val Leu Lys Glu Lys Asp Gln Leu Thr Thr Asp Leu Asn Ser Met Glu
        915                 920                 925 aag tcc ttc tcc gac ctc ttc aag cgt ttt gag aaa cag aaa gag gtg      2832
Lys Ser Phe Ser Asp Leu Phe Lys Arg Phe Glu Lys Gln Lys Glu Val
930                 935                 940 atc gag ggc tac cgc aag aac gaa gag tca ctg aag aag tgc gtg gag      2880
Ile Glu Gly Tyr Arg Lys Asn Glu Glu Ser Leu Lys Lys Cys Val Glu
945                 950                 955                 960 gat tac ctg gca agg atc acc cag gag ggc cag agg tac caa gcc ctg      2928
Asp Tyr Leu Ala Arg Ile Thr Gln Glu Gly Gln Arg Tyr Gln Ala Leu
                965                 970                 975 aag gcc cac gcg gag gag aag ctg cag ctg gca aac gag gag atc gct      2976
Lys Ala His Ala Glu Glu Lys Leu Gln Leu Ala Asn Glu Glu Ile Ala
            980                 985                 990 cag gtc cgg agc aag gcc cag gcg gaa gcg ttg gcc ctc cag gcc agc      3024
Gln Val Arg Ser Lys Ala Gln Ala Glu Ala Leu Ala Leu Gln Ala Ser
        995                 1000                1005 ctg agg aag gag cag atg cgc atc cag tcg ctg gag aag aca gtg           3069
Leu Arg Lys Glu Gln Met Arg Ile Gln Ser Leu Glu Lys Thr Val
    1010                1015                1020 gag cag aag act aaa gag aac gag gag ctg acc agg atc tgc gac           3114
Glu Gln Lys Thr Lys Glu Asn Glu Glu Leu Thr Arg Ile Cys Asp
1025                1030                1035 gac ctc atc tcc aag atg gag aag atc tga                              3144
Asp Leu Ile Ser Lys Met Glu Lys Ile
    1040                1045

<210> SEQ ID NO 26
<211> LENGTH: 1047
<212> TYPE: PRT
<213> ORGANISM: Homo sapiens

<400> SEQUENCE: 26

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60
```

-continued

Gly Gly Gly Pro Met Gly Pro Thr Val Trp Val Lys Asp Gly Thr Gly
65              70                  75                  80

Leu Val Pro Ser Glu Arg Val Leu Val Gly Pro Gln Arg Leu Gln Val
            85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
            115                 120                 125

Pro Ser Ser Gly Asp Asp Glu Asp Gly Glu Asp Glu Ala Glu Asp Thr
            130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
                180                 185                 190

Arg Glu Phe Arg Gly Glu His Arg Ile Gly Gly Ile Lys Leu Arg His
            195                 200                 205

Gln Gln Trp Ser Leu Val Met Glu Ser Val Val Pro Ser Asp Arg Gly
210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
            245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
            275                 280                 285

Lys His Val Glu Val Asn Gly Ser Lys Val Gly Pro Asp Gly Thr Pro
            290                 295                 300

Tyr Val Thr Val Leu Lys Ser Trp Ile Ser Glu Ser Val Glu Ala Asp
305                 310                 315                 320

Val Arg Leu Arg Leu Ala Asn Val Ser Glu Arg Asp Gly Gly Glu Tyr
            325                 330                 335

Leu Cys Arg Ala Thr Asn Phe Ile Gly Val Ala Glu Lys Ala Phe Trp
            340                 345                 350

Leu Ser Val His Gly Pro Arg Ala Ala Glu Glu Leu Val Glu Ala
            355                 360                 365

Asp Glu Ala Gly Ser Val Tyr Ala Gly Ile Leu Ser Tyr Gly Val Gly
            370                 375                 380

Phe Phe Leu Phe Ile Leu Val Val Ala Ala Val Thr Leu Cys Arg Leu
385                 390                 395                 400

Arg Ser Pro Pro Lys Lys Gly Leu Gly Ser Pro Thr Val His Lys Ile
            405                 410                 415

Ser Arg Phe Pro Leu Lys Arg Gln Val Ser Leu Glu Ser Asn Ala Ser
            420                 425                 430

Met Ser Ser Asn Thr Pro Leu Val Arg Ile Ala Arg Leu Ser Ser Gly
            435                 440                 445

Glu Gly Pro Thr Leu Ala Asn Val Ser Glu Leu Glu Leu Pro Ala Asp
            450                 455                 460

Pro Lys Trp Glu Leu Ser Arg Ala Arg Leu Thr Leu Gly Lys Pro Leu
465                 470                 475                 480

```
Gly Glu Gly Cys Phe Gly Gln Val Val Met Ala Glu Ala Ile Gly Ile
                485                 490                 495
Asp Lys Asp Arg Ala Ala Lys Pro Val Thr Val Ala Val Lys Met Leu
            500                 505                 510
Lys Asp Asp Ala Thr Asp Lys Asp Leu Ser Asp Leu Val Ser Glu Met
            515                 520                 525
Glu Met Met Lys Met Ile Gly Lys His Lys Asn Ile Ile Asn Leu Leu
            530                 535                 540
Gly Ala Cys Thr Gln Gly Gly Pro Leu Tyr Val Leu Val Glu Tyr Ala
545                 550                 555                 560
Ala Lys Gly Asn Leu Arg Glu Phe Leu Arg Ala Arg Arg Pro Arg Gly
                565                 570                 575
Leu Asp Tyr Ser Phe Asp Thr Cys Lys Pro Pro Glu Glu Gln Leu Thr
            580                 585                 590
Phe Lys Asp Leu Val Ser Cys Ala Tyr Gln Val Ala Arg Gly Met Glu
            595                 600                 605
Tyr Leu Ala Ser Gln Lys Cys Ile His Arg Asp Leu Ala Ala Arg Asn
            610                 615                 620
Val Leu Val Thr Glu Asp Asn Val Met Lys Ile Ala Asp Phe Gly Leu
625                 630                 635                 640
Ala Arg Asp Val His Asn Leu Asp Tyr Tyr Lys Lys Thr Thr Asn Gly
                645                 650                 655
Arg Leu Pro Val Lys Trp Met Ala Pro Glu Ala Leu Phe Asp Arg Val
                660                 665                 670
Tyr Thr His Gln Ser Asp Val Trp Ser Phe Gly Val Leu Leu Trp Glu
            675                 680                 685
Ile Phe Thr Leu Gly Gly Ser Pro Tyr Pro Gly Ile Pro Val Glu Glu
            690                 695                 700
Leu Phe Lys Leu Leu Lys Glu Gly His Arg Met Asp Lys Pro Ala Asn
705                 710                 715                 720
Cys Thr His Asp Leu Tyr Met Ile Met Arg Glu Cys Trp His Ala Ala
                725                 730                 735
Pro Ser Gln Arg Pro Thr Phe Lys Gln Leu Val Asp Tyr Leu Glu Gln
            740                 745                 750
Phe Gly Thr Ser Ser Phe Lys Glu Ser Ala Leu Arg Lys Gln Ser Leu
            755                 760                 765
Tyr Leu Lys Phe Asp Pro Leu Leu Arg Asp Ser Pro Gly Arg Pro Val
            770                 775                 780
Pro Val Ala Thr Glu Thr Ser Ser Met His Gly Ala Asn Glu Thr Pro
785                 790                 795                 800
Ser Gly Arg Pro Arg Glu Ala Lys Leu Val Glu Phe Asp Phe Leu Gly
                805                 810                 815
Ala Leu Asp Ile Pro Val Pro Gly Pro Pro Gly Val Pro Ala Pro
            820                 825                 830
Gly Gly Pro Pro Leu Ser Thr Gly Pro Ile Val Asp Leu Leu Gln Tyr
            835                 840                 845
Ser Gln Lys Asp Leu Asp Ala Val Val Lys Ala Thr Gln Glu Glu Asn
            850                 855                 860
Arg Glu Leu Arg Ser Arg Cys Glu Glu Leu His Gly Lys Asn Leu Glu
865                 870                 875                 880
Leu Gly Lys Ile Met Asp Arg Phe Glu Glu Val Tyr Gln Ala Met
                885                 890                 895
Glu Glu Val Gln Lys Gln Lys Glu Leu Ser Lys Ala Glu Ile Gln Lys
```

-continued

```
                900             905             910
Val Leu Lys Glu Lys Asp Gln Leu Thr Thr Asp Leu Asn Ser Met Glu
            915             920             925

Lys Ser Phe Ser Asp Leu Phe Lys Arg Phe Glu Lys Gln Lys Glu Val
        930             935             940

Ile Glu Gly Tyr Arg Lys Asn Glu Glu Ser Leu Lys Lys Cys Val Glu
945             950             955             960

Asp Tyr Leu Ala Arg Ile Thr Gln Glu Gly Gln Arg Tyr Gln Ala Leu
                965             970             975

Lys Ala His Ala Glu Glu Lys Leu Gln Leu Ala Asn Glu Glu Ile Ala
            980             985             990

Gln Val Arg Ser Lys Ala Gln Ala  Glu Ala Leu Ala Leu  Gln Ala Ser
        995             1000            1005

Leu Arg  Lys Glu Gln Met Arg  Ile Gln Ser Leu Glu  Lys Thr Val
    1010            1015            1020

Glu Gln  Lys Thr Lys Glu Asn  Glu Glu Leu Thr Arg  Ile Cys Asp
    1025            1030            1035

Asp Leu  Ile Ser Lys Met Glu  Lys Ile
    1040            1045

<210> SEQ ID NO 27
<211> LENGTH: 3135
<212> TYPE: DNA
<213> ORGANISM: Homo sapiens
<220> FEATURE:
<221> NAME/KEY: CDS
<222> LOCATION: (1)..(3135)

<400> SEQUENCE: 27 atg ggc gcc cct gcc tgc gcc ctc gcg ctc tgc gtg gcc gtg gcc atc    48
Met Gly Ala Pro Ala Cys Ala Leu Ala Leu Cys Val Ala Val Ala Ile
1               5                   10                  15 gtg gcc ggc gcc tcc tcg gag tcc ttg ggg acg gag cag cgc gtc gtg    96
Val Ala Gly Ala Ser Ser Glu Ser Leu Gly Thr Glu Gln Arg Val Val
                20                  25                  30 ggg cga gcg gca gaa gtc ccg ggc cca gag ccc ggc cag cag gag cag   144
Gly Arg Ala Ala Glu Val Pro Gly Pro Glu Pro Gly Gln Gln Glu Gln
            35                  40                  45 ttg gtc ttc ggc agc ggg gat gct gtg gag ctg agc tgt ccc ccg ccc   192
Leu Val Phe Gly Ser Gly Asp Ala Val Glu Leu Ser Cys Pro Pro Pro
        50                  55                  60 ggg ggt ggt ccc atg ggg ccc act gtc tgg gtc aag gat ggc aca ggg   240
Gly Gly Gly Pro Met Gly Pro Thr Val Trp Val Lys Asp Gly Thr Gly
65                  70                  75                  80 ctg gtg ccc tcg gag cgt gtc ctg gtg ggg ccc cag cgg ctg cag gtg   288
Leu Val Pro Ser Glu Arg Val Leu Val Gly Pro Gln Arg Leu Gln Val
                85                  90                  95 ctg aat gcc tcc cac gag gac tcc ggg gcc tac agc tgc cgg cag cgg   336
Leu Asn Ala Ser His Glu Asp Ser Gly Ala Tyr Ser Cys Arg Gln Arg
            100                 105                 110 ctc acg cag cgc gta ctg tgc cac ttc agt gtg cgg gtg aca gac gct   384
Leu Thr Gln Arg Val Leu Cys His Phe Ser Val Arg Val Thr Asp Ala
        115                 120                 125 cca tcc tcg gga gat gac gaa gac ggg gag gac gag gct gag gac aca   432
Pro Ser Ser Gly Asp Asp Glu Asp Gly Glu Asp Glu Ala Glu Asp Thr
    130                 135                 140 ggg gcc cct tac tgg aca cgg ccc gag cgg atg gac aag aag ctg ctg   480
Gly Ala Pro Tyr Trp Thr Arg Pro Glu Arg Met Asp Lys Lys Leu Leu
145                 150                 155                 160
```

| | | | | | | | | | | | | | | | | |
|---|---|---|---|---|---|---|---|---|---|---|---|---|---|---|---|---|
| gcc | gtg | ccg | gcc | gcc | aac | acc | gtc | cgc | ttc | cgc | tgc | cca | gcc | gct | ggc | 528 |
| Ala | Val | Pro | Ala | Ala | Asn | Thr | Val | Arg | Phe | Arg | Cys | Pro | Ala | Ala | Gly | |
| | | | | 165 | | | | 170 | | | | | 175 | | | |
| aac | ccc | act | ccc | tcc | atc | tcc | tgg | ctg | aag | aac | ggc | agg | gag | ttc | cgc | 576 |
| Asn | Pro | Thr | Pro | Ser | Ile | Ser | Trp | Leu | Lys | Asn | Gly | Arg | Glu | Phe | Arg | |
| | | | 180 | | | | | 185 | | | | | 190 | | | |
| ggc | gag | cac | cgc | att | gga | ggc | atc | aag | ctg | cgg | cat | cag | cag | tgg | agc | 624 |
| Gly | Glu | His | Arg | Ile | Gly | Gly | Ile | Lys | Leu | Arg | His | Gln | Gln | Trp | Ser | |
| | | 195 | | | | | 200 | | | | | 205 | | | | |
| ctg | gtc | atg | gaa | agc | gtg | gtg | ccc | tcg | gac | cgc | ggc | aac | tac | acc | tgc | 672 |
| Leu | Val | Met | Glu | Ser | Val | Val | Pro | Ser | Asp | Arg | Gly | Asn | Tyr | Thr | Cys | |
| | 210 | | | | | 215 | | | | | 220 | | | | | |
| gtc | gtg | gag | aac | aag | ttt | ggc | agc | atc | cgg | cag | acg | tac | acg | ctg | gac | 720 |
| Val | Val | Glu | Asn | Lys | Phe | Gly | Ser | Ile | Arg | Gln | Thr | Tyr | Thr | Leu | Asp | |
| 225 | | | | | 230 | | | | | 235 | | | | | 240 | |
| gtg | ctg | gag | cgc | tcc | ccg | cac | cgg | ccc | atc | ctg | cag | gcg | ggg | ctg | ccg | 768 |
| Val | Leu | Glu | Arg | Ser | Pro | His | Arg | Pro | Ile | Leu | Gln | Ala | Gly | Leu | Pro | |
| | | | | 245 | | | | | 250 | | | | | 255 | | |
| gcc | aac | cag | acg | gcg | gtg | ctg | ggc | agc | gac | gtg | gag | ttc | cac | tgc | aag | 816 |
| Ala | Asn | Gln | Thr | Ala | Val | Leu | Gly | Ser | Asp | Val | Glu | Phe | His | Cys | Lys | |
| | | | 260 | | | | | 265 | | | | | 270 | | | |
| gtg | tac | agt | gac | gca | cag | ccc | cac | atc | cag | tgg | ctc | aag | cac | gtg | gag | 864 |
| Val | Tyr | Ser | Asp | Ala | Gln | Pro | His | Ile | Gln | Trp | Leu | Lys | His | Val | Glu | |
| | | 275 | | | | | 280 | | | | | 285 | | | | |
| gtg | aat | ggc | agc | aag | gtg | ggc | ccg | gac | ggc | aca | ccc | tac | gtt | acc | gtg | 912 |
| Val | Asn | Gly | Ser | Lys | Val | Gly | Pro | Asp | Gly | Thr | Pro | Tyr | Val | Thr | Val | |
| | 290 | | | | | 295 | | | | | 300 | | | | | |
| ctc | aag | tcc | tgg | atc | agt | gag | agt | gtg | gag | gcc | gac | gtg | cgc | ctc | cgc | 960 |
| Leu | Lys | Ser | Trp | Ile | Ser | Glu | Ser | Val | Glu | Ala | Asp | Val | Arg | Leu | Arg | |
| 305 | | | | | 310 | | | | | 315 | | | | | 320 | |
| ctg | gcc | aat | gtg | tcg | gag | cgg | gac | ggg | ggc | gag | tac | ctc | tgt | cga | gcc | 1008 |
| Leu | Ala | Asn | Val | Ser | Glu | Arg | Asp | Gly | Gly | Glu | Tyr | Leu | Cys | Arg | Ala | |
| | | | | 325 | | | | | 330 | | | | | 335 | | |
| acc | aat | ttc | ata | ggc | gtg | gcc | gag | aag | gcc | ttt | tgg | ctg | agc | gtt | cac | 1056 |
| Thr | Asn | Phe | Ile | Gly | Val | Ala | Glu | Lys | Ala | Phe | Trp | Leu | Ser | Val | His | |
| | | | 340 | | | | | 345 | | | | | 350 | | | |
| ggg | ccc | cga | gca | gcc | gag | gag | gag | ctg | gtg | gag | gct | gac | gag | gcg | ggc | 1104 |
| Gly | Pro | Arg | Ala | Ala | Glu | Glu | Glu | Leu | Val | Glu | Ala | Asp | Glu | Ala | Gly | |
| | | | 355 | | | | | 360 | | | | | 365 | | | |
| agt | gtg | tat | gca | ggc | atc | ctc | agc | tac | ggg | gtg | ggc | ttc | ttc | ctg | ttc | 1152 |
| Ser | Val | Tyr | Ala | Gly | Ile | Leu | Ser | Tyr | Gly | Val | Gly | Phe | Phe | Leu | Phe | |
| | 370 | | | | | 375 | | | | | 380 | | | | | |
| atc | ctg | gtg | gtg | gcg | gct | gtg | acg | ctc | tgc | cgc | ctg | cgc | agc | ccc | ccc | 1200 |
| Ile | Leu | Val | Val | Ala | Ala | Val | Thr | Leu | Cys | Arg | Leu | Arg | Ser | Pro | Pro | |
| 385 | | | | | 390 | | | | | 395 | | | | | 400 | |
| aag | aaa | ggc | ctg | ggc | tcc | ccc | acc | gtg | cac | aag | atc | tcc | cgc | ttc | ccg | 1248 |
| Lys | Lys | Gly | Leu | Gly | Ser | Pro | Thr | Val | His | Lys | Ile | Ser | Arg | Phe | Pro | |
| | | | | 405 | | | | | 410 | | | | | 415 | | |
| ctc | aag | cga | cag | cag | gtg | tcc | ctg | gag | tcc | aac | gcg | tcc | atg | agc | tcc | 1296 |
| Leu | Lys | Arg | Gln | Gln | Val | Ser | Leu | Glu | Ser | Asn | Ala | Ser | Met | Ser | Ser | |
| | | | 420 | | | | | 425 | | | | | 430 | | | |
| aac | aca | cca | ctg | gtg | cgc | atc | gca | agg | ctg | tcc | tca | ggg | gag | ggc | ccc | 1344 |
| Asn | Thr | Pro | Leu | Val | Arg | Ile | Ala | Arg | Leu | Ser | Ser | Gly | Glu | Gly | Pro | |
| | | 435 | | | | | 440 | | | | | 445 | | | | |
| acg | ctg | gcc | aat | gtc | tcc | gag | ctc | gag | ctg | cct | gcc | gac | ccc | aaa | tgg | 1392 |
| Thr | Leu | Ala | Asn | Val | Ser | Glu | Leu | Glu | Leu | Pro | Ala | Asp | Pro | Lys | Trp | |
| | 450 | | | | | 455 | | | | | 460 | | | | | |
| gag | ctg | tct | cgg | gcc | cgg | ctg | acc | ctg | ggc | aag | ccc | ctt | ggg | gag | ggc | 1440 |
| Glu | Leu | Ser | Arg | Ala | Arg | Leu | Thr | Leu | Gly | Lys | Pro | Leu | Gly | Glu | Gly | |

-continued

| | | | | |
|---|---|---|---|---|
| | 465 | 470 | 475 | 480 |
| tgc ttc ggc cag gtg gtc atg gcg gag gcc atc ggc att gac aag gac<br>Cys Phe Gly Gln Val Val Met Ala Glu Ala Ile Gly Ile Asp Lys Asp<br>485 490 495 | | | | 1488 |
| cgg gcc gcc aag cct gtc acc gta gcc gtg aag atg ctg aaa gac gat<br>Arg Ala Ala Lys Pro Val Thr Val Ala Val Lys Met Leu Lys Asp Asp<br>500 505 510 | | | | 1536 |
| gcc act gac aag gac ctg tcg gac ctg gtg tct gag atg gag atg atg<br>Ala Thr Asp Lys Asp Leu Ser Asp Leu Val Ser Glu Met Glu Met Met<br>515 520 525 | | | | 1584 |
| aag atg atc ggg aaa cac aaa aac atc atc aac ctg ctg ggc gcc tgc<br>Lys Met Ile Gly Lys His Lys Asn Ile Ile Asn Leu Leu Gly Ala Cys<br>530 535 540 | | | | 1632 |
| acg cag ggc ggg ccc ctg tac gtg ctg gtg gag tac gcg gcc aag ggt<br>Thr Gln Gly Gly Pro Leu Tyr Val Leu Val Glu Tyr Ala Ala Lys Gly<br>545 550 555 560 | | | | 1680 |
| aac ctg cgg gag ttt ctg cgg gcg cgg cgg ccc ccg ggc ctg gac tac<br>Asn Leu Arg Glu Phe Leu Arg Ala Arg Arg Pro Pro Gly Leu Asp Tyr<br>565 570 575 | | | | 1728 |
| tcc ttc gac acc tgc aag ccg ccc gag gag cag ctc acc ttc aag gac<br>Ser Phe Asp Thr Cys Lys Pro Pro Glu Glu Gln Leu Thr Phe Lys Asp<br>580 585 590 | | | | 1776 |
| ctg gtg tcc tgt gcc tac cag gtg gcc cgg ggc atg gag tac ttg gcc<br>Leu Val Ser Cys Ala Tyr Gln Val Ala Arg Gly Met Glu Tyr Leu Ala<br>595 600 605 | | | | 1824 |
| tcc cag aag tgc atc cac agg gac ctg gct gcc cgc aat gtg ctg gtg<br>Ser Gln Lys Cys Ile His Arg Asp Leu Ala Ala Arg Asn Val Leu Val<br>610 615 620 | | | | 1872 |
| acc gag gac aac gtg atg aag atc gca gac ttc ggg ctg gcc cgg gac<br>Thr Glu Asp Asn Val Met Lys Ile Ala Asp Phe Gly Leu Ala Arg Asp<br>625 630 635 640 | | | | 1920 |
| gtg cac aac ctc gac tac tac aag aag aca acc aac ggc cgg ctg ccc<br>Val His Asn Leu Asp Tyr Tyr Lys Lys Thr Thr Asn Gly Arg Leu Pro<br>645 650 655 | | | | 1968 |
| gtg aag tgg atg gcg cct gag gcc ttg ttt gac cga gtc tac act cac<br>Val Lys Trp Met Ala Pro Glu Ala Leu Phe Asp Arg Val Tyr Thr His<br>660 665 670 | | | | 2016 |
| cag agt gac gtc tgg tcc ttt ggg gtc ctg ctc tgg gag atc ttc acg<br>Gln Ser Asp Val Trp Ser Phe Gly Val Leu Leu Trp Glu Ile Phe Thr<br>675 680 685 | | | | 2064 |
| ctg ggg ggc tcc ccg tac ccc ggc atc cct gtg gag gag ctc ttc aag<br>Leu Gly Gly Ser Pro Tyr Pro Gly Ile Pro Val Glu Glu Leu Phe Lys<br>690 695 700 | | | | 2112 |
| ctg ctg aag gag ggc cac cgc atg gac aag ccc gcc aac tgc aca cac<br>Leu Leu Lys Glu Gly His Arg Met Asp Lys Pro Ala Asn Cys Thr His<br>705 710 715 720 | | | | 2160 |
| gac ctg tac atg atc atg cgg gag tgc tgg cat gcc gcg ccc tcc cag<br>Asp Leu Tyr Met Ile Met Arg Glu Cys Trp His Ala Ala Pro Ser Gln<br>725 730 735 | | | | 2208 |
| agg ccc acc ttc aag cag ctg gtg gat tac ctg gag cag ttt gga act<br>Arg Pro Thr Phe Lys Gln Leu Val Asp Tyr Leu Glu Gln Phe Gly Thr<br>740 745 750 | | | | 2256 |
| tcc tcg ttt aag gag tcg gcc ttg agg aag cag tcc tta tac ctc aag<br>Ser Ser Phe Lys Glu Ser Ala Leu Arg Lys Gln Ser Leu Tyr Leu Lys<br>755 760 765 | | | | 2304 |
| ttt gac ccc ctc ctg agg gac agt cct ggt aga cca gtg ccc gtg gcc<br>Phe Asp Pro Leu Leu Arg Asp Ser Pro Gly Arg Pro Val Pro Val Ala<br>770 775 780 | | | | 2352 |
| acc gag acc agc agc atg cac ggt gca aat gag act ccc tca gga cgt<br>| | | | 2400 |

-continued

```
Thr Glu Thr Ser Ser Met His Gly Ala Asn Glu Thr Pro Ser Gly Arg
785                 790                 795                 800 ccg cgg gaa gcc aag ctt gtg gag ttc gat ttc ttg gga gca ctg gac      2448
Pro Arg Glu Ala Lys Leu Val Glu Phe Asp Phe Leu Gly Ala Leu Asp
                805                 810                 815 att cct gtg cca ggc cca ccc cca ggt gtt ccc gcg cct ggg ggc cca      2496
Ile Pro Val Pro Gly Pro Pro Pro Gly Val Pro Ala Pro Gly Gly Pro
            820                 825                 830 ccc ctg tcc acc gga cct ata gtg gac ctg ctc cag tac agc cag aag      2544
Pro Leu Ser Thr Gly Pro Ile Val Asp Leu Leu Gln Tyr Ser Gln Lys
        835                 840                 845 gac ctg gat gca gtg gta aag gcg aca cag gag gag aac cgg gag ctg      2592
Asp Leu Asp Ala Val Val Lys Ala Thr Gln Glu Glu Asn Arg Glu Leu
    850                 855                 860 agg agc agg tgt gag gag ctc cac ggg aag aac ctg gaa ctg ggg aag      2640
Arg Ser Arg Cys Glu Glu Leu His Gly Lys Asn Leu Glu Leu Gly Lys
865                 870                 875                 880 atc atg gac agg ttc gaa gag gtt gtg tac cag gcc atg gag gaa gtt      2688
Ile Met Asp Arg Phe Glu Glu Val Val Tyr Gln Ala Met Glu Glu Val
                885                 890                 895 cag aag cag aag gaa ctt tcc aaa gct gaa atc cag aaa gtt cta aaa      2736
Gln Lys Gln Lys Glu Leu Ser Lys Ala Glu Ile Gln Lys Val Leu Lys
                900                 905                 910 gaa aaa gac caa ctt acc aca gat ctg aac tcc atg gag aag tcc ttc      2784
Glu Lys Asp Gln Leu Thr Thr Asp Leu Asn Ser Met Glu Lys Ser Phe
        915                 920                 925 tcc gac ctc ttc aag cgt ttt gag aaa cag aaa gag gtg atc gag ggc      2832
Ser Asp Leu Phe Lys Arg Phe Glu Lys Gln Lys Glu Val Ile Glu Gly
    930                 935                 940 tac cgc aag aac gaa gag tca ctg aag aag tgc gtg gag gat tac ctg      2880
Tyr Arg Lys Asn Glu Glu Ser Leu Lys Lys Cys Val Glu Asp Tyr Leu
945                 950                 955                 960 gca agg atc acc cag gag ggc cag agg tac caa gcc ctg aag gcc cac      2928
Ala Arg Ile Thr Gln Glu Gly Gln Arg Tyr Gln Ala Leu Lys Ala His
                965                 970                 975 gcg gag gag aag ctg cag ctg gca aac gag gag atc gcc cag gtc cgg      2976
Ala Glu Glu Lys Leu Gln Leu Ala Asn Glu Glu Ile Ala Gln Val Arg
                980                 985                 990 agc aag gcc cag gcg gaa gcg ttg gcc ctc cag gcc agc ctg agg aag      3024
Ser Lys Ala Gln Ala Glu Ala Leu Ala Leu Gln Ala Ser Leu Arg Lys
        995                 1000                1005 gag cag atg cgc atc cag tcg ctg gag aag aca gtg gag cag aag           3069
Glu Gln Met Arg Ile Gln Ser Leu Glu Lys Thr Val Glu Gln Lys
    1010                1015                1020 act aaa gag aac gag gag ctg acc agg atc tgc gac gac ctc atc           3114
Thr Lys Glu Asn Glu Glu Leu Thr Arg Ile Cys Asp Asp Leu Ile
    1025                1030                1035 tcc aag atg gag aag atc tga                                           3135
Ser Lys Met Glu Lys Ile
    1040
```

<210> SEQ ID NO 28
<211> LENGTH: 1044
<212> TYPE: PRT
<213> ORGANISM: Homo sapiens

<400> SEQUENCE: 28

```
Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
```

-continued

```
            20                  25                  30
Gly Arg Ala Ala Glu Val Pro Gly Pro Glu Pro Gln Gln Glu Gln
                35                  40                  45
Leu Val Phe Gly Ser Gly Asp Ala Val Glu Leu Ser Cys Pro Pro
 50                  55                  60
Gly Gly Gly Pro Met Gly Pro Thr Val Trp Lys Asp Gly Thr Gly
 65                  70                  75                  80
Leu Val Pro Ser Glu Arg Val Leu Val Gly Pro Gln Arg Leu Gln Val
                85                  90                  95
Leu Asn Ala Ser His Glu Asp Ser Gly Ala Tyr Ser Cys Arg Gln Arg
                100                 105                 110
Leu Thr Gln Arg Val Leu Cys His Phe Ser Val Arg Val Thr Asp Ala
                115                 120                 125
Pro Ser Ser Gly Asp Asp Glu Asp Gly Glu Asp Glu Ala Glu Asp Thr
                130                 135                 140
Gly Ala Pro Tyr Trp Thr Arg Pro Glu Arg Met Asp Lys Lys Leu Leu
145                 150                 155                 160
Ala Val Pro Ala Ala Asn Thr Val Arg Phe Arg Cys Pro Ala Ala Gly
                165                 170                 175
Asn Pro Thr Pro Ser Ile Ser Trp Leu Lys Asn Gly Arg Glu Phe Arg
                180                 185                 190
Gly Glu His Arg Ile Gly Gly Ile Lys Leu Arg His Gln Gln Trp Ser
                195                 200                 205
Leu Val Met Glu Ser Val Val Pro Ser Asp Arg Gly Asn Tyr Thr Cys
                210                 215                 220
Val Val Glu Asn Lys Phe Gly Ser Ile Arg Gln Thr Tyr Thr Leu Asp
225                 230                 235                 240
Val Leu Glu Arg Ser Pro His Arg Pro Ile Leu Gln Ala Gly Leu Pro
                245                 250                 255
Ala Asn Gln Thr Ala Val Leu Gly Ser Asp Val Glu Phe His Cys Lys
                260                 265                 270
Val Tyr Ser Asp Ala Gln Pro His Ile Gln Trp Leu Lys His Val Glu
                275                 280                 285
Val Asn Gly Ser Lys Val Gly Pro Asp Gly Thr Pro Tyr Val Thr Val
                290                 295                 300
Leu Lys Ser Trp Ile Ser Glu Ser Val Glu Ala Asp Val Arg Leu Arg
305                 310                 315                 320
Leu Ala Asn Val Ser Glu Arg Asp Gly Gly Glu Tyr Leu Cys Arg Ala
                325                 330                 335
Thr Asn Phe Ile Gly Val Ala Glu Lys Ala Phe Trp Leu Ser Val His
                340                 345                 350
Gly Pro Arg Ala Ala Glu Glu Glu Leu Val Glu Ala Asp Glu Ala Gly
                355                 360                 365
Ser Val Tyr Ala Gly Ile Leu Ser Tyr Gly Val Gly Phe Phe Leu Phe
                370                 375                 380
Ile Leu Val Val Ala Ala Val Thr Leu Cys Arg Leu Arg Ser Pro Pro
385                 390                 395                 400
Lys Lys Gly Leu Gly Ser Pro Thr Val His Lys Ile Ser Arg Phe Pro
                405                 410                 415
Leu Lys Arg Gln Gln Val Ser Leu Glu Ser Asn Ala Ser Met Ser Ser
                420                 425                 430
Asn Thr Pro Leu Val Arg Ile Ala Arg Leu Ser Ser Gly Glu Gly Pro
                435                 440                 445
```

-continued

Thr Leu Ala Asn Val Ser Glu Leu Glu Leu Pro Ala Asp Pro Lys Trp
    450                 455                 460

Glu Leu Ser Arg Ala Arg Leu Thr Leu Gly Lys Pro Leu Gly Glu Gly
465                 470                 475                 480

Cys Phe Gly Gln Val Val Met Ala Glu Ala Ile Gly Ile Asp Lys Asp
                    485                 490                 495

Arg Ala Ala Lys Pro Val Thr Val Ala Val Lys Met Leu Lys Asp Asp
                500                 505                 510

Ala Thr Asp Lys Asp Leu Ser Asp Leu Val Ser Glu Met Glu Met Met
            515                 520                 525

Lys Met Ile Gly Lys His Lys Asn Ile Ile Asn Leu Leu Gly Ala Cys
    530                 535                 540

Thr Gln Gly Gly Pro Leu Tyr Val Leu Val Glu Tyr Ala Ala Lys Gly
545                 550                 555                 560

Asn Leu Arg Glu Phe Leu Arg Ala Arg Arg Pro Pro Gly Leu Asp Tyr
                565                 570                 575

Ser Phe Asp Thr Cys Lys Pro Pro Glu Glu Gln Leu Thr Phe Lys Asp
                580                 585                 590

Leu Val Ser Cys Ala Tyr Gln Val Ala Arg Gly Met Glu Tyr Leu Ala
            595                 600                 605

Ser Gln Lys Cys Ile His Arg Asp Leu Ala Ala Arg Asn Val Leu Val
    610                 615                 620

Thr Glu Asp Asn Val Met Lys Ile Ala Asp Phe Gly Leu Ala Arg Asp
625                 630                 635                 640

Val His Asn Leu Asp Tyr Tyr Lys Lys Thr Thr Asn Gly Arg Leu Pro
                645                 650                 655

Val Lys Trp Met Ala Pro Glu Ala Leu Phe Asp Arg Val Tyr Thr His
                660                 665                 670

Gln Ser Asp Val Trp Ser Phe Gly Val Leu Leu Trp Glu Ile Phe Thr
            675                 680                 685

Leu Gly Gly Ser Pro Tyr Pro Gly Ile Pro Val Glu Glu Leu Phe Lys
    690                 695                 700

Leu Leu Lys Glu Gly His Arg Met Asp Lys Pro Ala Asn Cys Thr His
705                 710                 715                 720

Asp Leu Tyr Met Ile Met Arg Glu Cys Trp His Ala Ala Pro Ser Gln
                725                 730                 735

Arg Pro Thr Phe Lys Gln Leu Val Asp Tyr Leu Glu Gln Phe Gly Thr
                740                 745                 750

Ser Ser Phe Lys Glu Ser Ala Leu Arg Lys Gln Ser Leu Tyr Leu Lys
            755                 760                 765

Phe Asp Pro Leu Leu Arg Asp Ser Pro Gly Arg Pro Val Pro Val Ala
    770                 775                 780

Thr Glu Thr Ser Ser Met His Gly Ala Asn Glu Thr Pro Ser Gly Arg
785                 790                 795                 800

Pro Arg Glu Ala Lys Leu Val Glu Phe Asp Phe Leu Gly Ala Leu Asp
                805                 810                 815

Ile Pro Val Pro Gly Pro Pro Gly Val Pro Ala Pro Gly Gly Pro
                820                 825                 830

Pro Leu Ser Thr Gly Pro Ile Val Asp Leu Leu Gln Tyr Ser Gln Lys
            835                 840                 845

Asp Leu Asp Ala Val Val Lys Ala Thr Gln Glu Glu Asn Arg Glu Leu
    850                 855                 860

-continued

```
Arg Ser Arg Cys Glu Glu Leu His Gly Lys Asn Leu Glu Leu Gly Lys
865             870             875             880

Ile Met Asp Arg Phe Glu Glu Val Val Tyr Gln Ala Met Glu Glu Val
            885             890             895

Gln Lys Gln Lys Glu Leu Ser Lys Ala Glu Ile Gln Lys Val Leu Lys
        900             905             910

Glu Lys Asp Gln Leu Thr Thr Asp Leu Asn Ser Met Glu Lys Ser Phe
        915             920             925

Ser Asp Leu Phe Lys Arg Phe Glu Lys Gln Lys Glu Val Ile Glu Gly
    930             935             940

Tyr Arg Lys Asn Glu Glu Ser Leu Lys Lys Cys Val Glu Asp Tyr Leu
945             950             955             960

Ala Arg Ile Thr Gln Glu Gly Gln Arg Tyr Gln Ala Leu Lys Ala His
            965             970             975

Ala Glu Glu Lys Leu Gln Leu Ala Asn Glu Glu Ile Ala Gln Val Arg
            980             985             990

Ser Lys Ala Gln Ala Glu Ala Leu  Ala Leu Gln Ala Ser  Leu Arg Lys
        995             1000            1005

Glu Gln Met Arg Ile Gln Ser  Leu Glu Lys Thr Val  Glu Gln Lys
    1010            1015            1020

Thr Lys Glu Asn Glu Glu Leu  Thr Arg Ile Cys Asp  Asp Leu Ile
    1025            1030            1035

Ser Lys Met Glu Lys Ile
    1040
```

US 10,004,739 B2

METHODS FOR TREATING CANCER BY INHIBITING FGFR3/TACC3 FUSION PROTEIN

CROSS-REFERENCE TO RELATED APPLICATIONS

This application is a Divisional of U.S. application Ser. No. 14/383,199, which issued as U.S. Pat. No. 9,481,911, which is the U.S. National Stage application of PCT/JP2013/056225, filed Mar. 7, 2013, which claims priority from Japanese application nos. JP 2012-052147, filed Mar. 8, 2012, JP 2012-195451, filed Sep. 5, 2012, and JP 2012-280325, filed Dec. 21, 2012.

The instant application contains a Sequence Listing which has been submitted in ASCII format via EFS-WEB and is hereby incorporated by reference in its entirety. Said ASCII copy, created on Jul. 26, 2016, is named sequence.txt and is 118 KB.

TECHNICAL FIELD

The present invention relates to a method for detecting a novel fusion gene comprising an FGFR3 kinase domain and a fusion protein encoded by each fusion gene. Moreover, the present invention relates to a pharmaceutical composition comprising substances inhibiting the fusion proteins for treating cancer which is positive for either the fusion gene or the fusion protein.

BACKGROUND ART

Fibroblast Growth Factor Receptor 3 (FGFR3) is a gene located on the short arm of chromosome 4 and a protein encoded by this gene is a receptor tyrosine kinase. This protein has a transmembrane domain in the central portion, a tyrosine kinase domain on the carboxyl-terminal, and an extracellular domain on the amino-terminal. FGFR3 is known to have isoforms including FGFR3b and FGFR3c resulting from alternative splicing conducted on the amino-terminal. FGF-1 and FGF-9 are ligands of FGFR3b, and FGF-1, FGF-2, FGF-4, FGF-8, FGF-9, FGF-17, FGF-18, and FGF-23 are ligands of FGFR3c. The protein is activated by auto-phosphorylation of its tyrosine residue through dimerization with another FGFR3 protein (Non-Patent Document 1 and Non-Patent Document 2).

It is known that in multiple osteosarcoma, FGFR3 is fused with an IgH gene by interchromosomal translocation, and an aberrant protein translated by the fusion gene results in abnormal proliferation of cells and achondroplasia (Non-Patent Document 3). Moreover, it is known that in peripheral T-cell malignant lymphoma, FGFR3 is fused with ETV6 by interchromosomal translocation (Non-Patent Document 4). Furthermore, it is known that in bladder cancer or the like, activating point mutation of the FGFR3 is observed. Furthermore, activating mutations of the FGFR3 are detected mainly in bladder cancer specimens. Introduction of these mutant genes into mouse normal cells, NIH3T3 cells, induces transformation of the NIH3T3 cells into malignant cells, whereas wild type FGFR3 does not induce the transformation in the same condition (Non-Patent Document 5).

Transforming, acidic coiled-coil containing protein 3 (TACC3) is a gene located on the short arm of chromosome 4, where FGFR3 is also located, and consists of 16 exons. It is known that TACC3 encodes a spindle motor protein which is involved in stabilization of mitotic spindle (Non-Patent Document 6).

RELATED ART

Non-Patent Document

Non-Patent Document 1: "Cytokine & Growth Factor Review, (United Kingdom), 2005, Vol. 16, p. 139-149"
Non-Patent Document 2: "Biochemical journal, ((United Kingdom), 2011, Vol. 437, p. 199-213)"
Non-Patent Document 3: "Blood ((United States), 2002, Vol. 100, p. 1579-1583)"
Non-Patent Document 4: "Cancer Research, ((United States), 2001, Vol. 61, p. 8371-8374)"
Non-Patent Document 5: "Oncogene, ((United Kingdom), 2009, Vol. 28, p. 4306-4316)"
Non-Patent Document 6: "Trends in Cell Biology, ((United Kingdom), 2008, Vol. 18, p. 379-388)"

DISCLOSURE OF INVENTION

Problems to be Solved by the Invention

The present invention aims to elucidate a polynucleotide as a novel gene responsible for cancer and aims to thus provide a method for detecting the polynucleotide and a polypeptide encoded by the polynucleotide and a detection kit, a primer set, and a probe set which are used for the method. The present invention also aims to provide a drug to inhibit a polypeptide of the present invention for patients with cancer expressing those fusion proteins.

Means for Solving the Problems

In the present invention, novel fusion genes obtained from specimens of patients with lung cancer and patients with bladder cancer, in which a portion of FGFR3 as a kinase has been fused with a portion of a TACC3 gene, are isolated and identified (Examples 1, 2, 3, and 23). It was found that these fusion genes are present in the specimens of the patients with lung cancer and bladder cancer (Examples 4, 5, 6, 20, and 23). Furthermore, in the present invention, retrovirus particles for expressing these fusion genes were prepared (Examples 7, 10, and 24), and it was found that infected cells acquired tumorigenic potential and the fusion genes were responsible for its potential (Examples 8, 11, and 25). Moreover, the present invention established a method for detecting the novel fusion gene and a fusion protein encoded by the novel fusion gene from cell lines derived from patients with bladder cancer or specimens of patients with lung cancer or specimens of patients with bladder cancer (Examples 4, 5, 6, 19, 20, 27, and 28). In addition, it was found that a inhibitor of the fusion protein is effective for the treatment of cancer patients expressing the fusion proteins or the fusion genes encoding the fusion proteins (that is, the patients with cancer which are positive for either a fusion gene composed of the FGFR3 gene and the TACC3 gene or a fusion protein composed of FGFR3 and TACC3) based on the discovery that the drug which has inhibitory action on the fusion protein encoded by the fusion gene inhibits tumorigenicity of the infected cell (Examples 9, 12, 13, 14, 16, 22, and 30).

Up to now, it has been considered that the wild-type FGFR3 alone does not have the ability to transform normal cells into malignant cells. However, the fact that even wild-type FGFR3 acquired the ability through being fused with TACC3 is a surprising finding. Moreover, astonishingly, it was confirmed that the TACC3 has been fused on the carboxyl-terminal of the FGFR3 in this fusion protein. This structure is different from that of the fusion kinases discovered so far, in which kinase polypeptides were located on the carboxy-terminal.

Based on the findings, the present inventors established a method for detecting those fusion genes and provided a kit, a primer set, and a probe set for the method. In this way, they made it possible to screen out patients with cancer subjected to receive drug treatment using the inhibitor of the fusion proteins by detecting the fusion genes or the fusion proteins encoded by the fusion genes. Furthermore, the inventors found that the inhibitor of the fusion proteins (particularly, Compounds A to E, Dovitinib, AZD4547, BGJ398, or LY2874455) inhibits the activity of the fusion protein composed of FGFR3 and TACC3 and is effective for cancer (for example, lung cancer or bladder cancer) expressing the fusion protein composed of FGFR3 and TACC3 (that is, cancer which is positive for either the fusion gene composed of the FGFR3 gene and the TACC3 gene or the fusion protein composed of FGFR3 and TACC3) or the like.

That is, the present invention relates to the following:

[1] A method for detecting a fusion gene composed of a fibroblast growth factor receptor 3 (FGFR3) gene and a transforming acidic coiled-coil containing protein 3 (TACC3) gene or a fusion protein composed of FGFR3 and TACC3, which comprises detecting the existence of either a polynucleotide encoding the following polypeptide or the polypeptide in a specimen obtained from a test subject:

A polypeptide which has tumorigenicity and comprises an amino acid sequence having 90% or more identity to the amino acid sequence represented by amino acid numbers 461 to 947 of SEQ ID NO: 2, amino acid numbers 461 to 982 of SEQ ID NO: 4, amino acid numbers 461 to 996 of SEQ ID NO: 6, amino acid numbers 461 to 1043 of SEQ ID NO: 26, or amino acid numbers 461 to 1040 of SEQ ID NO: 28.

[2] The method according to [1],
wherein the polypeptide is a polypeptide which has tumorigenicity and comprises the amino acid sequence represented by amino acid numbers 461 to 947 of SEQ ID NO: 2, amino acid numbers 461 to 982 of SEQ ID NO: 4, amino acid numbers 461 to 996 of SEQ ID NO: 6, amino acid numbers 461 to 1043 of SEQ ID NO: 26, or amino acid numbers 461 to 1040 of SEQ ID NO: 28; or a polypeptide which has tumorigenicity and comprises an amino acid sequence having deletion, substitution, and/or insertion of 1 to 10 amino acids in the amino acid sequence represented by amino acid numbers 461 to 947 of SEQ ID NO: 2, amino acid numbers 461 to 982 of SEQ ID NO: 4, amino acid numbers 461 to 996 of SEQ ID NO: 6, amino acid numbers 461 to 1043 of SEQ ID NO: 26, or amino acid numbers 461 to 1040 of SEQ ID NO: 28.

[3] The method according to [1],
wherein the polypeptide is a polypeptide which has tumorigenicity and comprises an amino acid sequence having 90% or more identity to the amino acid sequence represented by SEQ ID NO: 2, SEQ ID NO: 4, SEQ ID NO: 6, SEQ ID NO: 26, or SEQ ID NO: 28.

[4] The method according to [1],
wherein the polypeptide is a polypeptide which has tumorigenicity and comprises the amino acid sequence represented by SEQ ID NO: 2, SEQ ID NO: 4, SEQ ID NO: 6, SEQ ID NO: 26, or SEQ ID NO: 28; or a polypeptide which has tumorigenicity and comprises an amino acid sequence having deletion, substitution, and/or insertion of 1 to 10 amino acids in the amino acid sequence represented by SEQ ID NO: 2, SEQ ID NO: 4, SEQ ID NO: 6, SEQ ID NO: 26, or SEQ ID NO: 28.

[5] The method according to [1],
wherein the polypeptide is a polypeptide consisting of the amino acid sequence represented by SEQ ID NO: 2, SEQ ID NO: 4, SEQ ID NO: 6, SEQ ID NO: 26, or SEQ ID NO: 28.

[6] A kit for detecting a fusion gene composed of an FGFR3 gene and a TACC3 gene, which comprises a sense primer and an antisense primer designed to be able to specifically amplify a polynucleotide encoding the following polypeptide:

A polypeptide which has tumorigenicity and comprises an amino acid sequence having 90% or more identity to the amino acid sequence represented by amino acid numbers 461 to 947 of SEQ ID NO: 2, amino acid numbers 461 to 982 of SEQ ID NO: 4, amino acid numbers 461 to 996 of SEQ ID NO: 6, amino acid numbers 461 to 1043 of SEQ ID NO: 26, or amino acid numbers 461 to 1040 of SEQ ID NO: 28.

[7] The kit according to [6],
wherein the polypeptide is a polypeptide which has tumorigenicity and comprises the amino acid sequence represented by amino acid numbers 461 to 947 of SEQ ID NO: 2, amino acid numbers 461 to 982 of SEQ ID NO: 4, amino acid numbers 461 to 996 of SEQ ID NO: 6, amino acid numbers 461 to 1043 of SEQ ID NO: 26, or amino acid numbers 461 to 1040 of SEQ ID NO: 28; or a polypeptide which has tumorigenicity and comprises an amino acid sequence having deletion, substitution, and/or insertion of 1 to 10 amino acids in the amino acid sequence represented by amino acid numbers 461 to 947 of SEQ ID NO: 2, amino acid numbers 461 to 982 of SEQ ID NO: 4, amino acid numbers 461 to 996 of SEQ ID NO: 6, amino acid numbers 461 to 1043 of SEQ ID NO: 26, or amino acid numbers 461 to 1040 of SEQ ID NO: 28.

[8] The kit according to [6],
wherein the polypeptide is a polypeptide which has tumorigenicity and comprises an amino acid sequence having 90% or more identity to the amino acid sequence represented by SEQ ID NO: 2, SEQ ID NO: 4, SEQ ID NO: 6, SEQ ID NO: 26, or SEQ ID NO: 28.

[9] The kit according to [6],
wherein the polypeptide is a polypeptide which has tumorigenicity and comprises the amino acid sequence represented by SEQ ID NO: 2, SEQ ID NO: 4, SEQ ID NO: 6, SEQ ID NO: 26, or SEQ ID NO: 28; or a polypeptide which has tumorigenicity and comprises an amino acid sequence having deletion, substitution, and/or insertion of 1 to 10 amino acids in the amino acid sequence represented by SEQ ID NO: 2, SEQ ID NO: 4, SEQ ID NO: 6, SEQ ID NO: 26, or SEQ ID NO: 28.

[10] The kit according to [6],
wherein the polypeptide is a polypeptide consisting of the amino acid sequence represented by SEQ ID NO: 2, SEQ ID NO: 4, SEQ ID NO: 6, SEQ ID NO: 26, or SEQ ID NO: 28.

[11] A primer set for detecting a fusion gene composed of an FGFR3 gene and a TACC3 gene which is selected from a group consisting of the following a) to e):

a) A primer set comprising an antisense primer consisting of nucleic acid molecules hybridized with a polynucleotide consisting of the nucleotide sequence represented by SEQ ID NO: 1 under stringent conditions and a sense primer consisting of nucleic acid molecules hybridized with a complementary strand of the polynucleotide under stringent conditions, b) A primer set comprising an antisense primer consisting of nucleic acid molecules hybridized with a polynucleotide consisting of the nucleotide sequence represented by SEQ ID NO: 3 under stringent conditions and a sense primer consisting of nucleic acid molecules hybridized with a complementary strand of the polynucleotide under stringent conditions, c) A primer set comprising an antisense primer consisting of nucleic acid molecules hybridized with a polynucleotide consisting of the nucleotide sequence represented by SEQ ID NO: 5 under stringent conditions and a sense primer consisting of nucleic acid molecules hybridized with a complementary strand of the polynucleotide under stringent conditions, d) A primer set comprising an antisense primer consisting of nucleic acid molecules hybridized with a polynucleotide consisting of the nucleotide sequence represented by SEQ ID NO: 25 under stringent conditions and a sense primer consisting of nucleic acid molecules hybridized with a complementary strand of the polynucleotide under stringent conditions, and e) A primer set comprising an antisense primer consisting of nucleic acid molecules hybridized with a polynucleotide consisting of the nucleotide sequence represented by SEQ ID NO: 27 under stringent conditions and a sense primer consisting of nucleic acid molecules hybridized with a complementary strand of the polynucleotide under stringent conditions.

[12] A primer set of:
a sense primer consisting of an oligonucleotide of at least any consecutive 16 bases between nucleotide positions 1 and 2280 of SEQ ID NO: 1; and
an antisense primer consisting of an oligonucleotide complementary to an oligonucleotide of at least any consecutive 16 bases between nucleotide positions 2281 to 2856 of SEQ ID NO: 1.

[13] A primer set of:
a sense primer consisting of an oligonucleotide of at least any consecutive 16 bases between nucleotide positions 1 and 2280 of SEQ ID NO: 3; and
an antisense primer consisting of an oligonucleotide complementary to an oligonucleotide of at least any consecutive 16 bases between nucleotide positions 2281 and 2961 of SEQ ID NO: 3.

[14] A primer set of:
a sense primer consisting of an oligonucleotide of at least any consecutive 16 bases between nucleotide positions 1 and 2368 of SEQ ID NO: 5; and
an antisense primer consisting of an oligonucleotide complementary to an oligonucleotide of at least any consecutive 16 bases between nucleotide positions 2369 and 3003 of SEQ ID NO: 5.

[15] A primer set of:
a sense primer consisting of an oligonucleotide of at least any consecutive 16 bases between nucleotide positions 1 and 2242 of SEQ ID NO: 25; and
an antisense primer consisting of an oligonucleotide complementary to an oligonucleotide of at least any consecutive 16 bases between nucleotide positions 2243 and 3144 of SEQ ID NO: 25.

[16] A primer set of:
a sense primer consisting of an oligonucleotide of at least any consecutive 16 bases between nucleotide positions 1 and 2233 of SEQ ID NO: 27; and
an antisense primer consisting of an oligonucleotide complementary to an oligonucleotide consisting of at least any consecutive 16 bases between nucleotide positions 2234 and 3135 of SEQ ID NO: 27.

[17] Probe sets for detecting a fusion gene composed of an FGFR3 gene and a TACC3 gene which is selected from a group consisting of the following a) to c).

a) Probe sets comprising multiple kinds of probe sets (preferably comprising 20 kinds of probe sets) consisting of probe pairs which are adjacent to each other and comprises oligonucleotides complementary to at least any consecutive 16 bases between nucleotide positions 1 and 2280 of SEQ ID NO: 1, and probe set comprising multiple kinds of probe sets (preferably comprising 20 kinds of probe sets) consisting of probe pairs which are adjacent to each other and comprises oligonucleotides complementary to at least any consecutive 16 bases between nucleotide positions 2281 and 2856 of SEQ ID NO: 1 b) Probe sets comprising multiple kinds of probe sets (preferably comprising 20 kinds of probe sets) consisting of probe pairs which are adjacent to each other and comprises oligonucleotides complementary to at least any consecutive 16 bases between nucleotide positions 1 and 2280 of SEQ ID NO: 3, and probe sets comprising multiple kinds of probe sets (preferably comprising 20 kinds of probe sets) consisting of probe pairs which are adjacent to each other and comprises oligonucleotides complementary to at least any consecutive 16 bases between nucleotide positions 2281 and 2961 of SEQ ID NO: 3 c) Probe sets comprising multiple kinds of probe sets (preferably comprising 20 kinds of probe sets) consisting of probe pairs which are adjacent to each other and comprises oligonucleotides complementary to at least any consecutive 16 bases between nucleotide positions 1 and 2368 of SEQ ID NO: 5, and probe sets comprising multiple kinds of probe sets (preferably comprising 20 kinds of probe sets) consisting of probe pairs which are adjacent to each other and comprises oligonucleotides complementary to at least any consecutive 16 bases between nucleotide positions 2369 and 3003 of SEQ ID NO: 5

[18] The method for detecting a fusion gene composed of an FGFR3 gene and a TACC3 gene according to any one of [1] to [5],
wherein the step of detecting the existence of the polynucleotide comprises performing in-situ hybridization by using the specimen obtained from the test subject and the probe sets according to [17], amplifying signals of the hybridization, and detecting the superposition of the signals.

[19] A kit for detecting a fusion gene composed of an FGFR3 gene and a TACC3 gene, comprising:
the probe sets for detecting the fusion gene composed of the FGFR3 gene and the TACC3 gene according to [17]; and
a reagent for amplifying signals of the hybridization.

[20] The method for detecting the fusion protein composed of FGFR3 and TACC3 according to any one of [1] to [5],
wherein the step of detecting the existence of a polypeptide comprises i) bringing an antibody (primary antibody) which recognizes a portion derived from the FGFR3 gene of the polypeptide and an antibody (primary antibody) which recognizes a portion derived from the TACC3 gene of the polypeptide into contact with the specimen obtained from the test subject, ii) adding secondary antibodies which are conjugated with oligonucleotides and respectively bind to the primary antibodies, iii) causing a ligation reaction by adding a ligation solution containing two kinds of oligonucleotides which are partially complementary to the oligonucleotides conjugated with the secondary antibodies and a ligase which can form a cyclic structure between the secondary antibodies by causing ligation when the two kinds of oligonucleotides come close to each other, iv) elongating a nucleic acid sequence along the formed cyclic structure, v) hybridizing a labeled oligonucleotide probe which can be hybridized with the elongated nucleic acid sequence, and vi) detecting signals of the label.

[21] A kit for detecting a fusion protein composed of FGFR3 and TACC3 which is used for the method for detecting the fusion protein composed of FGFR3 and TACC3 according to any one of [1] to [5], comprising:

an antibody (primary antibody) which recognizes a portion derived from the FGFR3 gene of the fusion polypeptide;

an antibody (primary antibody) which recognizes a portion derived from the TACC3 gene of the fusion polypeptide;

secondary antibodies which are conjugated with oligonucleotides and respectively bind to the primary antibodies;

two kinds of oligonucleotides which are partially complementary to the oligonucleotides conjugated with the secondary antibodies;

a ligase which can form a cyclic structure between the secondary antibodies by causing ligation when the two kinds of oligonucleotides come close to each other; and a labeled oligonucleotide probe.

[22] A pharmaceutical composition for treating cancer which comprises a substance inhibiting the following polypeptide and is positive for either a fusion gene composed of an FGFR3 gene and a TACC3 gene or a fusion protein composed of FGFR3 and TACC3:

A polypeptide which has tumorigenicity and comprises an amino acid sequence having 90% or more identity to the amino acid sequence represented by amino acid numbers 461 to 947 of SEQ ID NO: 2, amino acid numbers 461 to 982 of SEQ ID NO: 4, or amino acid numbers 461 to 996 of SEQ ID NO: 6.

[23] The pharmaceutical composition according to [22], wherein the polypeptide is a polypeptide which has tumorigenicity and comprises the amino acid sequence represented by amino acid numbers 461 to 947 of SEQ ID NO: 2, amino acid numbers 461 to 982 of SEQ ID NO: 4, or amino acid numbers 461 to 996 of SEQ ID NO: 6; or a polypeptide which has tumorigenicity and comprises an amino acid sequence having deletion, substitution, and/or insertion of 1 to 10 amino acids in the amino acid sequence represented by amino acid numbers 461 to 947 of SEQ ID NO: 2, amino acid numbers 461 to 982 of SEQ ID NO: 4, or amino acid numbers 461 to 996 of SEQ ID NO: 6.

[24] The pharmaceutical composition according to [22], wherein the polypeptide is a polypeptide consisting of the amino acid sequence represented by amino acid numbers 461 to 947 of SEQ ID NO: 2, amino acid numbers 461 to 982 of SEQ ID NO: 4, or amino acid numbers 461 to 996 of SEQ ID NO: 6.

[25] The pharmaceutical composition according to [22], wherein the polypeptide is a polypeptide which has tumorigenicity and comprises an amino acid sequence having 90% or more identity to the amino acid sequence represented by SEQ ID NO: 2, SEQ ID NO: 4, or SEQ ID NO: 6.

[26] The pharmaceutical composition according to [22], wherein the polypeptide is a polypeptide which has tumorigenicity and comprises the amino acid sequence represented by SEQ ID NO: 2, SEQ ID NO: 4, or SEQ ID NO: 6; or a polypeptide which has tumorigenicity and comprises an amino acid sequence having deletion, substitution, and/or insertion of 1 to 10 amino acids in the amino acid sequence represented by SEQ ID NO: 2, SEQ ID NO: 4, or SEQ ID NO: 6.

[27] The pharmaceutical composition according to [22], wherein the polypeptide is a polypeptide consisting of the amino acid sequence represented by SEQ ID NO: 2, SEQ ID NO: 4, or SEQ ID NO: 6.

[28] The pharmaceutical composition for treating cancer according to any one of [22] to [27],
wherein the substance inhibiting the polypeptide is Dovitinib, AZD4547, BGJ398, or LY2874455.

[29] The pharmaceutical composition for treating cancer according to any one of [22] to [27],
wherein the cancer is lung cancer or bladder cancer.

[30] Use of a substance inhibiting the following polypeptide for the manufacture of a pharmaceutical composition for treating cancer which is positive for either a fusion gene composed of an FGFR3 gene and a TACC3 gene or a fusion protein composed of FGFR3 and TACC3:

A polypeptide which has tumorigenicity and comprises an amino acid sequence having 90% or more identity to the amino acid sequence represented by amino acid numbers 461 to 947 of SEQ ID NO: 2, amino acid numbers 461 to 982 of SEQ ID NO: 4, or amino acid numbers 461 to 996 of SEQ ID NO: 6.

[31] Use of a substance inhibiting the following polypeptide for treating cancer which is positive for either a fusion gene composed of an FGFR3 gene and a TACC3 gene or a fusion protein composed of FGFR3 and TACC3:

A polypeptide which has tumorigenicity and comprises an amino acid sequence having 90% or more identity to the amino acid sequence represented by amino acid numbers 461 to 947 of SEQ ID NO: 2, amino acid numbers 461 to 982 of SEQ ID NO: 4, or amino acid numbers 461 to 996 of SEQ ID NO: 6.

[32] A substance inhibiting the following polypeptide for treating cancer which is positive for either a fusion gene composed of an FGFR3 gene and a TACC3 gene or a fusion protein composed of FGFR3 and TACC3, A polypeptide which has tumorigenicity and comprises an amino acid sequence having 90% or more identity to the amino acid sequence represented by amino acid numbers 461 to 947 of SEQ ID NO: 2, amino acid numbers 461 to 982 of SEQ ID NO: 4, or amino acid numbers 461 to 996 of SEQ ID NO: 6.

[33] A method for treating cancer which is positive for either a fusion gene composed of an FGFR3 gene and a TACC3 gene or a fusion protein composed of FGFR3 and TACC3, comprising administering an effective amount of substance inhibiting the following polypeptide to a subject, A polypeptide which has tumorigenicity and comprises an amino acid sequence having 90% or more identity to the amino acid sequence represented by amino acid numbers 461 to 947 of SEQ ID NO: 2, amino acid numbers 461 to 982 of SEQ ID NO: 4, or amino acid numbers 461 to 996 of SEQ ID NO: 6.

Moreover, the present invention relates to a method for detecting cancer (particularly, lung cancer or bladder cancer) which is positive for a fusion gene composed of an FGFR3 gene and a TACC3 gene, comprising detecting the existence of a polynucleotide encoding a polypeptide according to the following (1) to (3) in a specimen obtained from a test subject:

(1) A polypeptide which has tumorigenicity and comprises an amino acid sequence having 90% or more identity to the amino acid sequence represented by amino acid numbers 461 to 947 of SEQ ID NO: 2 (or SEQ ID NO: 2), amino acid numbers 461 to 982 of SEQ ID NO: 4 (or SEQ ID NO: 4), amino acid numbers 461 to 996 of SEQ ID NO: 6 (or SEQ ID NO: 6), amino acid numbers 461 to 1043 of SEQ ID NO: 26 (or SEQ ID NO: 26), or amino acid numbers 461 to 1040 of SEQ ID NO: 28 (or SEQ ID NO: 28);

(2) A polypeptide which has tumorigenicity and comprises the amino acid sequence represented by amino acid numbers 461 to 947 of SEQ ID NO: 2 (or SEQ ID NO: 2), amino acid numbers 461 to 982 of SEQ ID NO: 4 (or SEQ ID NO: 4), amino acid numbers 461 to 996 of SEQ ID NO: 6 (or SEQ ID NO: 6), amino acid numbers 461 to 1043 of SEQ ID NO: 26 (or SEQ ID NO: 26) or amino acid numbers 461 to 1040 of SEQ ID NO: 28 (or SEQ ID NO: 28); or a polypeptide which has tumorigenicity and comprises an amino acid sequence having deletion, substitution, and/or insertion of 1 to 10 amino acids in the amino acid sequence represented by amino acid numbers 461 to 947 of SEQ ID NO: 2 (or SEQ ID NO: 2), amino acid numbers 461 to 982 of SEQ ID NO: 4 (or SEQ ID NO: 4), amino acid numbers 461 to 996 of SEQ ID NO: 6 (or SEQ ID NO: 6), amino acid numbers 461 to 1043 of SEQ ID NO: 26 (or SEQ ID NO: 26), or amino acid numbers 461 to 1040 of SEQ ID NO: 28 (or SEQ ID NO: 28); or (3) A polypeptide which consists of the amino acid sequence represented by SEQ ID NO: 2, SEQ ID NO: 4, SEQ ID NO: 6, SEQ ID NO: 26, or SEQ ID NO: 28.

The present invention relates to the method for detecting cancer (particularly, lung cancer or bladder cancer) which is positive for a fusion gene composed of an FGFR3 gene and a TACC3 gene described in the present paragraph, in which the step of detecting the existence of a polynucleotide comprises performing in-situ hybridization by using the specimen obtained from a test subject and the labeled probe set according to [17], and detecting superposition of signals of the label.

The present invention also relates to a method for diagnosing cancer (particularly, lung cancer or bladder cancer) which is positive for a fusion gene composed of an FGFR3 gene and a TACC3 gene, comprising detecting the existence of a polynucleotide encoding a polypeptide according to the following (1) to (3) in a specimen obtained from a test subject:

(1) A polypeptide which has tumorigenicity and comprises an amino acid sequence having 90% or more identity to the amino acid sequence represented by amino acid numbers 461 to 947 of SEQ ID NO: 2 (or SEQ ID NO: 2), amino acid numbers 461 to 982 of SEQ ID NO: 4 (or SEQ ID NO: 4), amino acid numbers 461 to 996 of SEQ ID NO: 6 (or SEQ ID NO: 6), amino acid numbers 461 to 1043 of SEQ ID NO: 26 (or SEQ ID NO: 26), or amino acid numbers 461 to 1040 of SEQ ID NO: 28 (or SEQ ID NO: 28);

(2) A polypeptide which has tumorigenicity and comprises the amino acid sequence represented by amino acid numbers 461 to 947 of SEQ ID NO: 2 (or SEQ ID NO: 2), amino acid numbers 461 to 982 of SEQ ID NO: 4 (or SEQ ID NO: 4), amino acid numbers 461 to 996 of SEQ ID NO: 6 (or SEQ ID NO: 6), amino acid numbers 461 to 1043 of SEQ ID NO: 26 (or SEQ ID NO: 26) or amino acid numbers 461 to 1040 of SEQ ID NO: 28 (or SEQ ID NO: 28); or a polypeptide which has tumorigenicity and comprises an amino acid sequence having deletion, substitution, and/or insertion of 1 to 10 amino acids in the amino acid sequence represented by amino acid numbers 461 to 947 of SEQ ID NO: 2 (or SEQ ID NO: 2), amino acid numbers 461 to 982 of SEQ ID NO: 4 (or SEQ ID NO: 4), amino acid numbers 461 to 996 of SEQ ID NO: 6 (or SEQ ID NO: 6), amino acid numbers 461 to 1043 of SEQ ID NO: 26 (or SEQ ID NO: 26), or amino acid numbers 461 to 1040 of SEQ ID NO: 28 (or SEQ ID NO: 28); or (3) A polypeptide which consists of the amino acid sequence represented by SEQ ID NO: 2, SEQ ID NO: 4, SEQ ID NO: 6, SEQ ID NO: 26, or SEQ ID NO: 28.

The present invention also relates to the method for diagnosing cancer (particularly, lung cancer or bladder cancer) which is positive for a fusion gene composed of an FGFR3 gene and a TACC3 gene described in the present paragraph, in which the step of detecting the existence of a polynucleotide comprises performing in-situ hybridization by using the specimen obtained from a test subject and the labeled probe set according to [17], and detecting superposition of signals of the label.

As another embodiment, the present invention relates to a method for treating cancer (particularly, lung cancer or bladder cancer) which is positive for a fusion gene composed of an FGFR3 gene and a TACC3 gene, comprising administering a substance inhibiting the polypeptide of the present invention (in an embodiment, the substance is a compound AZD4547, a compound Dovitinib, a compound BGJ398, or a compound LY2874455) to a patient diagnosed with cancer (particularly, lung cancer or bladder cancer) which is positive for a fusion gene composed of an FGFR3 gene and a TACC3 gene by the diagnosis method of the aforementioned two embodiments.

The present invention also relates to a method for detecting the existence of cancer (particularly, lung cancer or bladder cancer) which is positive for a fusion gene composed of an FGFR3 gene and a TACC3 gene, comprising:

(1) performing PCR by using a specimen obtained from a test subject as a template and using the primer set according to any one of [11] to [16], and (2) detecting the existence of a PCR product.

The present invention also relates to a method for diagnosing cancer (particularly, lung cancer or bladder cancer) which is positive for a fusion gene composed of an FGFR3 gene and a TACC3 gene, comprising:

(1) performing PCR by using a specimen obtained from a test subject as a template and using the primer set according to any one of [11] to [16], and (2) detecting the existence of a PCR product.

In another embodiment, the present invention relates to a method for treating cancer (particularly, lung cancer or bladder cancer) which is positive for a fusion gene composed of an FGFR3 gene and a TACC3 gene, comprising administering a substance inhibiting the polypeptide of the present invention (in an embodiment, the substance is a compound AZD4547, a compound Dovitinib, a compound BGJ398, or a compound LY2874455) to a patient diagnosed with cancer (particularly, lung cancer or bladder cancer) which is positive for a fusion gene composed of an FGFR3 gene and a TACC3 gene by the diagnosis method.

The present invention also relates to a method for detecting genomic rearrangement of chromosomes, comprising detecting the existence of a polynucleotide encoding the polypeptide according to the following (1) to (3) in a specimen obtained from a test subject:

(1) A polypeptide which has tumorigenicity and comprises an amino acid sequence having 90% or more identity to the amino acid sequence represented by amino acid numbers 461 to 947 of SEQ ID NO: 2 (or SEQ ID NO: 2), amino acid numbers 461 to 982 of SEQ ID NO: 4 (or SEQ ID NO: 4), amino acid numbers 461 to 996 of SEQ ID NO: 6 (or SEQ ID NO: 6), amino acid numbers 461 to 1043 of SEQ ID NO: 26 (or SEQ ID NO: 26), or amino acid numbers 461 to 1040 of SEQ ID NO: 28 (or SEQ ID NO: 28);

(2) A polypeptide which has tumorigenicity and comprises the amino acid sequence represented by amino acid numbers 461 to 947 of SEQ ID NO: 2 (or SEQ ID NO: 2), amino acid numbers 461 to 982 of SEQ ID NO: 4 (or SEQ ID NO: 4), amino acid numbers 461 to 996 of SEQ ID NO: 6 (or SEQ ID NO: 6), amino acid numbers 461 to 1043 of SEQ ID NO: 26 (or SEQ ID NO: 26), or amino acid numbers 461 to 1040 of SEQ ID NO: 28 (or SEQ ID NO: 28); or a polypeptide which has tumorigenicity and comprises an amino acid sequence having deletion, substitution, and/or insertion of 1 to 10 amino acids in the amino acid sequence represented by amino acid numbers 461 to 947 of SEQ ID NO: 2 (or SEQ ID NO: 2), amino acid numbers 461 to 982 of SEQ ID NO: 4 (or SEQ ID NO: 4), amino acid numbers 461 to 996 of SEQ ID NO: 6 (or SEQ ID NO: 6), amino acid numbers 461 to 1043 of SEQ ID NO: 26 (or SEQ ID NO: 26), or amino acid numbers 461 to 1040 of SEQ ID NO: 28 (or SEQ ID NO: 28); or (3) A polypeptide which consists of the amino acid sequence represented by SEQ ID NO: 2, SEQ ID NO: 4, SEQ ID NO: 6, SEQ ID NO: 26, or SEQ ID NO: 28.

The present invention also relates to a method for detecting genomic rearrangement of chromosomes, comprising:

(1) performing in-situ hybridization by using i) a specimen obtained from a test subject, ii) a fluorescence-labeled probe (a first probe) comprising an 5'-side of the genomic region encoding an FGFR3 gene, and iii) a fluorescence-labeled probe (a second probe) comprising a 3'-side of the genomic region encoding a TACC3 gene (herein, the fluorescence of the first probe differs from the fluorescence of the second probe), and (2) detecting superposition of signals of the label.

The present invention also relates to a method for detecting the existence of cancer (particularly, lung cancer or bladder cancer) which is positive for a fusion gene composed of an FGFR3 gene and a TACC3 gene, comprising:

(1) performing in-situ hybridization by using i) a specimen obtained from a test subject, ii) a fluorescence-labeled probe (a first probe) comprising an 5'-side of the genomic region encoding an FGFR3 gene, and iii) a fluorescence-labeled probe (a second probe) comprising a 3'-side of the genomic region encoding a TACC3 gene (herein, the fluorescence of the first probe differs from the fluorescence of the second probe), and (2) detecting superposition of signals of the label.

The present invention also relates to a method for diagnosing cancer (particularly, lung cancer or bladder cancer) which is positive for a fusion gene composed of an FGFR3 gene and a TACC3 gene, comprising:

(1) performing in-situ hybridization by using i) a specimen obtained from a test subject, ii) a fluorescence-labeled probe (a first probe) comprising an 5'-side of the genomic region encoding an FGFR3 gene, and iii) a fluorescence-labeled probe (a second label) comprising a 3'-side of the genomic region encoding a TACC3 gene (herein, the fluorescence of the first probe differs from the fluorescence of the second probe), and (2) detecting superposition of signals of the label.

Moreover, in another embodiment, the present invention relates to a method for treating cancer (particularly, lung cancer or bladder cancer) which is positive for a fusion gene composed of an FGFR3 gene and a TACC3 gene, comprising administering a substance inhibiting the polypeptide of the present invention (in an embodiment, the substance is a compound AZD4547, a compound Dovitinib, a compound BGJ398, or a compound LY2874455) to a patient diagnosed with cancer (particularly, lung cancer or bladder cancer) which is positive for a fusion gene composed of an FGFR3 gene and a TACC3 gene by the diagnosis method above.

The present invention also relates to a polypeptide according to the following (1) to (3) (hereinafter, also referred to as "polypeptide of the present invention") or a polynucleotide encoding the polypeptide (hereinafter, also referred to as "polynucleotide of the present invention"):

(1) A polypeptide which has tumorigenicity and comprises an amino acid sequence having 90% or more identity to the amino acid sequence represented by amino acid numbers 461 to 947 of SEQ ID NO: 2 (or SEQ ID NO: 2), amino acid numbers 461 to 982 of SEQ ID NO: 4 (or SEQ ID NO: 4), amino acid numbers 461 to 996 of SEQ ID NO: 6 (or SEQ ID NO: 6), amino acid numbers 461 to 1043 of SEQ ID NO: 26 (or SEQ ID NO: 26), or amino acid numbers 461 to 1040 of SEQ ID NO: 28 (or SEQ ID NO: 28);

(2) A polypeptide which has tumorigenicity and comprises the amino acid sequence represented by amino acid numbers 461 to 947 of SEQ ID NO: 2 (or SEQ ID NO: 2), amino acid numbers 461 to 982 of SEQ ID NO: 4 (or SEQ ID NO: 4), amino acid numbers 461 to 996 of SEQ ID NO: 6 (or SEQ ID NO: 6), amino acid numbers 461 to 1043 of SEQ ID NO: 26 (or SEQ ID NO: 26), or amino acid numbers 461 to 1040 of SEQ ID NO: 28 (or SEQ ID NO: 28); or a polypeptide which has tumorigenicity and comprises an amino acid sequence having deletion, substitution, and/or insertion of 1 to 10 amino acids in the amino acid sequence represented by amino acid numbers 461 to 947 of SEQ ID NO: 2 (or SEQ ID NO: 2), amino acid numbers 461 to 982 of SEQ ID NO: 4 (or SEQ ID NO: 4), amino acid numbers 461 to 996 of SEQ ID NO: 6 (or SEQ ID NO: 6), amino acid numbers 461 to 1043 of SEQ ID NO: 26 (or SEQ ID NO: 26), or amino acid numbers 461 to 1040 of SEQ ID NO: 28 (or SEQ ID NO: 28); or (3) A polypeptide which consists of the amino acid sequence represented by SEQ ID NO: 2, SEQ ID NO: 4, SEQ ID NO: 6, SEQ ID NO: 26, or SEQ ID NO: 28.

The present invention also relates to a method for detecting a fusion protein composed of FGFR3 and TACC3, comprising detecting the existence of a polypeptide according to the following (1) to (3) in a specimen obtained from a test subject:

(1) A polypeptide which has tumorigenicity and comprises an amino acid sequence having 90% or more identity to the amino acid sequence represented by amino acid numbers 461 to 947 of SEQ ID NO: 2 (or SEQ ID NO: 2), amino acid numbers 461 to 982 of SEQ ID NO: 4 (or SEQ ID NO: 4), amino acid numbers 461 to 996 of SEQ ID NO: 6 (or SEQ ID NO: 6), amino acid numbers 461 to 1043 of SEQ ID NO: 26 (or SEQ ID NO: 26), or amino acid numbers 461 to 1040 of SEQ ID NO: 28 (or SEQ ID NO: 28);

(2) A polypeptide which has tumorigenicity and comprises the amino acid sequence represented by amino acid numbers 461 to 947 of SEQ ID NO: 2 (or SEQ ID NO: 2), amino acid numbers 461 to 982 of SEQ ID NO: 4 (or SEQ ID NO: 4), amino acid numbers 461 to 996 of SEQ ID NO: 6 (or SEQ ID NO: 6), amino acid numbers 461 to 1043 of SEQ ID NO: 26 (or SEQ ID NO: 26), or amino acid numbers 461 to 1040 of SEQ ID NO: 28 (or SEQ ID NO: 28); or a polypeptide which has tumorigenicity and comprises an amino acid sequence having deletion, substitution, and/or insertion of 1 to 10 amino acids in the amino acid sequence represented by amino acid numbers 461 to 947 of SEQ ID NO: 2 (or SEQ ID NO: 2), amino acid numbers 461 to 982 of SEQ ID NO: 4 (or SEQ ID NO: 4), amino acid numbers 461 to 996 of SEQ ID NO: 6 (or SEQ ID NO: 6), amino acid numbers 461 to 1043 of SEQ ID NO: 26 (or SEQ ID NO: 26), or amino acid numbers 461 to 1040 of SEQ ID NO: 28 (or SEQ ID NO: 28); or (3) A polypeptide which consists of the amino acid sequence represented by SEQ ID NO: 2, SEQ ID NO: 4, SEQ ID NO: 6, SEQ ID NO: 26, or SEQ ID NO: 28.

The present invention also relates to a method for detecting the existence of cancer (particularly, lung cancer or bladder cancer) which is positive for a fusion protein composed of FGFR3 and TACC3, comprising detecting the existence of a polypeptide according to the following (1) to (3) in a specimen obtained from a test subject:

(1) A polypeptide which has tumorigenicity and comprises an amino acid sequence having 90% or more identity to the amino acid sequence represented by amino acid numbers 461 to 947 of SEQ ID NO: 2 (or SEQ ID NO: 2), amino acid numbers 461 to 982 of SEQ ID NO: 4 (or SEQ ID NO: 4), amino acid numbers 461 to 996 of SEQ ID NO: 6 (or SEQ ID NO: 6), amino acid numbers 461 to 1043 of SEQ ID NO: 26 (or SEQ ID NO: 26), or amino acid numbers 461 to 1040 of SEQ ID NO: 28 (or SEQ ID NO: 28);

(2) A polypeptide which has tumorigenicity and comprises the amino acid sequence represented by amino acid numbers 461 to 947 of SEQ ID NO: 2 (or SEQ ID NO: 2), amino acid numbers 461 to 982 of SEQ ID NO: 4 (or SEQ ID NO: 4), amino acid numbers 461 to 996 of SEQ ID NO: 6 (or SEQ ID NO: 6), amino acid numbers 461 to 1043 of SEQ ID NO: 26 (or SEQ ID NO: 26), or amino acid numbers 461 to 1040 of SEQ ID NO: 28 (or SEQ ID NO: 28); or a polypeptide which has tumorigenicity and comprises an amino acid sequence having deletion, substitution, and/or insertion of 1 to 10 amino acids in the amino acid sequence represented by amino acid numbers 461 to 947 of SEQ ID NO: 2 (or SEQ ID NO: 2), amino acid numbers 461 to 982 of SEQ ID NO: 4 (or SEQ ID NO: 4), amino acid numbers 461 to 996 of SEQ ID NO: 6 (or SEQ ID NO: 6), amino acid numbers 461 to 1043 of SEQ ID NO: 26 (or SEQ ID NO: 26), or amino acid numbers 461 to 1040 of SEQ ID NO: 28 (or SEQ ID NO: 28); or (3) A polypeptide which consists of the amino acid sequence represented by SEQ ID NO: 2, SEQ ID NO: 4, SEQ ID NO: 6, SEQ ID NO: 26, or SEQ ID NO: 28.

The present invention also relates to a method for diagnosing cancer (particularly, lung cancer or bladder cancer) which is positive for a fusion protein composed of FGFR3 and TACC3, comprising detecting the existence of a polypeptide according to the following (1) to (3) in a specimen obtained from a test subject:

(1) A polypeptide which has tumorigenicity and comprises an amino acid sequence having 90% or more identity to the amino acid sequence represented by amino acid numbers 461 to 947 of SEQ ID NO: 2 (or SEQ ID NO: 2), amino acid numbers 461 to 982 of SEQ ID NO: 4 (or SEQ ID NO: 4), amino acid numbers 461 to 996 of SEQ ID NO: 6 (or SEQ ID NO: 6), amino acid numbers 461 to 1043 of SEQ ID NO: 26 (or SEQ ID NO: 26), or amino acid numbers 461 to 1040 of SEQ ID NO: 28 (or SEQ ID NO: 28);

(2) A polypeptide which has tumorigenicity and comprises the amino acid sequence represented by amino acid numbers 461 to 947 of SEQ ID NO: 2 (or SEQ ID NO: 2), amino acid numbers 461 to 982 of SEQ ID NO: 4 (or SEQ ID NO: 4), amino acid numbers 461 to 996 of SEQ ID NO: 6 (or SEQ ID NO: 6), amino acid numbers 461 to 1043 of SEQ ID NO: 26 (or SEQ ID NO: 26), or amino acid numbers 461 to 1040 of SEQ ID NO: 28 (or SEQ ID NO: 28); or a polypeptide which has tumorigenicity and comprises an amino acid sequence having deletion, substitution, and/or insertion of 1 to 10 amino acids in the amino acid sequence represented by amino acid numbers 461 to 947 of SEQ ID NO: 2 (or SEQ ID NO: 2), amino acid numbers 461 to 982 of SEQ ID NO: 4 (or SEQ ID NO: 4), amino acid numbers 461 to 996 of SEQ ID NO: 6 (or SEQ ID NO: 6), amino acid numbers 461 to 1043 of SEQ ID NO: 26 (or SEQ ID NO: 26), or amino acid numbers 461 to 1040 of SEQ ID NO: 28 (or SEQ ID NO: 28); or (3) A polypeptide which consists of the amino acid sequence represented by SEQ ID NO: 2, SEQ ID NO: 4, SEQ ID NO: 6, SEQ ID NO: 26, or SEQ ID NO: 28.

Moreover, in another embodiment, the present invention relates to a method for treating cancer (particularly, lung cancer or bladder cancer) which is positive for a fusion protein composed of FGFR3 and TACC3, comprising administering a substance inhibiting the polypeptide according to (1) to (3) (in an embodiment, the substance is a compound AZD4547, a compound Dovitinib, a compound BGJ398, or a compound LY2874455) to a patient diagnosed with cancer (particularly, lung cancer or bladder cancer) which is positive for a fusion protein composed of FGFR3 and TACC3 by the diagnosis method.

An article, Science. 2012 Sep. 7; 337 (6099):1231-5, Epub 2012 Jul. 26, reported that an oncogenic fusion gene composed of an FGFR3 gene and a TACC3 gene existed, an FGFR inhibitor such as PD173074, AZD4547, or BGJ398 inhibited the proliferation of cells expressing FGFR3-TACC3 fusion gene, and the expression of FGFR3-TACC3 fusion gene may contribute to identify a group of patients with glioblastoma who benefit from the treatment with FGFR inhibitors. However, the article was published after the earliest priority date (Mar. 8, 2012) of the present application. The article describes the sequence of a gene fragment having the same fusion point as that of FGFR3-TACC3_v1 and FGFR3-TACC3_v2 of the present invention. However it does not clearly describe the full length of the sequence. Furthermore, the article neither discloses nor suggests the existence of FGFR3-TACC3_v3, FGFR3-TACC3_v5a, and FGFR3-TACC3_v5b, a method for detecting the gene, and a primer set, a probe set, and a detection kit of the present invention. Moreover, the document does not include any description or suggestion regarding lung cancer or bladder cancer.

In addition, an article, Hum Mol Genet. 2012 Nov. 21 (Hum Mol Genet. 2013 Feb. 15; 22 (4): 795-803), reported that an oncogenic fusion gene composed of FGFR3 and TACC3 (same gene as FGFR3-TACC3_v1 of the present invention) existed in bladder cancer, but the article was published after the earliest priority date (Mar. 8, 2012), at which FGFR3-TACC3_v1 in the present invention was disclosed, and the second priority date (Sep. 5, 2012) of the present application. The article neither discloses nor suggests the existence of FGFR3-TACC3_v2, FGFR3-TACC3_v3, FGFR3-TACC3_v5a, and FGFR3-TACC3_v5b, a method for detecting the gene, and a primer set, a probe set, and a detection kit of the present invention. Moreover, the article does not include description or suggestion regarding lung cancer.

In addition, an article, J Clin Invest. 2013 Feb. 1; 123 (2): 855-865, reported that several oncogenic fusion genes composed of an FGFR3 gene and a TACC3 gene existed in glioblastoma. However, the article was published after the earliest priority date (Mar. 8, 2012), at which FGFR3-TACC3_v1 and FGFR3-TACC3_v2 of the present invention were disclosed, the second priority date (Sep. 5, 2012), and the third priority date (Dec. 21, 2012) of the present application. The article neither discloses nor suggests the existence of FGFR3-TACC3_v3, FGFR3-TACC3_v5a, and FGFR3-TACC3_v5b, a method for detecting the gene, and a primer set, a probe set, and a detection kit of the present invention. Moreover, the article does not include description or suggestion regarding lung cancer or bladder cancer.

Effects of the Invention

The detection method of the present invention can be used as a method for detecting cancer (particularly, lung cancer or bladder cancer) which is positive for a fusion gene composed of an FGFR3 gene and a TACC3 gene or a fusion protein composed of FGFR3 and TACC3. Moreover, the detection method of the present invention can be used as a method for detecting genomic rearrangement of chromosomes. Furthermore, according to the detection method of the present invention, it is possible to decide whether a patient is a subject to be treated with the substance inhibiting the polypeptide of the present invention. The detection kit, the primer set, and the probe set of the present invention can be used for the detection method of the present invention. In addition, the substance inhibiting the polypeptide of the present invention can be used as a pharmaceutical composition for treating cancer (particularly, lung cancer or bladder cancer) which is positive for either a fusion gene composed of an FGFR3 gene and a TACC3 gene or a fusion protein composed of FGFR3 and TACC3.

EMBODIMENTS FOR CARRYING OUT THE INVENTION

<Detection Method of the Present Invention>

The detection method of the present invention is a method for detecting a fusion gene or a fusion protein. The method comprises detecting the existence of a specific polynucleotide or polypeptide in a specimen obtained from a test subject. As the specimen obtained from a test subject, substances collected from a test subject (specimens separated from a biological body), in particular, any type of collected tissues, body fluids (preferably blood), bronchioalveolar lavage fluids, biopsy specimens, cancer cells in urine, and sputum specimens are used. However, it is preferable to use biopsy specimens collected from the affected area of the lung or bladder of a test subject or to use sputum specimens. A genome DNA extracted from the specimens can be used, and transcription products (products generated from the genome as a result of transcription and translation; for example, mRNA, cDNA, and proteins) can be used. Particularly, it is preferable to prepare and use mRNA or cDNA. It is also possible to use a stabilized preparation obtained by fixing the specimen by using formalin and embedding it in paraffin (FFPE). Moreover, an FFPE slice obtained by cutting the FFPE into a thin slice may be used. If the FFPE slice is used, it is possible to directly detect a polynucleotide or a polypeptide existing in the slice.

In "detecting the existence of a polynucleotide" in the detection method of the fusion gene, the polynucleotide to be detected (hereinafter, referred to as a "polynucleotide as a detection target") is a "fusion gene composed of an FGFR3 gene and a TACC3 gene", and this comprises a portion of the FGFR3 gene and a portion of the TACC3 gene.

Examples of the "fusion gene composed of an FGFR3 gene and a TACC3 gene" include fusion genes comprising a sequence which encodes a kinase domain as one of the functional domains of FGFR3 and a sequence which encodes a coiled coil domain as one of the functional domains of TACC3. As cancer-causing fusion genes, PTC-RET (Clin. Cancer Res. 2009; 7119-7123), KIF5B-ALK (Clin. Cancer Res. 2009; 3143-3149), KIF5B-RET (Nature medicine 2012; Feb. 12; Epub ahead of print, Nat Med. 2012 Feb. 12; 18 (3): 375-7), EML4-ALK (Nature 2007; 561-566), and the like are known. These fusion genes are fusion genes in which genes of proteins comprising a coiled coil domain at the 5'-terminal side binds to kinase genes from which a ligand binding site at the 3'-terminal side is deleted. These fusion genes are known to cause transformation when being forcedly expressed in NIH3T3 cells. For example, 3T3 cells caused to express a KIF5B-RET fusion gene without a ligand binding site is activated by its auto-phosphorylation of the $905^{th}$ tyrosine residue which is important for ligand-independent RET kinase activation. It is known that the treatment of the cells with Vandetanib, a RET inhibitor, attenuated auto-phosphorylation of the protein and induced cell death (Nature medicine 2012; Feb. 12; Epub ahead of print, Nat Med. 2012 Feb. 12; 18 (3): 375-7). In addition, it is known that in a cell line intrinsically expressing an EML4-ALK fusion gene without ligand binding domain, phosphorylation of the $1604^{th}$ residue which is important for kinase activity of ALK occurs, and phosphorylation is inhibited by TAE684 having inhibitory activity against ALK, whereby growth of the cell is inhibited (Clin. Cancer Res. 2008; 4275-4283). Furthermore, it is suggested that Crizotinib, which is an ALK kinase inhibitor, may be an effective drug for treating patients with lung cancer expressing an EML4-ALK fusion gene (Drug Des. Devel. Ther. 2011; 471-485). As a mechanism of action of their fusion proteins encoded by those fusion genes, it is suggested that homo-dimerization through their own coiled coil domain causes ligand-independent auto-activation of the kinase domains of their fusion proteins. Moreover, it is suggested the use of an inhibitor of the fused kinase makes it possible to inhibit function of the fusion proteins as above. Therefore, it is also expected that the kinase domain of FGFR3 and the coiled coil domain of TACC3 are important domains causing cancer in the fusion gene composed of the FGFR3 gene and the TACC3 gene. Consequently, of all the fusion genes composed of the FGFR3 gene and TACC3 genes, examples of the "polynucleotide as a detection target" include polynucleotides which encode the polypeptides according to the following (1) to (3) which possess a sequence encoding the kinase domain of FGFR3 and the coiled coil domain of TACC3. In an embodiment, the existence of the polynucleotide as a detection target can also be revealed by detecting a portion within these domains thereof.

(1) A polypeptide which has tumorigenicity and comprises an amino acid sequence having 90% or more identity to the amino acid sequence represented by amino acid numbers 461 to 947 of SEQ ID NO: 2, amino acid numbers 461 to 982 of SEQ ID NO: 4, amino acid numbers 461 to 996 of SEQ ID NO: 6, amino acid numbers 461 to 1043 of SEQ ID NO: 26, or amino acid numbers 461 to 1040 of SEQ ID NO: 28 [hereinafter, referred to as a "homologous polypeptide"];

(2) A polypeptide which has tumorigenicity and comprises the amino acid sequence represented by amino acid numbers 461 to 947 of SEQ ID NO: 2, amino acid numbers 461 to 982 of SEQ ID NO: 4, amino acid numbers 461 to 996 of SEQ ID NO: 6, amino acid numbers 461 to 1043 of SEQ ID NO: 26, or amino acid numbers 461 to 1040 of SEQ ID NO: 28; or a polypeptide which has tumorigenicity and comprises an amino acid sequence having deletion, substitution, and/or insertion of 1 to 10 amino acids in the amino acid sequence represented by amino acid numbers 461 to 947 of SEQ ID NO: 2, amino acid numbers 461 to 982 of SEQ ID NO: 4, amino acid numbers 461 to 996 of SEQ ID NO: 6, amino acid numbers 461 to 1043 of SEQ ID NO: 26, or amino acid numbers 461 to 1040 of SEQ ID NO: 28 [hereinafter, referred to as a "polypeptide as a functionally equivalent variant"; or (3) A polypeptide which consists of the amino acid sequence represented by SEQ ID NO: 2, SEQ ID NO: 4, SEQ ID NO: 6, SEQ ID NO: 26, or SEQ ID NO: 28.

Preferable examples of the polynucleotide as a detection target comprise polynucleotides encoding the polypeptides according to the following (1) to (3):

(1) A polypeptide which has tumorigenicity and comprises an amino acid sequence having 90% or more identity to the amino acid sequence represented by SEQ ID NO: 2, SEQ ID NO: 4, SEQ ID NO: 6, SEQ ID NO: 26, or SEQ ID NO: 28;

(2) A polypeptide which has tumorigenicity and comprises the amino acid sequence represented by SEQ ID NO: 2, SEQ ID NO: 4, SEQ ID NO: 6, SEQ ID NO: 26, or SEQ ID NO: 28; or a polypeptide which has tumorigenicity and comprises an amino acid sequence having deletion, substitution, and/or insertion of 1 to 10 amino acids in the amino acid sequence represented by SEQ ID NO: 2, SEQ ID NO: 4, SEQ ID NO: 6, SEQ ID NO: 26, or SEQ ID NO: 28; or (3) A polypeptide which consists of the amino acid sequence represented by SEQ ID NO: 2, SEQ ID NO: 4, SEQ ID NO: 6, SEQ ID NO: 26, or SEQ ID NO: 28.

More preferable examples of the polynucleotide as a detection target include polynucleotides comprising the nucleotide sequence represented by SEQ ID NO: 1, SEQ ID NO: 3, SEQ ID NO: 5, SEQ ID NO: 25, or SEQ ID NO: 27.

The polynucleotide consisting of the nucleotide sequence represented by SEQ ID NO: 1 is a polynucleotide consisting of the nucleotide sequence from nucleotide positions 257 (corresponding to the first methionine on exon 2) to 2536 (corresponding to the 3'-terminal of exon 18) of the FGFR3 gene variant 3 (GenBank accession number: NM 001163213.1) and the nucleotide sequence from nucleotide positions 2050 (corresponding to the 5'-terminal of exon 11) to 2625 (corresponding to the stop codon on exon 16) of the TACC3 gene (GenBank accession number: NM_006342.1). In the nucleotide sequence represented by SEQ ID NO: 1, the sequence from nucleotide positions 1 to 2280 is derived from the FGFR3 gene, and the sequence from nucleotide positions 2281 to 2856 is derived from the TACC3 gene. This fusion polynucleotide is designated as FGFR3-TACC3_v1. The nucleotide positions 1 to 2856 of SEQ ID NO: 1 form an open reading frame (ORF) of a fusion protein, and the amino acid sequence encoded by the ORF is shown in SEQ ID NO: 2.

The polynucleotide consisting of the nucleotide sequence represented by SEQ ID NO: 3 is a polynucleotide consisting of the nucleotide sequence from nucleotide positions 257 (corresponding to the first methionine on exon 2) to 2536 (corresponding to the 3'-terminal of exon 18) of the FGFR3 gene variant 3 (GenBank accession number: NM_001163213.1) and the nucleotide sequence from nucleotide positions 1945 (corresponding to the 5'-terminal of exon 10) to 2625 (corresponding to the stop codon on exon 16) of the TACC3 gene (GenBank accession number: NM_006342.1). In the nucleotide sequence represented by SEQ ID NO: 3, the sequence from nucleotide positions 1 to 2280 is derived from the FGFR3 gene, and the sequence from nucleotide positions 2281 to 2961 is derived from the TACC3 gene. This fusion polynucleotide is designated as FGFR3-TACC3_v2. The nucleotide positions 1 to 2961 of SEQ ID NO: 3 form an ORF of a fusion protein, and the amino acid sequence encoded by the ORF is shown in SEQ ID NO: 4.

The polynucleotide consisting of the nucleotide sequence represented by SEQ ID NO: 5 is a polynucleotide consisting of the nucleotide sequence from nucleotide positions 257 (corresponding to the first methionine on exon 2) to 2624 (corresponding to the middle of exon 19) of the FGFR3 gene variant 3 (GenBank accession number: NM_001163213.1), the nucleotide sequence from nucleotide positions 2050 (corresponding to the 5'-terminal of exon 11) to 2625 (corresponding to the stop codon on exon 16) of the TACC3 gene (GenBank accession number: NM_006342.1), and 59 bases of intron of the TACC3 gene intervening between the sequences. In the nucleotide sequence represented by SEQ ID NO: 5, the sequence from nucleotide positions 1 to 2368 is derived from the FGFR3 gene, the sequence from nucleotide positions 2369 to 2427 is derived from the genome sequence of the TACC3 region, and the sequence from nucleotide positions 2428 to 3003 is derived from the TACC3 gene. This fusion polynucleotide is designated as FGFR3-TACC3_v3. The nucleotide positions 1 to 3003 of the SEQ ID NO: 5 form an ORF of a fusion protein, and the amino acid sequence encoded by the ORF is shown in SEQ ID NO: 6.

The polynucleotide consisting of the nucleotide sequence represented by SEQ ID NO: 25 is a polynucleotide consisting of the nucleotide sequence from nucleotide positions 257 to 2498 (here, the 1980$^{th}$ base is not C but G) of the FGFR3 gene variant 3 (GenBank accession number: NM_001163213.1) and the nucleotide sequence from nucleotide positions 1771 to 2672 of the TACC3 gene (GenBank accession number: NM_006342.1). In the nucleotide sequence represented by SEQ ID NO: 25, the sequence from nucleotide positions 1 to 2242 is derived from the FGFR3 gene, and the sequence from nucleotide positions 2243 to 3144 is derived from the TACC3 gene. This fusion polynucleotide is designated as FGFR3-TACC3_v5a. The nucleotide positions 1 to 3144 of SEQ ID NO: 25 form an ORF of a fusion protein, and the amino acid sequence encoded by the ORF is shown in SEQ ID NO: 26.

The polynucleotide consisting of the nucleotide sequence represented by SEQ ID NO: 27 is a polynucleotide consisting of the nucleotide sequence from nucleotide positions 257 to 2498 of the FGFR3 gene variant 3 (GenBank accession number: NM_001163213.1) and the nucleotide sequence from nucleotide positions 1771 to 2672 of the TACC3 gene (GenBank accession number: NM_006342.1). Herein, deletion and insertion has occurred in a fraction of the polynucleotide. The deleted region corresponds to nucleotide position from the 690$^{th}$ base to the 701$^{st}$ base (sequence of the 3' side of exon 4) of the FGFR3 gene (NM_001163213.1). The insertion point corresponds to that between the 1528$^{th}$ base and the 1529$^{th}$ base (between exon 10 and exon 11) of the FGFR3 gene (NM_001163213.1), and the insert sequence is CAG In the nucleotide sequence represented by SEQ ID NO: 27, the sequence of nucleotide positions 1 to 2233 is derived from the FGFR3 gene, and sequence of nucleotide positions 2234 to 3135 is derived from the TACC3 gene. This fusion polynucleotide is designated as FGFR3-TACC3_v5b. The nucleotide positions 1 to 3135 of SEQ ID NO: 28 form an ORF of a fusion protein, and the amino acid sequence encoded by the ORF is shown in SEQ ID NO: 28.

FGFR3-TACC3_v1, FGFR3-TACC3_v2, FGFR3-TACC3_v3, FGFR3-TACC3_v5a, and FGFR3-TACC3_v5b are collectively designated as FGFR3-TACC3 fusion polynucleotides.

Examples of the polynucleotide as a detection target in another embodiment include a partial sequence of FGFR3-

TACC3_v1 corresponding to nucleotide positions 1381 to 2841 of SEQ ID NO: 1, a partial sequence of FGFR3-TACC3_v2 corresponding to nucleotide positions 1381 to 2946 of SEQ ID NO: 3, FGFR3-TACC3_v3 corresponding to nucleotide positions 1381 to 2988 of SEQ ID NO: 5, and the like.

Preferable examples of the "homologous polypeptide" include the "polypeptide which has tumorigenicity and comprises an amino acid sequence having 90% or more identity to the amino acid sequence represented by SEQ ID NO: 2, SEQ ID NO: 4, SEQ ID NO: 6, SEQ ID NO: 26, or SEQ ID NO: 28". However, as the homologous polypeptide, a polypeptide which comprises an amino acid sequence more preferably having 95% or more identity and even more preferably having 98% or more identity is particularly preferable.

As the preferable "functionally equivalent variant polypeptide", the "polypeptide which has tumorigenicity and comprises an amino acid sequence having deletion, substitution, and/or insertion of 1 to 10 amino acids, preferably 1 to several amino acids, more preferably 1 to 7 amino acids, and most preferably 1 to 5 amino acids in the amino acid sequence represented by SEQ ID NO: 2, SEQ ID NO: 4, SEQ ID NO: 6, SEQ ID NO: 26, or SEQ ID NO: 28" is preferable, and the "polypeptide which has tumorigenicity and comprises the amino acid sequence represented by SEQ ID NO: 2, SEQ ID NO: 4, SEQ ID NO: 6, SEQ ID NO: 26, or SEQ ID NO: 28" is particularly preferable.

In the present specification, the "identity" means Identity which is a value obtained from NEEDLE program (J Mol Biol 1970; 48: 443-453) search using default parameters. The parameters are as follows.

Gap penalty=10
Extend penalty=0.5
Matrix=EBLOSUM62

Whether a certain polypeptide has "tumorigenicity" is confirmed by the method described in Example 8 described below. In particular, the method includes steps of introducing the corresponding fusion gene into NIH3T3 cells and confirming anchorage-independent growth potential of the cells by using a plate for spheroid culture. Moreover, tumorigenicity could be confirmed with a method including steps of inoculating cell expressing the fusion gene into the skin of nude mouse and confirming the formation of a tumor for a certain period of time.

For the polynucleotide as a detection target in the detection method of the present invention, a polynucleotide encoding the "polypeptide which has tumorigenicity and comprises the amino acid sequence represented by SEQ ID NO: 2, SEQ ID NO: 4, SEQ ID NO: 6, SEQ ID NO: 26, or SEQ ID NO: 28" is preferable, and a polynucleotide encoding the "polypeptide which consists of the amino acid sequence represented by SEQ ID NO: 2, SEQ ID NO: 4, SEQ ID NO: 6, SEQ ID NO: 26, or SEQ ID NO: 28" is most preferable.

The "detecting the existence of a polynucleotide" in the method for detecting a fusion gene of the present invention is performed by detecting the existence of the polynucleotide as a detection target (a genome sequence comprising a fusion point) in the genome of a specimen obtained from a test subject, detecting the existence of a transcription product (for example, mRNA or cDNA) corresponding to the polynucleotide as a detection target derived from the genome DNA by extracting products from a specimen obtained from a test subject, or as necessary, detecting the existence of the polynucleotide as a detection target in a pretreated specimen obtained from a test subject by in-situ hybridization.

To extract a genome DNA can be performed by publicly known methods and can be performed easily using a commercially available kit for DNA extraction.

The detection step can be performed according to publicly known methods for genetic analysis (for example, well-known methods which are commonly used for gene detection methods, such as PCR, Ligase chain reaction (LCR), Strand displacement amplification (SDA), Nucleic acid sequence-based amplification (NASBA), Isothermal and chimeric primer-initiated amplification of nucleic acids (ICAN), a Loop-mediated isothermal amplification (LAMP) method, a TMA method (Gen-Probe's TMA system), in-situ hybridization (ISH) method, and microarray). For example, a hybridization technique in which a nucleic acid to be hybridized with the polynucleotide as a detection target is used as a probe, gene amplification technique in which DNA to be hybridized with the polynucleotide as a detection target is used as a primer, and the like are used.

In particular, the detection is performed using a nucleic acid, for example, mRNA derived from a specimen obtained from a test subject. The amount of mRNA is measured by a gene amplification reaction method by using a primer designed to be able to specifically amplify the polynucleotide as a detection target. The primer used in the detection method of the present invention, or the primer comprised in the detection kit is not particularly limited as long as the primer can specifically amplify the polynucleotide as a detection target. The primer is designed based on the nucleotide sequence of the polynucleotide as a detection target. For designing a primer used in a PCR amplification monitoring method, primer design software (for example, Primer Express; Applied Biosystems) and the like can be used. The greater the size of the PCR product is, the poorer the amplification efficiency becomes. Accordingly, it is appropriate to design a sense primer and an antisense primer such that the size of the amplification product obtained by amplification of mRNA or cDNA becomes up to 1 kb.

More specifically, a sense primer (5'-primer) is designed from a portion derived from the FGFR3 gene (for example, any portion within the domain of the FGFR3 gene of the fusion polynucleotide (particularly cDNA)), and an antisense primer (3'-primer) is designed from a portion derived from the TACC3 gene (for example, any portion within the domain of the TACC3 gene of the fusion polynucleotide (particularly, cDNA)). Alternatively, either the sense primer or the antisense primer may be designed such that it corresponds to the region comprising a fusion point (described later) of the fusion polynucleotide. It is preferable to use the primer set comprised in the detection kit of the present invention, and it is more preferable to use the primer set which is most preferably comprised in the detection kit of the present invention. In the PCR amplification monitoring method, if the sense primers corresponding to the respective genes are mixed together, it is possible to design multiplex PCR method to detect all polynucleotides as detection targets in a single reaction liquid. By the method suitable for each of the amplification techniques, it is possible to confirm whether a target gene (full length or partial) has been amplified. For instance, in the PCR method, it is possible to examine whether fragments with intended size would be amplified by agarose gel electrophoresis and ethidium bromide staining, or the like. If amplified fragments with intended size have been obtained, it could be concluded that the polynucleotide as a detection target exists in the specimen obtained from a test subject. The existence of the polynucleotide as a detection target can be detected in this way.

In addition to detecting the existence of a specific polynucleotide in a specimen obtained from a test subject by a gene amplification reaction, the method for detecting a fusion gene of the present invention preferably further comprises steps to test whether amplified fragments have an intended size.

For the detection utilizing the hybridization technique, for example, northern hybridization, a dot blotting method, a DNA microarray method, an RNA protection method, and the like are used. For the probe used for the hybridization, it is possible to use a nucleic acid molecule consisting of at least 32 consecutive bases hybridized with the polynucleotide as a detection target or a complementary strand thereof under stringent conditions (preferably more stringent conditions) and has a sequence comprising 16 bases at each of the upstream and downstream sides with the fusion point as a center (in particular, the sequence comprises the $2265^{th}$ base to the $2296^{th}$ base (the $2280^{th}$ base/the $2281^{st}$ base) of the nucleotide sequence represented by SEQ ID NO: 1, the $2265^{th}$ base to the $2296^{th}$ base (the $2280^{th}$ base/the $2281^{st}$ base) of the nucleotide sequence represented by SEQ ID NO: 3, the $2353^{rd}$ base to the $2384^{th}$ base (the $2368^{th}$ base/the $2369^{th}$ base) of the nucleotide sequence represented by SEQ ID NO: 5, the $2227^{th}$ base to the $2258^{th}$ base (the $2242^{nd}$ base/the $2243^{rd}$ base) of the nucleotide sequence represented by SEQ ID NO: 25, or the $2218^{th}$ base to the $2249^{th}$ base (the $2233^{rd}$ base/the $2234^{th}$ base) of the nucleotide sequence represented by SEQ ID NO: 27; herein, the number of base in the parenthesis indicates a fusion point) or a complementary strand thereof.

In the present specification, the "fusion point" means a point at which a portion derived from the FGFR3 gene has been fused with a portion derived from the TACC3 gene.

The detection utilizing the in-situ hybridization technique can be performed according to a publicly known FISH method (fusion assay). Alternatively, the detection can be performed by a fusion assay as a combination of a chromogenic in-situ hybridization (CISH) method and a silver in-situ hybridization (SISH) method.

The detection utilizing the in-situ hybridization technique can be performed according to a publicly known RNA FISH method (J. Mol. Diagn. 2012; 22-29). More specifically, a detection probe is designed from a portion derived from the FGFR3 gene (for example, any portion within the region of the FGFR3 gene of the fusion polynucleotide (mRNA)), and the other detection probe is designed from a portion derived from the TACC3 gene (for example, any portion within the region of the TACC3 gene of the fusion polynucleotide (mRNA)). The specimen obtained from a test subject is hybridized with the probe, signals are amplified by using a reagent for signal amplification, and superposition of the signals from the portion derived from the FGFR3 gene and the signal from the portion derived from the TACC3 gene are detected. By using different fluorogenic and chromogenic substrates for detecting the probe designed from a portion derived from the FGFR3 gene and the probe designed from a portion derived from the TACC3 gene, it is possible to observe whether the two types of probes derived from different genes are in the same place (on the same molecule). By observing a state in which the two types of probes are in the same place (on the same molecule), it is possible to detect the existence of the polynucleotide as a detection target. As the reagent for signal amplification, it is possible to use PreAmplifier Mix QT (Affymetrix, Inc.), Amplifier Mix QT (Affymetrix, Inc.), Label Probe Mix (Affymetrix, Inc.), and Label Probe Diluent QT (Affymetrix, Inc.).

In the present specification, the term "stringent conditions" indicates those of "5×SSPE, 5×Denhardt's solution, 0.5% sodium dodecyl sulfate (SDS), 50% formamide, 200 µg/mL salmon sperm DNA, and overnight incubation at 42° C." as for hybridization, and those of "0.5×SSC, 0.1% SDS, and 42° C." as for washing. The term "more stringent conditions" indicates those of "5×SSPE, 5×Denhardt's solution, 0.5% SDS, 50% formamide, 200 µg/mL salmon sperm DNA, and overnight incubation at 42° C." as for hybridization, and those of "0.2×SSC, 0.1% SDS, and 65° C." as for washing.

Moreover, a gene amplification technique such as RT-PCR can be used. In the RT-PCR method, it is possible to analyze the existence of the polynucleotide as a detection target more quantitatively with a PCR amplification monitoring method (real time PCR method) (Genome Res., 6 (10), 986, 1996) in the process of amplifying a gene. For the PCR amplification monitoring method, for example, ABI PRISM7900 (Applied Biosystems) can be used. The real time PCR method is a publicly known method, and instruments and kits for the method are commercially available. Therefore the real time PCR can be simply performed using these materials.

In the present invention, the detection of a fusion gene or a fusion protein can be performed by directly detecting the existence of a polypeptide encoded by the polynucleotide as a detection target (hereinafter, referred to as a "polypeptide as a detection target") in a specimen obtained from a test subject. The "fusion protein composed of FGFR3 and TACC3" is a polypeptide encoded by the polynucleotide as a detection target (that is, the polypeptide as a detection target). Among polypeptides as a detection target, a polypeptide comprising the amino acid sequence represented by SEQ ID NO: 2 is designated as FGFR3-TACC3 fusion polypeptide v1; a polypeptide comprising the amino acid sequence represented by SEQ ID NO: 4 is designated as FGFR3-TACC3 fusion polypeptide v2; a polypeptide comprising the amino acid sequence represented by SEQ ID NO: 6 is designated as FGFR3-TACC3 fusion polypeptide v3; a polypeptide comprising the amino acid sequence represented by SEQ ID NO: 26 is designated as FGFR3-TACC3 fusion polypeptide v5a; and a polypeptide comprising the amino acid sequence represented by SEQ ID NO: 28 is designated as FGFR3-TACC3 fusion polypeptide v5b. The FGFR3-TACC3 fusion polypeptide v1, the FGFR3-TACC3 fusion polypeptide v2, the FGFR3-TACC3 fusion polypeptide v3, the FGFR3-TACC3 fusion polypeptide v5a, and the FGFR3-TACC3 fusion polypeptide v5b are collectively designated as FGFR3-TACC3 fusion polypeptides (FGFR3-TACC3 fusion proteins).

For example, in the steps of detecting the polypeptide as a detection target, the detection may be performed by a method as a combination of immunoassay and enzymatic activity assay, in which a lysate derived from a specimen obtained from a test subject (for example, a cancer tissue or cancer cells obtained from a test subject) is prepared, and the polypeptide as a detection target contained in the lysate is combined with antibodies against the respective proteins constituting the fusion polypeptide (for example, an anti-FGFR3 antibody and an anti-TACC3 antibody). Furthermore, the detection may be performed by an immunohistochemical staining technique in which the polypeptide as a detection target contained in a specimen (for example, an FFPE slice) obtained from a test subject which has undergone pretreatment (for example, removal of paraffin) as appropriate is combined with antibodies against the respective proteins constituting the fusion polypeptide (for example, an anti-FGFR3 antibody and an anti-TACC3 antibody). Examples of these techniques include enzymatic immunoassay, double antibody sandwich ELISA, fluorescence immunoassay, radioimmunoassay, western blotting, and immunohistochemical staining, in which a monoclonal antibody or a polyclonal antibody specific to the polypeptide as a detection target is used.

The detection utilizing immunohistochemical staining technique can be performed according to Proximity Ligation Assay (Nat. Methods. 2006; 995-1000) which is a publicly known technique of specifically detecting a polypeptide of interest with a single molecule as a unit. More specifically, by using an antibody recognizing the portion derived from the FGFR3 gene of the fusion polypeptide and an antibody recognizing the portion derived from the TACC3 gene of the fusion polypeptide, a state in which the two antibodies have recognized the same molecule is detected by the aforementioned technique, whereby the existence of the polypeptide as a detection target can be detected. To be more specific, the detection can be performed by i) bringing an antibody (primary antibody) which recognizes the portion derived from the FGFR3 gene of the fusion polypeptide and an antibody (primary antibody) which recognizes the portion derived from the TACC3 gene of the fusion polypeptide into contact with a specimen obtained from a test subject, ii) adding secondary antibodies which are conjugated with oligonucleotides and respectively bind to the primary antibodies, iii) causing a ligation reaction by adding a ligation solution containing two kinds of oligonucleotides which are partially complementary to the oligonucleotides conjugated with the secondary antibodies and a ligase which can form a cyclic structure between the secondary antibodies by causing ligation reaction when the two kinds of oligonucleotides come close to each other, iv) a elongating a nucleic acid sequence along the formed cyclic structure, v) hybridizing labeled oligonucleotides probe which can be hybridized with the elongated nucleic acid sequence, and vi) detecting signals of the label. In an embodiment, it is possible to use a PLA probe and reagents included a Duolink II reagent kit and a Duolink II Bright field reagent kit (Olink Bioscience).

When the polynucleotide as a detection target or the polypeptide as a detection target in the detection method of the present invention is detected from a specimen obtained from a test subject, this means that the test subject is a subject (patient) with cancer which is positive for either the polynucleotide or the polypeptide and a subject to be treated with a substance inhibiting the polypeptide of the present invention (in an embodiment, the substance is a compound AZD4547, a compound Dovitinib, a compound BGJ398, or a compound LY2874455).

<Detection Kit of the Present Invention, Primer Set of the Present Invention, and Probe Set of the Present Invention>

The detection kit of the present invention which comprises a primer set comprises at least a sense primer and an antisense primer (also referred to as a "primer set") designed to be able to specifically amplify the polynucleotide as a detection target in the detection method of the present invention. The primer set of the present invention is a set of polynucleotides functioning as primers for amplifying the polynucleotide as a detection target.

The primer set of the present invention comprises a primer set for detecting a fusion gene composed of the FGFR3 gene and the TACC3 gene, comprising a sense primer designed from a portion derived from the FGFR3 gene and an antisense primer designed from a portion derived from the TACC3 gene, in which the antisense primer consists of nucleic acid molecules (preferably nucleic acid molecules of at least 16 bases) hybridized with the "polynucleotide as a detection target" under stringent conditions (preferably under more stringent conditions), and the sense primer consists of nucleic acid molecules (preferably nucleic acid molecules of at least 16 bases) hybridized with a complementary strand of the "polynucleotide as a detection target" under stringent conditions (preferably under more stringent conditions).

In the primer set of the present invention, either the sense primer or the antisense primer may be designed such that it corresponds to the portion comprising the fusion point (aforementioned) of the fusion polynucleotide.

Examples of specific embodiments of the primer set of the present invention include a primer set selected from a group consisting of the following (1) to (5):

(1) A primer set of a sense primer consisting of an oligonucleotide of at least any consecutive 16 bases between nucleotide positions 1 and 2280 of SEQ ID NO: 1 and an antisense primer consisting of an oligonucleotide complementary to an oligonucleotide of at least any consecutive 16 bases between nucleotide positions 2281 and 2856 of SEQ ID NO: 1.

(2) A primer set of a sense primer consisting of an oligonucleotide of at least any consecutive 16 bases between nucleotide positions 1 and 2280 of SEQ ID NO: 3 and an antisense primer consisting of an oligonucleotide complementary to an oligonucleotide of at least any consecutive 16 bases between nucleotide positions 2281 and 2961 of SEQ ID NO: 3.

(3) A primer set of a sense primer consisting of an oligonucleotide of at least any consecutive 16 bases between nucleotide positions 1 and 2368 of SEQ ID NO: 5 and an antisense primer consisting of an oligonucleotide complementary to an oligonucleotide of at least any consecutive 16 bases between nucleotide positions 2369 and 3003 of SEQ ID NO: 5.

(4) A primer set of a sense primer consisting of an oligonucleotide of at least any consecutive 16 bases between nucleotide positions 1 and 2242 of SEQ ID NO: 25 and an antisense primer consisting of an oligonucleotide complementary to an oligonucleotide of at least any consecutive 16 bases between nucleotide positions 2243 and 3144 of SEQ ID NO: 25.

[16] A primer set of a sense primer consisting of an oligonucleotide of at least any consecutive 16 bases between nucleotide positions 1 and 2233 of SEQ ID NO: 27 and an antisense primer consisting of an oligonucleotide complementary to an oligonucleotide of at least any consecutive 16 bases between nucleotide positions 2234 and 3135 of SEQ ID NO: 27.

In the primer set, distance between selected positions for the sense primer and the antisense primer is preferably up to 1 kb, or the size of the product amplified by the sense primer and the antisense primer is preferably up to 1 kb.

Furthermore, the primer of the present invention generally has a length of 15 to 40 bases, preferably has a length of 16 to 24 bases, more preferably has a length of 18 to 24 bases, and particularly preferably has a length of 20 to 24 bases.

The primer set of the present invention can be used for amplifying and detecting the polynucleotide as a detection target in the detection method of the present invention.

In addition, each of the primers comprised in the primer set of the present invention is not particularly limited, and for example, can be prepared by a chemical synthesis method.

The detection kit comprising the probe set of the present invention comprises at least a probe set designed from a portion derived from the FGFR3 gene (for example, any portion within the region of the FGFR3 gene of the fusion polynucleotide (mRNA)) and a probe set designed from a portion derived from the TACC3 gene (for example, any portion within the region of the TACC3 gene of the fusion polynucleotide (mRNA)), which have been designed so as to be able to be specifically hybridized with the polynucleotide as a detection target in the detection method of the present invention (also referred to as a "probe set"), and a reagent amplifying the hybridized signal. The probe set is a collection of polynucleotides functioning as a probe set hybridized with the polynucleotide as a detection target.

The probe set of the present invention comprises a probe set which comprises a probe designed from a portion derived from the FGFR3 gene (for example, any portion within the region of the FGFR3 gene of the fusion polynucleotide (mRNA)) and a probe designed from a portion derived from the TACC3 gene (for example, any portion within the region of the TACC3 gene of the fusion polynucleotide (mRNA)) and is for detecting the fusion gene composed of the FGFR3 gene and the TACC3 gene, in which each of the probes consists of nucleic acid molecules hybridized with the "polynucleotide as a detection target". In an embodiment, each of the probes is a branched DNA probe, and the branched DNA probe based on the sequence information is available from Affymetrix, Inc.

Examples of specific embodiments of the probe set of the present invention include probe sets selected from a group consisting of the following (1) to (3):

(1) Probe sets comprising multiple kinds of probe sets (preferably comprising 20 kinds of probe sets) consisting of probe pairs which are adjacent to each other and comprise oligonucleotides complementary to at least any consecutive 16 bases between nucleotide positions 1 and 2280 of SEQ ID NO: 1, and probe sets comprising multiple kinds of probe sets (preferably comprising 20 kinds of probe sets) consisting of probe pairs which are adjacent to each other and comprise oligonucleotides complementary to at least any consecutive 16 bases between nucleotide positions 2281 and 2856 of SEQ ID NO: 1.

(2) Probe sets comprising multiple kinds of probe sets (preferably comprising 20 kinds of probe sets) consisting of probe pairs which are adjacent to each other and comprise oligonucleotides complementary to at least any consecutive 16 bases between nucleotide positions 1 and 2280 of SEQ ID NO: 3, and probe sets comprising multiple kinds of probe sets (preferably comprising 20 kinds of probe sets) consisting of probe pairs which are adjacent to each other and comprise oligonucleotides complementary to at least any consecutive 16 bases between nucleotide positions 2281 and 2961 of SEQ ID NO: 3.

(3) Probe set comprising multiple kinds of probe sets (preferably comprising 20 kinds of probe sets) consisting of probe pairs which are adjacent to each other and comprise oligonucleotides complementary to at least any consecutive 16 bases between nucleotide positions 1 and 2368 of SEQ ID NO: 5, and probe sets comprising multiple kinds of probe sets (preferably comprising 20 kinds of probe sets) consisting of probe pairs which are adjacent to each other and comprise oligonucleotides complementary to at least any consecutive 16 bases between nucleotide positions 2369 and 3003 of SEQ ID NO: 5.

Herein, the more probe sets consisting of probe pairs which are adjacent to each other make it easier to obtain signals, and are preferable. In an embodiment, approximately 20 kinds of probe sets are used.

The probe set of the present invention can be used for detecting the polynucleotide as a detection target in the detection method of the present invention. Each of the probes comprised in the probe set of the present invention is not particularly limited, and for example, can be prepared by a chemical synthesis method.

<Pharmaceutical Composition for Treating Cancer which is Positive for Either Polynucleotide of the Present Invention or Polypeptide of the Present Invention>

The fusion polynucleotides isolated and identified from the specimens of the patients with cancer (Examples 1 to 3) were found to be cancer-causing genes (Examples 8 and 11), and the existence of the fusion polynucleotides was detected in a portion of the patients with lung cancer or bladder cancer (Examples 4 to 6). Furthermore, based on new findings revealed by the present inventors and showing that inhibition of the activity and/or expression of the polypeptide of the present invention suppressed anchorage-independent proliferating potential of cells (that is, it demonstrated anti-cancer activity) (Examples 9, 12, 13, 14, and 16), it is expected that a substance inhibiting the polypeptide of the present invention (inhibiting the activity and/or expression of the polypeptide of the present invention) exerts an effect of treating cancer which is positive for either the polynucleotide of the present invention or the polypeptide of the present invention.

The present invention includes a pharmaceutical composition for treating cancer which is positive for either the polynucleotide of the present invention or the polypeptide of the present invention, comprising, as an active ingredient, a substance inhibiting the polypeptide of the present invention (for example, a substance [for example, a double-stranded nucleic acid (including siRNA), a protein (including an antibody or an antibody fragment), a peptide, or a compound other than these] obtained by any of the methods for screening the active ingredient of the pharmaceutical composition described later).

The active ingredient in the pharmaceutical composition of the present invention can be selected by the method for screening the active ingredient of the pharmaceutical composition described later. Examples of the active ingredient include Dovitinib (a compound described in Clinical Cancer Research 2011; 17: 7451-7461, 4-amino-5-fluoro-3-[6-(4-methylpiperazin-1-yl)-1H-benzo[d]imidazol-2-yl]quinoline-2(1H)-one), AZD4547 (a compound described in WO2008075068 Example 154 and AACR2011, poster 3568; title: "Characterization of AZD4547: An orally bio-available, potent and selective inhibitor of FGFR tyrosine kinase 1, 2, and 3", N-{5-[2-(3,5-dimethoxyphenyl)ethyl]-2H-pyrazol-3-yl}-4-[(3R,5S)-3,5-dimethylpiperazin-1-yl] benzamide), and BGJ398 (a compound described in Journal of Medicinal Chemistry 2011; 54; 7066-7083, 3-(2,6-dichloro-3,5-dimethoxy-phenyl)-1-{6-[4-(4-ethyl-piperazin-1-yl), which are compounds described in Example 9 described below, and LY2874455 (WO2010129509 Example 1; Mol Cancer Ther, 2011, 10, 2200-2210; (R)-(E)-2-{4-[2-{5-[1-(3,5-dichloropyridin-4-yl)ethoxy]-1H-indazol-3-yl}vinyl]-1H-pyrazol-1-yl}ethanol) which is a compound described in Example 21. The examples also include 5-[(2,6-difluoro-3,5-dimethoxybenzyl)oxy]-N-{3-methoxy- 4-[4-(4-methylpiperazin-1-yl)piperidin-1-yl]phenyl pyrimidin-2-amine (Compound A), 2-[4-({5-[2,6-difluoro-3,5-dimethoxybenzyl]oxy}pyrimidin-2-yl}amino)-1H-pyrazol-1-yl]ethanol (Compound B), (2R)-3-[4-({5-[(2,6-difluoro-3,5-dimethoxybenzyl)oxy]pyrimidin-2-yl}amino)-1H-pyrazol-1-yl]propane-1,2-diol (Compound C), 5-[(2,6-difluoro-3,5-dimethoxybenzyl)oxy]-N-[4-(4-methylpiperazin-1-yl)phenyl]pyrimidin-2-amine (Compound D), and 5-[(2,6-difluoro-3,5-dimethoxybenzyl)oxy]-N-{1-methyl-5-[(4-methylpiperazin-1-yl)methyl]-1H-pyrazol-3-yl}pyrimidin-2-amine (Compound E) which are compounds described in Preparation Examples 1 to 5 and Examples 29 and 30.

In addition, a compound selected from among publicly known low-molecular weight compounds having inhibitory activity against FGFR3 (FGFR3 inhibitors) by the method for screening the active ingredient of the pharmaceutical composition, described later, can be used as an active ingredient in the pharmaceutical composition of the present invention. Particularly, examples of the compound include a compound AZD4547, a compound Dovitinib, a compound BGJ398, and a compound LY2874455.

The double-stranded nucleic acid exemplified as the active ingredient of the pharmaceutical composition of the present invention includes the portion of double-stranded nucleic acid (RNA or DNA) and preferably 3'-terminal overhangs of a sense strand and an antisense strand, which induces RNAi. RNAi is a phenomenon that has been evolutionarily conserved and occurs through the double-stranded nucleic acid consisting of 21 to 23 bases generated by an RNase III endonuclease (Genes Dev. 15, 485-490, 2001). Each of the 3'-side overhangs is any nucleic acid consisting of 1 or 2 bases, but it is preferably a nucleic acid consisting of 2 bases. Herein, the number of the bases (21 to 23 bases) is the total length of either the sense strand or the antisense strand comprising the overhangs. Moreover, the number of the bases forming the sense strand and the number of bases forming the antisense strand can be the same as or different from each other, but the numbers are preferably the same as each other.

For a ribonucleotide constituting the 3'-side overhang of the double-stranded nucleic acid, for example, U (uridine), A (adenosine), G (guanosine), or C (cytidine) can be used. As a deoxyribonucleotide constituting the 3'-side overhang, for example, dT (deoxythymidine), dA (deoxyadenosine), dG (deoxyguanosine), or dC (deoxycytidine) can be used.

The double-stranded nucleic acid which can be used as an active ingredient of the pharmaceutical composition of the present invention is a double-stranded nucleic acid in which the double-stranded portion is designed based on the bases of SEQ ID NO: 1, SEQ ID NO: 3, and SEQ ID NO: 5 and which exhibits inhibitory activity against expression of the polypeptide of the present invention.

A preparation which comprises, as an active ingredient, a substance inhibiting the polypeptide of the present invention (for example, a substance obtained by the method for screening the active ingredient of the pharmaceutical composition described later [for example, a double-stranded nucleic acid, a protein (including an antibody or an antibody fragment), a peptide, or a compound other than these]) can be prepared as a pharmaceutical composition by using a carrier, an excipient, and/or other additives which are generally used for making the preparation and are pharmaceutically accepted, according to the type of the active ingredient.

Examples of the mode of administration of the pharmaceutical composition include oral administration using a tablet, a pill, a capsule, granules, fine granules, powder, or an oral solution or parenteral administration using an injection for intravenous injection (including intravenous drip), intramuscular injection, subcutaneous injection or the like, a suppository, an agent for transdermal administration, an intravesical injection, or an agent for transmucosal administration. Particularly, when it comes to the peptide digested in the stomach, parenteral administration by intravenous injection or the like is preferable.

In a solid composition for oral administration, one or more active substances can be mixed with at least one inactive diluent such as lactic acid, mannitol, glucose, microcrystalline cellulose, hydroxypropyl cellulose, starch, polyvinyl pyrrolidone, or magnesium aluminuometasilicate. According to the common method, the composition can contain additives other than the inactive diluent, such as a lubricant, a disintegrant, a stabilizer, a solubilizer, and a solublizing agent. The tablet or pill can be coated as necessary with sugar or with a film of a gastric or enteric substance.

A liquid composition for oral administration can contain, for example, an opalizer, a solution, a suspension, a syrup, or an elixir and can contain a generally used inactive diluent such as purified water or ethanol. The composition can contain additives other than the inactive diluent, such as a moisturizer, a suspension, a sweetener, an aromatic, and a preservative.

The injection for parenteral administration can contain an aqueous or non-aqueous sterile solution, a suspension, or an opalizer. The water-soluble solution or suspension can contain, for example, distilled water for injection or physiological saline, as a diluent. Examples of the diluent of the water-insoluble solution or suspension include propylene glycol, polyethylene glycol, plant oil (for example, olive oil), alcohols (for example, ethanol), Polysorbate 80, and the like. The composition can further contain a moisturizer, an emulsifier, a dispersant, a stabilizer, a solubilizer, a solubilizing agent, a preservative, and the like. The composition can be sterilized by being filtered through a bacteria retentive filter, mixed with a germicide, or irradiated with light. Moreover, after being prepared, the sterilized solid composition can be used by being dissolved in sterile water or other vehicles for sterile injection upon use.

The dosage can be appropriately determined in consideration of the potency of activity of the substance obtained by the method for screening the active ingredient, that is, the active ingredient of the pharmaceutical composition, the symptom, the age or sex of a subject of administration, and the like. Preferably, the dosage can be calculated according to the route of administration, such that the concentration of the drug in blood around a tumor or the concentration of the drug in a tumor becomes 3 to 30 times the concentration, for example, 10 times the concentration inhibiting the activity or expression of the polypeptide of the present invention by 50%. For example, in the case of oral administration, a daily dose thereof for an adult (with a body weight of 60 kg) is generally about 0.1 mg to 100 mg and preferably 0.1 mg to 50 mg. In the case of parenteral administration, a daily dose thereof in the form of an injection is 0.01 mg to 50 mg and preferably 0.01 mg to 10 mg.

A subject to be treated with the pharmaceutical composition of the present invention is a test subject whose specimen is detected to have the polynucleotide of the present invention and/or the polypeptide of the present invention (that is, a patient with cancer which is positive for either the polynucleotide of the present invention or the polypeptide of the present invention). The substance inhibiting the polypeptide of the present invention kills the cells which acquired the tumorigenic potential by the polynucleotide of the present invention. Accordingly, the substance of inhibiting the polypeptide of the present invention is an agent effective for treating cancer (particularly, lung cancer or bladder cancer) which is positive for either the polynucleotide of the present invention or the polypeptide of the present invention.

Preparation processes of Compound A, Compound B, Compound C, Compound D, and Compound E is shown below. In the following sentences, "ESI+" represents a value of m/z in mass spectrometry (ESI of ionization method, (M+H)$^+$), "APCI/ESI+" represents a value of m/z in mass spectrometry (simultaneous measurement of APCI and ESI of ionization method, (M+H)$^+$), "NMR1" represents δ (ppm) in $^1$H-NMR in dimethyl sulfoxide-d$_6$, and "NMR2" represents δ (ppm) in $^1$H-NMR in CDCl$_3$.

Preparation Example 1 Preparation of Compound A (1) A mixture of methyl 3,5-dimethoxybenzoate (1 g) and acetonitrile (20 mL) was ice-cooled, and N-fluoro-N'-(chloromethyl)triethylenediamine bis(tetrafluoroborate) (4.09 g) was added thereto, followed by stirring at room temperature overnight. To the reaction mixture, a saturated aqueous sodium bicarbonate solution was added, followed by extraction with ethyl acetate. The organic layer was washed with saturated brine, and anhydrous sodium sulfate and basic silica gel were added thereto, followed by stirring for 30 minutes and then filtering. The filtrate was concentrated under reduced pressure and the residue was purified by silica gel column chromatography (ethyl acetate/hexane), to obtain methyl 2,6-difluoro-3,5-dimethoxybenzoate (292 mg).

ESI+: 233

(2) A mixture of methyl 2,6-difluoro-3,5-dimethoxybenzoate (10 g) and tetrahydrofuran (50 mL) was ice-cooled, and lithium borohydride (3.0 M tetrahydrofuran solution, 43 mL) was added thereto, followed by stirring at room temperature for 65 hours. The reaction mixture was ice-cooled again, and additional lithium borohydride (3.0 M tetrahydrofuran solution, 14 mL) was added thereto, followed by stirring at room temperature for 22 hours. The reaction mixture was ice-cooled and slowly added into ice water (300 mL). Further, concentrated hydrochloric acid (25 mL) was slowly added thereto, followed by stirring at room temperature for 1 hour and extracting with toluene/ethyl acetate (1:1). The organic layer was washed with a saturated aqueous sodium bicarbonate solution and saturated brine, dried over anhydrous sodium sulfate, and then filtered. The filtrate was concentrated under reduced pressure to obtain (2,6-difluoro-3,5-dimethoxyphenyl)methanol (8.67 g).

ESI+: 205

(3) A mixture of (2,6-difluoro-3,5-dimethoxyphenyl) methanol (1.71 g), triethylamine (2.57 mL), and tetrahydrofuran (34 mL) was ice-cooled, and methanesulfonyl chloride (716 µL) was added thereto, followed by stirring for 1 hour. To the reaction mixture was added water, followed by extraction with ethyl acetate. The organic layer was washed with saturated brine, dried over anhydrous sodium sulfate, and then filtered. The filtrate was concentrated under reduced pressure to obtain 2,6-difluoro-3,5-dimethoxybenzyl methanesulfonate (2.32 g).

NMR2: 3.04 (3H, s), 3.88 (6H, s), 5.34 (2H, s), 6.72 (1H, t, J=8.2 Hz)

(4) To a mixture of 2-chloro-5-hydroxypyrimidine (4.38 g), potassium carbonate (9.27 g), and N,N-dimethylformamide (79 mL), 2,6-difluoro-3,5-dimethoxybenzyl methanesulfonate (7.89 g) was added, followed by stirring at 60° C. for 1 hour. To the reaction mixture was added water. The generated solid was collected by filtration, washed with water, and then dried under reduced pressure to obtain 2-chloro-5-[(2,6-difluoro-3,5-dimethoxybenzyl)oxy]pyrimidine (8.53 g).

APCI/ESI+: 317

(5) Under an argon atmosphere, to a mixture of 2-chloro-5-[(2,6-difluoro-3,5-dimethoxybenzyl)oxy]pyrimidine (1.03 g), 3-methoxy-4-[4-(4-methylpiperazin-1-yl)piperidin-1-yl] aniline (1.29 g), 1,1'-binaphthalene-2,2'-diyl bis(diphenylphosphine) (609 mg), cesium carbonate (3.19 g), and dioxane (20.6 mL) was added palladium acetate (146 mg) at room temperature, followed by stirring at 100° C. for 4 hours. To the reaction mixture was added water, followed by extraction with ethyl acetate. The organic layer was washed with saturated brine, dried over anhydrous magnesium sulfate, and then filtered. The filtrated was concentrated under reduced pressure, and the residue was washed by silica gel column chromatography (chloroform/methanol/concentrated aqueous ammonia), purified by basic silica gel column chromatography (ethyl acetate), and then recrystallized with ethyl acetate and then with ethanol to obtain 5-[(2,6-difluoro-3,5-dimethoxybenzyl)oxy]-N-{3-methoxy-4-[4-(4-methylpiperazin-1-yl)piperidin-1-yl]phenyl}pyrimidin-2-amine (Compound A: 830 mg).

ESI+: 585

NMR1: 1.45-1.60 (2H, m), 1.73-1.84 (2H, m), 2.14 (3H, s), 2.17-2.58 (11H, m), 3.24-3.36 (2H, m), 3.75 (3H, s), 3.87 (6H, s), 5.16 (2H, s), 6.79 (1H, d, J=8.8 Hz), 7.07 (1H, t, J=8.4 Hz), 7.24 (1H, dd, J=8.8, 2.4 Hz), 7.32 (1H, d, J=2.4 Hz), 8.29 (2H, s), 9.21 (1H, s)

Preparation Example 2 Preparation of Compound B (1) Under an argon atmosphere, to a mixture of 2-chloro-5-[(2,6-difluoro-3,5-dimethoxybenzyl)oxy]pyrimidine (800 mg) prepared by the same method as in Preparation Example 1(4), 2-(4-amino-1H-pyrazol-1-yl)ethanol (642 mg), 1,1'-binaphthalene-2,2'-diyl bis(diphenylphosphine) (472 mg), cesium carbonate (2.47 g), and dioxane (16 mL) was added palladium acetate (113 mg) at room temperature, followed by stirring at 100° C. for 6 hours. To the reaction mixture were added water and chloroform, the insoluble materials were separated by filtration with celite, and the filtrate was then extracted with chloroform. The organic layer was washed with saturated brine, dried over anhydrous magnesium sulfate, and filtered. The filtrate was concentrated under reduced pressure and the residue was purified by silica gel column chromatography (chloroform/methanol) to obtain 2-[4-({5-[(2,6-difluoro-3,5-dimethoxybenzyl)oxy] pyrimidin-2-yl}amino)-1H-pyrazol-1-yl]ethanol (Compound B: 139 mg).

ESI+:408

NMR1: 3.69 (2H, dd, J=11.0, 5.6 Hz), 3.87 (6H, s), 4.07 (2H, t, J=5.6 Hz), 4.83 (1H, t, J=5.4 Hz), 5.14 (2H, s), 7.07 (1H, t, J=8.4 Hz), 7.45 (1H, d, J=0.6 Hz), 7.88 (1H, d, J=0.6 Hz), 8.26 (2H, s), 9.20 (1H, s)

Preparation Example 3 Preparation of Compound C (1) Under an argon atmosphere, to a mixture of 2-chloro-5-[(2,6-dichloro-3,5-dimethoxybenzyl)oxy]pyrimidine (1.33 g) prepared by the same method as in Preparation Example 1(4), 1-(tetrahydro-2H-pyran-2-yl)-1H-pyrazole-4-amine (913 mg), 1,1'-binaphtalene-2,2'-diyl bis(diphenylphosphine) (785 mg), cesium carbonate (4.11 g), and dioxane (26.6 mL) was added palladium acetate (189 mg) at room temperature, followed by stirring at 100° C. for 4 hours. To the reaction mixture was added water, followed by extraction with ethyl acetate. The organic layer was washed with saturated brine, dried over anhydrous sodium sulfate, and then filtered. The filtrate was concentrated under reduced pressure and the residue was purified by silica gel column chromatography (ethyl acetate/hexane) to obtain 5-[(2,6-difluoro-3,5-dimethoxybenzyl)oxy]-N-[1-(tetrahydro-2H-pyran-2-yl)-1H-pyrazol-4-yl]pyrimidin-2-amine (1.73 g).

APCI/ESI+: 448

(2) To a mixture of 5-[(2,6-difluoro-3,5-dimethoxybenzyl)oxy]-N-[1-(tetrahydro-2H-pyran-2-yl)-1H-pyrazol-4-yl]pyrimidin-2-amine (3.59 g) and methanol (20 mL) was added 4 M hydrogen chloride/dioxane solution (40 mL), followed by stirring at room temperature for 6 hours. The reaction mixture was concentrated under reduced pressure and then to the residue was added a saturated aqueous sodium bicarbonate solution. The generated solids were collected by filtration, washed with diethyl ether, and dried under reduced pressure to obtain 5-[(2,6-difluoro-3,5-dimethoxybenzyl)oxy]-N-(1H-pyrazol-4-yl)pyrimidin-2-amine (2.9 g).

APCI/ESI+: 364

(3) To a mixture of 5-[(2,6-difluoro-3,5-dimethoxybenzyl)oxy]-N-(1H-pyrazol-4-yl)pyrimidin-2-amine (50 mg), potassium carbonate (57 mg), and N,N-dimethylformamide (1 mL) was added [(4S)-2,2-dimethyl-1,3-dioxolan-4-yl] methyl 4-methylbenzenesulfonate (118 mg), followed by stirring at 60° C. for 1 hour and at 110° C. for 4 days. To the reaction mixture was added water, followed by extraction with ethyl acetate. The organic layer was washed with saturated brine, dried over anhydrous magnesium sulfate, and then filtered. The filtrate was concentrated under reduced pressure and the obtained residue was then purified by silica gel column chromatography (ethyl acetate/hexane) to obtain 5-[(2,6-difluoro-3,5-dimethoxybenzyl)oxy]-N-(1-{[(4R)-2,2-dimethyl-1,3-dioxolan-4-yl]methyl}-1H-pyrazol-4-yl)pyrimidin-2-amine (39 mg).

APCI/ESI+: 478

(4) To a mixture of 5-[(2,6-difluoro-3,5-dimethoxybenzyl)oxy]-N-(1-{[(4R)-2,2-dimethyl-1,3-dioxolan-4-yl]methyl}-1H-pyrazol-4-yl)pyrimidin-2-amine (45 mg) and tetrahydrofuran (2 mL) was added 1 M hydrochloric acid (1 mL), followed by stirring at 50° C. for 3 hours. To the reaction mixture was added saturated aqueous sodium bicarbonate solution, followed by extraction with chloroform. The organic layer was washed with saturated brine, dried over anhydrous sodium sulfate, and then filtered. The filtrate was concentrated under reduced pressure and the residue was purified by silica gel column chromatography (chloroform/methanol) and then solidified with ethyl acetate to obtain (2R)-3-[4-({5-[2,6-difluoro-3,5-dimethoxybenzyl) oxy]pyrimidin-2-yl}amino)-1H-pyrazol-1-yl]propane-1,2-diol (Compound C: 25 mg).

ESI+: 438

NMR1: 3.23-3.38 (2H, m), 3.72-3.80 (1H, m), 3.84-3.96 (7H, m), 4.15 (1H, dd, J=13.8, 4.1 Hz), 4.67 (1H, t, J=5.6 Hz), 4.91 (1H, d, J=5.3 Hz), 5.14 (2H, s), 7.06 (1H, t, J=8.4 Hz), 7.45 (1H, d, J=0.6 Hz), 7.87 (1H, d, J=0.6 Hz), 8.26 (2H, s), 9.21 (1H, s)

Preparation Example 4 Preparation of Compound D (1) In the same manner as in Preparation Example 1(5), using 4-(4-methylpiperazin-1-yl)aniline and 2-chloro-5-[(2,6-difluoro-3,5-dimethoxybenzyl)oxy]pyrimidine prepared by the same method as in Preparation Example 1(4) as starting materials, 5-[(2,6-difluoro-3,5-dimethoxybenzyl) oxy]-N-[4-(4-methylpiperazin-1-yl)phenyl]pyrimidin-2-amine (Compound D) was obtained.

ESI+: 472

NMR1: 2.21 (3H, s), 2.41-2.48 (4H, m), 2.98-3.08 (4H, m), 3.87 (6H, s), 5.15 (2H, s), 6.81-6.90 (2H, m), 7.07 (1H, t, J=8.4 Hz), 7.47-7.55 (2H, m), 8.26 (2H, s), 9.15 (1H, s)

Preparation Example 5 Preparation of Compound E (1) To a mixture of (1-methyl-3-nitro-1H-pyrazol-5-yl) methanol (398 mg), 3,4-dihydro-2H-pyran (459 μL), and ethyl acetate (8 mL) was added p-toluenesulfonic acid monohydrate (96 mg) followed by stirring at room temperature for 1.5 hours. Further, 3,4-dihydro-2H-pyran (459 μL) and p-toluenesulfonic acid monohydrate (96 mg) were added thereto, followed by stirring at room temperature for 1.5 hours. To the reaction mixture was added water, followed by extraction with ethyl acetate. The organic layer was washed with saturated brine, dried over anhydrous sodium sulfate, and then filtered. The filtrate was concentrated under reduced pressure and the residue was purified by silica gel column chromatography (hexane/ethyl acetate) to obtain 1-methyl-3-nitro-5-[(tetrahydro-2H-pyran-2-yloxy)methyl]-1H-pyrazol (487 mg).

APCI/ESI+: 242

(2) Under an argon atmosphere, to a mixture of 1-methyl-3-nitro-5-[(tetrahydro-2H-pyran-2-yloxy)methyl]-1H-pyrazol (487 mg), tetrahydrofuran (4.9 mL), and ethanol (4.9 mL) was added 10% palladium-carbon (50 mg). Under a hydrogen atmosphere, the mixture was stirred for 12 hours and the insoluble materials were then removed by celite filtration. The filtrate was concentrated under reduced pressure to obtain 1-methyl-5-[(tetrahydro-2H-pyran-2-yloxy) methyl]-1H-pyrazole-3-amine (426 mg).

APCI/ESI+: 212

(3) In the same manner as in Preparation Example 3(1), using 1-methyl-5-[(tetrahydro-2H-pyran-2-yloxy)methyl]-1H-pyrazole-3-amine and 2-chloro-5-[(2,6-dichloro-3,5-dimethoxybenzyl)oxy]pyrimidine prepared by the same method as in Preparation Example 1(4) as starting materials, 5-[(2,6-difluoro-3,5-dimethoxybenzyl)oxy]-N-{1-methyl-5-[(tetrahydro-2H-pyran-2-yloxy)methyl]-1H-pyrazol-3-yl}pyrimidin-2-amine was obtained.

APCI/ESI+: 492

(4) To a mixture of 5-[(2,6-difluoro-3,5-dimethoxybenzyl)oxy]-N-{1-methyl-5-[(tetrahydro-2H-pyran-2-yloxy) methyl]-1H-pyrazol-3-yl}pyrimidin-2-amine (706 mg) and methanol (8 mL) was added 4 M hydrogen chloride/dioxane solution (8 mL), followed by stirring at room temperature for 3 hours. The reaction mixture was concentrated under reduced pressure and then to the residue was added saturated aqueous sodium bicarbonate, followed by extraction with chloroform. The organic layer was dried over anhydrous sodium sulfate and then filtered. The residue was purified by silica gel column chromatography (ethyl acetate/hexane) to obtain [3-({5-[(2,6-difluoro-3,5-dimethoxybenzyl)oxy]pyrimidin-2-yl}amino)-1-methyl-1H-pyrazol-5-yl]methanol (444 mg).

ESI+: 408

(5) A mixture of [3-({5-[(2,6-difluoro-3,5-dimethoxybenzyl)oxy]pyrimidin-2-yl}amino)-1-methyl-1H-pyrazol-5-yl] methanol (350 mg), triethylamine (359 μL), dichloromethane (7 mL), and tetrahydrofuran (7 mL) was ice-cooled, and methanesulfonyl chloride (120 μL) was added thereto, followed by stirring at room temperature for 3 hours. To the reaction mixture were added water and ethyl acetate, and the generated solid was collected by filtration and then dried under reduced pressure to obtain [3-({5-[(2,6-difluoro-3,5-dimethoxybenzyl)oxy]pyrimidin-2-yl}amino)-1-methyl-1H-pyrazol-5-yl]methyl methanesulfonate (218 mg).

NMR2: 2.96 (3H, s), 3.85 (3H, s), 3.89 (6H, s), 5.16 (2H, s), 5.25 (2H, s), 6.68 (1H, t, J=8.0 Hz), 6.91 (1H, s), 7.63 (1H, brs), 8.24 (2H, s)

(6) To a mixture of [3-({5-[(2,6-difluoro-3,5-dimethoxybenzyl)oxy]pyrimidin-2-yl}amino)-1-methyl-1H-pyrazol-5-yl]methylmethanesulfonate (795 mg) and N-methylpyrrolidone (15.9 mL) was added 1-Methylpiperazine (901 µL), followed by stirring at 80° C. for 2 hours. To the reaction mixture were added water and saturated aqueous sodium bicarbonate, the generated solids were collected by filtration, and then the filtrate was extracted with chloroform. The organic layer was washed with saturated brine, dried over anhydrous sodium sulfate, and then filtered. The filtrate was concentrated under reduced pressure. Then, the residue and the solid previously collected by filtration were purified by silica gel column chromatography (chloroform/methanol) and then basic silica gel column chromatography (ethyl acetate/methanol), and then solidified with ethanol/diisopropyl ether to obtain 5-[(2,6-difluoro-3,5-dimethoxybenzyl) oxy]-N-{1-methyl-5-[(4-methylpiperazin-1-yl)methyl]-1H-pyrazol-3-yl}pyrimidin-2-amine (Compound E: 168 mg).

ESI+: 490

NMR1: 2.14 (3H, s), 2.18-2.53 (8H, m), 3.45 (2H, s), 3.67 (3H, s), 3.87 (6H, s), 5.15 (2H, s), 6.46 (1H, s), 7.06 (1H, t, J=8.4 Hz), 8.26 (2H, s), 9.42 (1H, s)

<Method for Screening Active Ingredient of Pharmaceutical Composition>

A method for screening the active ingredient of the pharmaceutical composition includes [1] a method for screening a substance inhibiting the polypeptide of the present invention and [2] a method for screening an agent for treating cancer (particularly, lung cancer or bladder cancer) which is positive for either the polynucleotide of the present invention or the polypeptide of the present invention.

[1] Method for Screening Substance Inhibiting Polypeptide of the Present Invention (Inhibiting Activity and/or Expression of Polypeptide of the Present Invention)

The method for screening a substance inhibiting the polypeptide of the present invention is not particularly limited as long as the method comprises the following steps (i) to (iii):

(i) bringing a test substance into contact with either the polypeptide of the present invention or cells expressing the polypeptide of the present invention;

(ii) analyzing whether the polypeptide is inhibited; and (iii) selecting a substance inhibiting the polypeptide The screening method includes the following methods.

(a) In Vitro-Type Screening Method;

A method for screening a substance inhibiting the activity of the polypeptide of the present invention, comprising (1) bringing a test substance into contact with the polypeptide of the present invention, (2) analyzing whether the activity of the polypeptide is inhibited, and (3) selecting a substance inhibiting the activity of the polypeptide.

(b) Cell-Type Screening Method

A method for screening a substance inhibiting the activity of the polypeptide of the present invention, comprising (1) bringing a test substance into contact with cells expressing the polypeptide of the present invention, (2) analyzing whether the activity of the polypeptide is inhibited, and (3) selecting a substance inhibiting activity of the polypeptide.

(c) Expression Inhibition-Type Screening Method

A method for screening a substance inhibiting the expression of the polypeptide of the present invention, comprising (1) bringing a test substance into contact with cells expressing the polypeptide of the present invention, (2) analyzing whether the expression of the polypeptide is inhibited, and (3) selecting a substance inhibiting the expression of the polypeptide.

Each of the screening methods will be described below. The cells expressing the polypeptide of the present invention includes cells which intrinsically expresses the polypeptide of the present invention and cells which express the polypeptide of the present invention as a result of gene transfer of the cells with a vector containing the polynucleotide of the present invention. For the cells expressing the polypeptide of the present invention, it is preferable to use cells which express the polypeptide of the present invention as a result of gene transfer of the cells with a vector containing the polynucleotide of the present invention.

(a) In Vitro-Type Screening Method

The in vitro-type screening method includes steps in which a test substance is added to and brought into contact with the purified polypeptide of the present invention (contact step); whether the activity of the polypeptide of the present invention has been inhibited by the test substance is analyzed by comparing the activity with the activity of the polypeptide of the present invention which has not been brought into contact with the test substance (analysis step); and a substance inhibiting the activity of the polypeptide of the present invention (that is, agent for treating cancer (preferably, lung cancer or bladder cancer) which is positive for either the polynucleotide of the present invention or the polypeptide of the present invention) is selected.

In the method for screening an active composition of the pharmaceutical composition, in particular, for example, each step is performed as below. After a test substance is added to and brought into contact with the purified polypeptide of the present invention, ATP is added thereto, and the activity of the polypeptide is measured. As a control, the purified polypeptide is mixed with and brought into contact with a vehicle (for example, DMSO) of the test substance, ATP is then added thereto, and the activity of the polypeptide is measured. As a background control, a condition in which addition of ATP is not performed can be set. Thereafter, whether the activity of the polypeptide of the present invention has been inhibited by the test substance is analyzed. Whether the activity (that is, auto-phosphorylation activity) of the polypeptide of the present invention has been inhibited by the test substance can be decided by analyzing the change in the level of tyrosine phosphorylation of the polypeptide of the present invention which is caused by the test substance. That is, if the activity (that is, auto-phosphorylation activity) of the polypeptide of the present invention is further inhibited when the test substance is added to (brought into contact with) the polypeptide, compared to a case in which the vehicle control is added to (brought into contact with) the polypeptide, the test substance is selected as a substance inhibiting the activity of the polypeptide of the present invention (that is, an agent for treating cancer (preferably, lung cancer or bladder cancer) which is positive for either the polynucleotide of the present invention or the polypeptide of the present invention). The in vitro-type screening method of the present invention also includes a screening method which is performed in the same manner as above, except that in the above step, a peptide substrate is added to and mixed with the test substance before the addition of ATP, and the phosphorylation activity with respect to the peptide substrate is analyzed as the activity of the polypeptide of the present invention (that is, whether the activity of the polypeptide of the present invention has been inhibited by the test substance is decided by analyzing the change in the level of phosphorylation of the peptide substrate caused by the polypeptide of the present invention). By using the above method, a substance which inhibits the activity by 50% or a higher rate at a concentration of up to 10 µM, preferably up to 1 µM, and more preferably up to 0.1 µM is selected as a substance inhibiting the activity of the polypeptide of the present invention. For example, the method of Example 21 can be used as the in vitro-type screening method of the present invention.

(b) Cell-Type Screening Method

The cell-type screening method includes a method in which cells expressing the polypeptide of the present invention are mixed with (added to) and brought into contact with a test substance (contact step); whether the activity of the polypeptide of the present invention has been inhibited by the test substance is analyzed by comparing the activity with the activity of the polypeptide of the present invention which has not been brought into contact with the test substance (analysis step); and a substance inhibiting the activity of the polypeptide of the present invention (that is, an agent for treating cancer (preferably, lung cancer or bladder cancer) which is positive for either the polynucleotide of the present invention or the polypeptide of the present invention) is selected. In particular, for example, the method can be performed as below.

First, cells expressing the polypeptide of the present invention are brought into contact with each of the test substance and the vehicle control (for example, DMSO). After the cells are cultured for a certain period of time, immunoblotting is performed by a publicly known SDS electrophoresis method by using a cell lysate prepared by lysing the cultured cells and an anti-phosphorylated FGFR3 antibody (for example, Cell Signaling Technology, Inc.) so as to measure the activity (that is, auto-phosphorylation activity) of the polypeptide of the present invention. In this way, whether the activity (that is, auto-phosphorylation activity) of the polypeptide of the present invention has been inhibited by the test substance is analyzed. Whether the activity of the polypeptide of the present invention has been inhibited by the test substance can be decided by analyzing the change in the level of tyrosine phosphorylation of the polypeptide of the present invention caused by the test substance. That is, if the activity of the polypeptide of the present invention has been further inhibited when the test substance is added to (brought into contact with) the polypeptide compared to a case in which the vehicle control is added to (brought into contact with) the polypeptide, the test substance is selected as a substance inhibiting the activity of the polypeptide of the present invention (that is, an agent for treating cancer (preferably, lung cancer or bladder cancer) which is positive for either the polynucleotide of the present invention or the polypeptide of the present invention).

(c) Expression Inhibition-Type Screening Method

The expression inhibition-type screening method includes a method in which cells expressing the polypeptide of the present invention is mixed with (added to) and brought into contact with a test substance (contact step); whether the expression of the polypeptide of the present invention has been inhibited by the test substance is analyzed by comparing the expression level with that observed when the cells are not brought into contact with the test substance (analysis step); and a substance inhibiting the expression of the polypeptide of the present invention (that is, an agent for treating cancer (preferably, lung cancer or bladder cancer) which is positive for either the polynucleotide of the present invention or the polypeptide of the present invention) is selected. In particular, for example, the method can be performed as below.

Certain cells expressing the polypeptide of the present invention are brought into contact with each of the test substance and the vehicle control (for example, DMSO). After culturing, an extract of the cells is prepared, and then by using the extract, whether the expression of the polypeptide of the present invention has been inhibited by the test substance is analyzed. Whether the expression of the polypeptide of the present invention has been inhibited can be analyzed by confirming whether the expression of mRNA or protein of the polypeptide of the present invention has been inhibited. More specifically, the amount of mRNA or protein of the polypeptide of the present invention existing in the cell extract is quantified by a publicly known expression level analysis method such as Northern blotting, quantitative PCR, immunoblotting, or ELISA. Whether the expression of the polypeptide of the present invention has been inhibited by the test substance can be decided by analyzing the change in the expression level of the polypeptide of the present invention caused by the test substance. That is, if the expression level (amount of mRNA or protein) of the polypeptide of the present invention is further reduced when the polypeptide is brought into contact with the test substance compared to a case in which the polypeptide is brought into contact with the vehicle control, the test substance is selected as a substance inhibiting the expression of the polypeptide of the present invention (that is, an agent for treating cancer (preferably, lung cancer or bladder cancer) which is positive for either the polynucleotide of the present invention or the polypeptide of the present invention).

[2] Method for Screening Agent for Treating Cancer which is Positive for Either Polynucleotide of the Present Invention or Polypeptide of the Present Invention The method for screening a substance inhibiting the polypeptide of the present invention (inhibiting the activity and/or the expression of the polypeptide of the present invention) can be used as a method for screening an agent for treating cancer (preferably, lung cancer or bladder cancer) which is positive for either the polynucleotide of the present invention or the polypeptide of the present invention. That is, the method for screening an agent for treating cancer which is positive for either the polynucleotide of the present invention or the polypeptide of the present invention comprises the steps i), ii), and iii) of the aforementioned [1] Method for screening substance inhibiting polypeptide of the present invention.

The method for screening an agent for treating cancer which is positive for either the polynucleotide of the present invention or the polypeptide of the present invention preferably further comprises confirming a step that the selected test substance exhibits therapeutic activity with respect to cancer (particularly, lung cancer or bladder cancer) which is positive for either the polynucleotide of the present invention or the polypeptide of the present invention, after the step of selecting a substance inhibiting the polypeptide of the present invention by analyzing whether the test substance inhibits the polypeptide of the present invention.

A step of confirming a fact that the selected test substance exhibits therapeutic activity against cancer which is positive for either the polynucleotide of the present invention or the polypeptide of the present invention.

As the step of confirming a fact that the select test substance exhibits therapeutic activity against cancer (particularly, lung cancer or bladder cancer) which is positive for either the polynucleotide of the present invention or the polypeptide of the present invention, a step of performing a publicly known evaluation method or a method established by modifying the evaluation method, for example, a step of performing an analysis method implemented by treating cultured cells or an animal tumor model expressing the polypeptide of the present invention with the selected substance is exemplified ("Clinical Oncology, $2^{nd}$ edition", Japanese Journal of Cancer and Chemotherapy).

As the suitable steps of confirming a fact that the selected substance exhibits therapeutic activity with respect to cancer (particularly, lung cancer or bladder cancer) which is positive for either the polynucleotide of the present invention or the polypeptide of the present invention, (1) a step of confirming a fact that the selected test substance exhibits the activity to inhibit cell proliferation and/or to induce cell death by using a human cancer (particularly, lung cancer or bladder cancer)-derived cancer cells intrinsically expressing the polypeptide of the present invention, (2) a step of confirming a fact that the selected test substance exhibits inhibitory activity against anchorage-independent growth of transformed cells caused to express the polypeptide of the present invention, and/or (3) a step of confirming a fact that the selected test substance exhibits inhibitory activity against the proliferation of tumors formed by inoculating the cells expressing the polynucleotide of the present invention into a nude mouse.

In the method of using the nude mouse, it is possible to use a tumor-bearing animal model which is obtained by inoculating cancer cells intrinsically expressing the polypeptide of the present invention or cells transformed by being caused to express the polypeptide of the present invention into or inside the skin of the animal, into the abdominal cavity of the animal, or into each organ of the animal (for example, a nude mouse having undergone transplantation of NIH3T3 cells caused to express the polypeptide of the present invention).

The test substance used in the method for screening the active ingredient of the pharmaceutical composition is not particularly limited. Examples of the test substance include commercially available compounds (including peptides), various publicly known compounds (including peptides) registered in the chemical file, a group of compounds obtained by combinatorial chemistry technique (N. Terrett et al., Drug Discov. Today, 4 (1): 41, 1999), a conditioned medium of microorganism, natural components derived from plants or marine life, animal tissue extracts, double-stranded nucleic acids, antibodies, antibody fragments, and compounds (including peptides) obtained by chemically or biologically modifying compounds (including peptides) selected by the method for screening the active ingredient of the pharmaceutical composition.

EXAMPLES

Hereinafter, the present invention is specifically described by examples, but the present invention is not limited to the examples. Herein, unless otherwise specified, the present invention can be embodied by a publicly known method. Moreover, when a commercially available reagent, kit, and the like are used, the present invention can be embodied by the instructions of the commercially available products.

Example 1 Isolation of FGFR3-TACC3_v1

Two hundred clinical specimens of lung cancer (Asterand USA) were reverse-transcribed into cDNA with a reverse transcriptase (SuperScript III, Life Technologies Corporation) and random primers (Random Primers, Life Technologies Corporation) according to the protocol of the kit. Thereafter, 30 cycles of PCR reaction (reaction condition: 98° C. for 10 seconds, 55° C. for 15 seconds, and 68° C. for 1 minute and 30 seconds) were performed using primers of FGFR3-TACC3_RT_F represented by SEQ ID NO: 7 and FGFR3-TACC3_RT_R represented by SEQ ID NO: 8, the cDNA obtained as above as a template, and a DNA polymerase (TaKaRa Ex Taq: TAKARA BIO INC.). Next, 30 cycles of PCR reaction (reaction condition: 98° C. for 15 seconds, 55° C. for 15 seconds, and 68° C. for 1 minute) were performed using a product of the PCR reaction diluted by 10-fold as a template, primers of FGFR3-TACC3_nested_F represented by SEQ ID NO: 9 and FGFR3-TACC3_nested_R represented by SEQ ID NO: 10, and the same DNA polymerase. After the PCR reaction, electrophoresis was performed, and as a result, a PCR product consisting of about 500 base pairs (bp) was obtained only from a specimen Lg344.

Subsequently, sequencing of the PCR product was performed by a dideoxy sequencing method (BigDye Terminator v3.1 Cycle Sequencing Kit; Life Technologies Corporation). As a result, it was clearly revealed that the PCR product of about 500 bp has a sequence in which the 3'-terminal of exon 18 of the coding sequence (hereinafter, abbreviated to CDS) of an FGFR3 gene (NM_001163213.1) registered in NCBI has been fused with the 5'-terminal of exon 11 of CDS of a TACC3 gene (NM_006342.1).

An RNA specimen Lg334 derived from a lung cancer tissue of a patient with squamous cell lung carcinoma (Asterand USA) was reverse-transcribed into cDNA with a reverse transcriptase (SuperScript III, Life Technologies Corporation) and an oligo (dT) primer (Oligo (dT) 20 Primer, Life Technologies Corporation) according to the protocol of the kit.

Thereafter, 25 cycles of PCR reaction (reaction condition: 98° C. for 15 seconds, 60° C. for 15 seconds, and 68° C. for 3 minutes and 30 seconds) were performed using primers of FGFR3-TACC3_cloning_F represented by SEQ ID NO: 11 and FGFR3-TACC3_cloning_R represented by SEQ ID NO: 12, the cDNA obtained as above as a template, and a DNA polymerase (KOD-plus-Ver. 2; TOYOBO CO., LTD.). Subsequently, 25 cycles of PCR reaction (reaction condition: 98° C. for 15 seconds, 55° C. for 15 seconds, and 68° C. for 3 minutes and 30 seconds) were performed using a product of the PCR reaction diluted by 10-fold as a template, primers of FGFR3_TACC3_cloning_BamHI_F represented by SEQ ID NO: 13 and FGFR3_TACC3_cloning_EcoRI_R represented by SEQ ID NO: 14, and the same DNA polymerase. After the PCR reaction, electrophoresis was performed, thereby obtaining a PCR product of about 2.9 kbp. The PCR product was cloned into a cloning vector (TOPO XL PCR Cloning Kit; Life Technologies Corporation), and sequencing of an insert was performed by a dideoxy sequencing method (BigDye Terminator v3.1 Cycle Sequencing Kit; Life Technologies Corporation). As a result, it was clearly revealed that in the PCR product of about 2.9 kbp, there is a transcription product (FGFR3-TACC3_v1) (SEQ ID NO: 1) in which a sequence from the 5'-terminal of CDS to the 3'-terminal of exon 18 of an FGFR3 gene registered in NCBI (NM_001163213.1) has been fused with a sequence from the 5'-terminal of exon 11 of CDS to the 3'-terminal of CDS of a TACC3 gene (NM_006342.1). The polypeptide encoded by SEQ ID NO: 1 is shown in SEQ ID NO: 2.

Further, in order to express a full length of ORF of FGFR3-TACC3_v1 as a protein, the cloning vector was subjected to an enzymatic reaction for 3 hours at 37° C. by using a restriction enzyme BamHI, and the DNA fragment treated with the restriction enzyme was purified. Furthermore, an enzymatic reaction was performed for 3 hours at 37° C. by using EcoRI, thereby purifying the DNA fragment treated with the restriction enzyme. The DNA fragments comprising ORF were cloned into position between a BamHI site and an EcoRI site present in a multicloning site of an expression vector (pMXs-puro; Cosmobio Co., Ltd.), thereby establishing an expression plasmid (FGFR3-TACC3_v1/pMXs-puro).

Example 2 Isolation of FGFR3-TACC3_v2

Fifty nine clinical specimens of bladder cancer (Asterand USA) were reverse-transcribed into cDNA with a reverse transcriptase (SuperScript III, Life Technologies Corporation) and random primers (Random Primers, Life Technologies Corporation) according to the protocol of the kit.

Thereafter, 30 cycles of PCR reaction (reaction condition: 98° C. for 10 seconds, 55° C. for 15 seconds, and 68° C. for 1 minute and 30 seconds) were performed using primers of FGFR3_TACC3_RT_F represented by SEQ ID NO: 7 and FGFR3_TACC3_RT_R represented by SEQ ID NO: 8, the cDNA obtained as above as a template, and a DNA polymerase (TaKaRa Ex Taq: TAKARA BIO INC.). Next, 30 cycles of PCR reaction (reaction condition: 98° C. for 15 seconds, 55° C. for 15 seconds, and 68° C. for 1 minute) were performed using a product of the PCR reaction diluted by 10-fold as a template, primers of FGFR3-TACC3_nested_F represented by SEQ ID NO: 9 and FGFR3-TACC3_nested_R represented by SEQ ID NO: 10, and the same DNA polymerase. After the PCR reaction, electrophoresis was performed, and as a result, it was confirmed that a PCR product of about 600 bp was obtained from a specimen Bd106.

Subsequently, sequencing of the PCR product was performed by a dideoxy sequencing method (BigDye Terminator v3.1 Cycle Sequencing Kit; Life Technologies Corporation). As a result, it was clearly revealed that the PCR product of about 600 bp has a sequence in which the 3'-terminal of exon 18 of CDS of an FGFR3 gene registered in NCBI (NM_001163213.1) has been fused with the 5'-terminal of exon 10 of CDS of a TACC3 gene (NM_006342.1).

An RNA specimen Bd106 derived from a bladder cancer tissue of a patient with bladder cancer (Asterand USA) was reverse-transcribed into cDNA with a reverse transcriptase (SuperScript III, Life Technologies Corporation) and an oligo (dT) primer (Oligo (dT) 20 Primer, Life Technologies Corporation) according to the protocol of the kit.

Thereafter, 25 cycles of PCR reaction (reaction condition: 98° C. for 15 seconds, 60° C. for 15 seconds, and 68° C. for 3 minutes and 30 seconds) were performed using primers of FGFR3-TACC3_cloning_F represented by SEQ ID NO: 11 and FGFR3-TACC3_cloning_R represented by SEQ ID NO: 12, the cDNA obtained as above as a template, and a DNA polymerase (KOD-plus-Ver. 2; TOYOBO CO., LTD.). Subsequently, 25 cycles of PCR reaction (reaction condition: 98° C. for 15 seconds, 55° C. for 15 seconds, and 68° C. for 3 minutes and 30 seconds) were performed using a product of the PCR reaction diluted by 10-fold as a template, primers of FGFR3-TACC3_cloning_BamHI_F represented by SEQ ID NO: 13 and FGFR3-TACC3_cloning_EcoRI_R represented by SEQ ID NO: 14, and the same DNA polymerase. After the PCR reaction, electrophoresis was performed, and as a result, it was confirmed that a PCR product of about 3.0 kbp was obtained. The PCR product was cloned into a cloning vector (TOPO XL PCR Cloning Kit; Life Technologies Corporation), and sequencing of an insert was performed by a dideoxy sequencing method (BigDye Terminator v3.1 Cycle Sequencing Kit; Life Technologies Corporation). As a result, it was clearly revealed that in the PCR product of about 3.0 kbp, there is a transcription product (FGFR3-TACC3_v2) (SEQ ID NO: 3) in which a sequence from the 5'-terminal of CDS to the 3'-terminal of exon 18 of an FGFR3 gene registered in NCBI (NM_001163213.1) has been fused with a sequence from the 5'-terminal of exon 10 of CDS to the 3'-terminal of CDS of a TACC3 gene (NM_006342.1). The polypeptide encoded by SEQ ID NO: 3 is shown in SEQ ID NO: 4.

Further, in order to express a full length of ORF of FGFR3-TACC3_v2 as a protein, the cloning vector was subjected to an enzymatic reaction for 3 hours at 37° C. by using a restriction enzyme BamHI, and the DNA fragment treated with the restriction enzyme was purified. Furthermore, an enzymatic reaction was performed for 3 hours at 37° C. by using EcoRI, thereby purifying the DNA fragment treated with the restriction enzyme. The DNA fragments comprising ORF were cloned into position between a BamHI site and an EcoRI site present in a multicloning site of an expression vector (pMXs-puro; Cosmobio Co., Ltd.), thereby establishing an expression plasmid (FGFR3-TACC3_v2/pMXs-puro).

Example 3 Isolation of FGFR3-TACC3_v3

Fifty nine clinical specimens of bladder cancer (Asterand USA) were reverse-transcribed into cDNA with a reverse transcriptase (SuperScript III, Life Technologies Corporation) and random primers (Random Primers, Life Technologies Corporation) according to the protocol of the kit.

Thereafter, 30 cycles of PCR reaction (reaction condition: 98° C. for 10 seconds, 55° C. for 15 seconds, and 68° C. for 1 minute and 30 seconds) were performed using primers of FGFR3-TACC3_RT_F represented by SEQ ID NO: 7 and FGFR3-TACC3_RT_R represented by SEQ ID NO: 8, the cDNA obtained as above as a template, and a DNA polymerase (TaKaRa Ex Taq: TAKARA BIO INC.). Next, 30 cycles of PCR reaction (reaction condition: 98° C. for 15 seconds, 55° C. for 15 seconds, and 68° C. for 1 minute) were performed using a product of the PCR reaction diluted by 10-fold as a template, primers of FGFR3-TACC3_nested_F represented by SEQ ID NO: 9 and FGFR3-TACC3_nested_R represented by SEQ ID NO: 10, and the same DNA polymerase. After the PCR reaction, electrophoresis was performed, and as a result, it was confirmed that a PCR product of about 650 bp was obtained from a specimen Bd021.

Subsequently, sequencing of the PCR product was performed by a dideoxy sequencing method (BigDye Terminator v3.1 Cycle Sequencing Kit; Life Technologies Corporation). As a result, it was clearly revealed that the PCR product of about 650 bp has a sequence in which the middle sequence of exon 19 of CDS of an FGFR3 gene registered in NCBI (NM_001163213.1) has been fused with a portion of intron 10-11 of a TACC3 gene and with the 5'-terminal of exon 11 of CDS of the TACC3 gene (NM_006342.1).

An RNA specimen Bd021 derived from a bladder cancer tissue of a patient with bladder cancer (Asterand USA) was reverse-transcribed with a reverse transcriptase (SuperScript III, Life Technologies Corporation) and an oligo (dT) primer (Oligo (dT) 20 Primer, Life Technologies Corporation) according to the protocol of the kit.

Thereafter, 25 cycles of PCR reaction (reaction condition: 98° C. for 15 seconds, 60° C. for 15 seconds, and 68° C. for 3 minutes and 30 seconds) were performed using primers of FGFR3-TACC3_cloning_F represented by SEQ ID NO: 11 and FGFR3-TACC3_cloning_R represented by SEQ ID NO: 12, the cDNA obtained as above as a template, and a DNA polymerase (KOD-plus-Ver. 2; TOYOBO CO., LTD.). Subsequently, 25 cycles of PCR reaction (reaction condition: 98° C. for 15 seconds, 55° C. for 15 seconds, and 68° C. for 3 minutes and 30 seconds) were performed using a product of the PCR reaction diluted by 10-fold as a template, primers of FGFR3-TACC3_cloning_BamHI_F represented by SEQ ID NO: 13 and FGFR3-TACC3_cloning_EcoRI_R represented by SEQ ID NO: 14, and the same DNA polymerase. After the PCR reaction, electrophoresis was performed, and as a result, it was confirmed that a PCR product of about 3.0 kbp was obtained. The PCR product was cloned into a cloning vector (TOPO XL PCR Cloning Kit; Life Technologies Corporation), and sequencing of an insert was performed by a dideoxy sequencing method (BigDye Terminator v3.1 Cycle Sequencing Kit; Life Technologies Corporation). As a result, it was clearly revealed that in the PCR product of about 3.0 kbp, there is a transcription product (FGFR3-TACC3_v3) (SEQ ID NO: 5) in which a sequence from the 5'-terminal of CDS to the middle of exon 19 of an FGFR3 gene registered in NCBI (NM_001163213.1) has been fused with a portion of intron 10-11 of an TACC3 gene and with a sequence from the 5'-terminal of exon 11 of CDS to the 3'-terminal of CDS of a TACC3 gene (NM_006342.1). The polypeptide encoded by SEQ ID NO: 5 is shown in SEQ ID NO: 6.

Further, in order to express a full length of ORF of FGFR3-TACC3_v3 as a protein, the cloning vector was subjected to an enzymatic reaction for 3 hours at 37° C. by using a restriction enzyme BamHI, and the DNA fragment treated with the restriction enzyme was purified. Furthermore, an enzymatic reaction was performed for 3 hours at 37° C. by using EcoRI, thereby purifying the DNA fragment treated with the restriction enzyme. The DNA fragments comprising ORF were cloned into position between a BamHI site and an EcoRI site present in a multicloning site of an expression vector (pMXs-puro; Cosmobio Co., Ltd.), thereby establishing an expression plasmid (FGFR3-TACC3_v3/pMXs-puro).

Example 4 Detection of FGFR3-TACC3_v1 cDNA samples were prepared from 200 RNA specimens derived from clinical specimens of lung cancer (Asterand USA), and the gene expression level was measured by performing quantitative PCR reaction (reaction condition: 95° C. for 10 minutes followed by 45 cycles of a reaction consisting of 95° C. for 15 seconds and 59° C. for 60 seconds) with Applied Biosystems 7900HT System, by using the cDNA samples as substrates, FGFR3-TACC3 (F18T11)_qPCR_F represented by SEQ ID NO: 15 and FGFR3-TACC3(F18T11)_qPCR_R represented by SEQ ID NO: 16 as a primer set, and a quantitative PCR kit (Power SYBR Green PCR Master Mix; Life Technologies Corporation). As a result, it was confirmed that amplification occurred only in the specimen Lg344 among the lung cancer specimens. Moreover, cDNA samples were prepared from 59 RNA specimens derived from clinical specimens of bladder cancer (Asterand USA), and the quantitative PCR was performed in the same manner as above by using the cDNA as a substrate. As a result, it was confirmed that amplification occurred in several specimens.

Example 5 Detection of FGFR3-TACC3_v2 cDNA samples were prepared from 59 RNA specimens derived from clinical specimens of bladder cancer (Asterand USA), and the gene expression level was measured by performing quantitative PCR reaction (reaction condition: 95° C. for 10 minutes followed by 45 cycles of a reaction consisting of 95° C. for 15 seconds and 59° C. for 60 seconds) with Applied Biosystems 7900HT System, by using the cDNA samples as substrates, FGFR3-TACC3 (F18T10)_qPCR_F represented by SEQ ID NO: 17 and FGFR3-TACC3(F18T10)_qPCR_R represented by SEQ ID NO: 18 as a primer set, and a quantitative PCR kit (Power SYBR Green PCR Master Mix; Life Technologies Corporation). As a result, it was confirmed that amplification occurred in several specimens of bladder cancer.

Example 6 Detection of FGFR3-TACC3_v3 cDNA samples were prepared from 59 RNA specimens derived from clinical specimens of bladder cancer (Asterand USA), and the gene expression level was measured by performing quantitative PCR reaction (reaction condition: 95° C. for 10 minutes followed by 45 cycles of a reaction consisting of 95° C. for 15 seconds and 59° C. for 60 seconds) with Applied Biosystems 7900HT System, by using the cDNA samples as substrates, FGFR3-TACC3 (F19T11)_qPCR_F represented by SEQ ID NO: 19 and FGFR3-TACC3(F19T11)_qPCR_R represented by SEQ ID NO: 20 as a primer set, and a quantitative PCR kit (Power SYBR Green PCR Master Mix; Life Technologies Corporation). As a result, it was confirmed that amplification occurred in several specimens of bladder cancer.

Example 7 Preparation of Retrovirus Solution of FGFR3-TACC3_v1

By using a transfection reagent (FUGENE (registered trademark) HD, Roche, Ltd.), Platinum E-cells were transfected with 9 μg of FGFR3-TACC3_v1/pMXs-puro (Example 1). Twenty four hours after the transfection, a D-MEM medium (Dulbecco's Modified Eagle Medium; Invitrogen) containing 10% bovine serum (Nichirei Biosciences, Inc.) was replaced, and the conditioned medium generated for 24 hours was collected, thereby preparing a retrovirus solution.

Example 8 Examination on Anchorage-Independent Cell Proliferation-Accelerating Activity of FGFR3-TACC3_v1

Polybrene (Sigma-Aldrich Co, LLC.) at a concentration of 4 μg/mL was added to the virus solution prepared in Example 7 by using FGFR3-TACC3_v1/pMXs-puro, and then the mixture was added to NIH3T3 cells to infect the cells. Six hours after the addition of the virus solution, the medium was replaced with D-MEM containing 10% bovine serum (Nichirei Biosciences, Inc.), and a day after infection, the medium was replaced with D-MEM (Invitrogen) containing 10% bovine serum (Nichirei Biosciences, Inc.) and 1 μg/mL Puromycin (Sigma-Aldrich Co, LLC.). The cells were continuously cultured for 4 weeks at 37° C. in the presence of 5% $CO_2$, thereby obtaining NIH3T3 cells stably expressing FGFR3-TACC3_v1 (designated as FGFR3-TACC3_v1 expression/NIH3T3 cells).

In order to examine anchorage-independent cell proliferation-accelerating ability of FGFR3-TACC3_v1 expression/NIH3T3 cells, the FGFR3-TACC3_v1 expression/NIH3T3 cells and NIH3T3 cells infected with pMXs-puro as an empty vector (Mock/NIH3T3 cells) were respectively seeded in a 96-well spheroid plate (Sumilon Cell-Tight Spheroid 96U; SUMITOMO BAKELITE CO., LTD.) with D-MEM (Invitrogen) containing 10% bovine serum (Nichirei Biosciences, Inc.), such that a cell count in each well became $1\times10^3$. The cells were cultured at 37° C. in the presence of 5% $CO^2$, and the cell count on the first day (Day 1) and the fourth day (Day 4) after the culturing was measured using a reagent for cell count measurement (Cell-Titer-Glo™ Luminescent Cell Viability Assay; Promega Corporation) according to the method described in the manual. For the detection, a luminometer was used. It was confirmed that while the cell count of the Mock/NIH3T3 cells did not increase from Day 1 to Day 4, the cell count of the FGFR3-TACC3_v1 expression/NIH3T3 cells increased by about 3.1-fold from Day 1 to Day 4. This result clearly showed that the FGFR3-TACC3_v1 expression/NIH3T3 cells acquired the activity of anchorage-independent cell proliferation.

Example 9 Inhibitory Action of Fusion Polypeptide Inhibitor Against Anchorage-Independent Cell Proliferating Activity of FGFR3-TACC3_v1 Expression/NIH3T3 Cells The measurement of anchorage-independent cell proliferation (colony method or the like) is known to be a system for examining anticancer activity (pharmacological effect) of a compound ("Clinical Oncology, $2^{nd}$ edition", Japanese Journal of Cancer and Chemotherapy). As a method for measuring nonadherent cell proliferation which is an alternative to the colony method, there is a method of using a spheroid plate described above.

The FGFR3-TACC3_v1 expression/NIH3T3 cells were seeded in a 96-well spheroid plate (Sumilon Cell-Tight Spheroid 96U; SUMITOMO BAKELITE CO., LTD.) with D-MEM containing 10% fetal bovine serum, such that the cell count in each well became $1\times10^3$. Moreover, as a positive control, a well added only with the medium was prepared. After the cells were cultured overnight at 37° C. in the presence of 5% $CO_2$, Dovitinib, AZD4547, and BGJ398 were added thereto at a final concentration of 100 nM. As a negative control, DMSO as a vehicle of the compound was added thereto at the same concentration (0.1%) as set at the time of adding the compound. Thereafter, the cells were cultured for 4 days at 37° C. in the presence of 5% $CO_2$, and a reagent for cell count measurement (CellTiter-Glo™ Luminescent Cell Viability Assay; Promega Corporation) was added thereto. The resultant was stirred for 20 minutes, and the cell count was measured using a luminometer. The inhibition rate of the positive control and the negative control was regarded as being 100% and 0% respectively to calculate the growth inhibition rate (%) of each compound. As a result, the inhibition rate (%) of Dovitinib, AZD4547, and BGJ398 was 40%, 74%, and 92% respectively.

The above results show that the inhibitor of the FGFR3-TACC3 fusion polypeptide can inhibit proliferation of the cancer cells or tumors expressing FGFR3-TACC3_v1.

Moreover, it was found that by screening a subject expected to benefit from the efficacy of the therapy using the polypeptide inhibitor of the present invention by the detection method of the present invention, tailor-made medical practice can be provided.

Example 10 Preparation of Retrovirus Solution of FGFR3-TACC3_v2 and FGFR3-TACC3_v3

By using FGFR3-TACC3_v2/pMXs-puro and FGFR3-TACC3_v3/pMXs-puro prepared in Examples 2 and 3, each retrovirus solution was prepared according to the method of Example 7.

Example 11 Examination on Anchorage-Independent Proliferation-Accelerating Activity of FGFR3-TACC3_v2 and FGFR3-TACC3_v3

By using the virus solution prepared using the FGFR3-TACC3_v2/pMXs-puro and FGFR3-TACC3_v3/pMXs-puro in Example 10, NIH3T3 cells stably expressing FGFR3-TACC3_v2 and FGFR3-TACC3_v3 were obtained according to the method of Example 8 (the cells were designated as FGFR3-TACC3_v2 expression/NIH3T3 cells and FGFR3-TACC3_v3 expression/NIH3T3 cells respectively).

In order to examine anchorage-independent proliferation-accelerating ability of the FGFR3-TACC3_v2 expression/NIH3T3 cells and the FGFR3-TACC3_v3 expression/NIH3T3 cells, the same method as in Example 8 was used. It was confirmed that while the cell count of the Mock/NIH3T3 cells did not increase from Day 1 to Day 4, the cell count of the FGFR3-TACC3_v2 expression/NIH3T3 cells increased by about 2.8-fold from Day 1 to Day 4. Furthermore, it was confirmed that the cell count of the FGFR3-TACC3_v3 expression/NIH3T3 cells increased by about 2.3-fold from Day 1 to Day 4. The above result clearly shows that the FGFR3-TACC3_v2 expression/NIH3T3 cells and the FGFR3-TACC3_v3 expression/NIH3T3 cells acquired the activity of anchorage-independent cell proliferation.

Example 12 Inhibitory Activity of Polypeptide Inhibitor of the Present Invention Against Anchorage-Independent Cell Proliferating Activity of FGFR3-TACC3_v2 Expression/NIH3T3 Cells and FGFR3-TACC3_v3 Expression/NIH3T3 Cells In the same manner as in Example 9, inhibitory activity against the cell proliferation of the FGFR3-TACC3_v2 expression/NIH3T3 cells and the FGFR3-TACC3_v3 expression/NIH3T3 cells was evaluated. As a result, the inhibition rate (%) of Dovitinib, AZD4547, and BGJ398 against the FGFR3-TACC3_v2 expression/NIH3T3 cells was 21%, 60%, and 90% respectively. Moreover the inhibition rate (%) of Dovitinib, AZD4547, and BGJ398 against the FGFR3-TACC3_v3 expression/NIH3T3 cells was 32%, 51%, and 87% respectively.

The above results show that the FGFR3-TACC3 fusion polypeptide inhibitor can inhibit the proliferation of cancer cells or tumors expressing FGFR3-TACC3_v2 and FGFR3-TACC3_v3.

Further, it was found that by screening a subject expected to benefit from the efficacy of the therapy using the FGFR3-TACC3 fusion polypeptide inhibitor by the detection method of the present invention, a tailor-made medical practice can be provided.

Example 13 Test of Anti-Tumorigenic Activity of FGFR3-TACC3 Fusion Polypeptide Inhibitor Against FGFR3-TACC3_v1 Expression/NIH3T3 Cells, FGFR3-TACC3_v2 Expression/NIH3T3 Cells, and FGFR3-TACC3_v3 Expression/NIH3T3 Cells The FGFR3-TACC3_v1 expression/NIH3T3 cells suspended in phosphate buffered saline (PBS) were inoculated in a number of $3\times10^6$ into 4-week-old male cann. Cg-Foxn1Nu/Crlcrlj (Nu/Nu) nude mice (Charles River Laboratories, Japan) by means of subcutaneous injection performed in the back of the mice. Three days after the inoculation, AZD4547 and BGJ398 which are FGFR3-TACC3 fusion polypeptide inhibitors were started to be administered. For the test, 4 to 5 mice were assigned to each of the vehicle group and the compound group, AZD4547 and BGJ398 were suspended in a vehicle composed of 0.5% methyl cellulose (Shin-Etsu Chemical Co., Ltd.)/99.5% distilled water, and each of the compounds was orally administered at a dosage of 30 mg/kg. The administration was performed once a day for 11 days, and the body weight of mice and a tumor diameter were measured every 2 or 3 days. A tumor volume was calculated using the following formula.

[Tumor volume (mm³)]=[major axis of tumor (mm)]×[minor axis of tumor (mm)]²×0.5

The tumor volume of the vehicle group on the date of first administration of the compound and on the date of final administration of the compound was regarded as indicating 100% inhibition and 0% inhibition so as to calculate the inhibition rate of AZD4547 and BGJ398. As a result, AZD4547 and BGJ398 were confirmed to inhibit proliferation of the FGFR3-TACC3_v1 expression/NIH3T3 cells (tumors) by 51% and 90% respectively. The anti-tumorigenic activity against the FGFR3-TACC3_v2 expression/NIH3T3 cells and the FGFR3-TACC3_v3 expression/NIH3T3 cells was examined in the same manner. As a result, AZD4547 and BGJ398 were confirmed to inhibit proliferation of the FGFR3-TACC3_v2 expression/NIH3T3 cells (tumors) by 61% and 90% respectively and inhibit growth of the FGFR3-TACC3_v3 expression/NIH3T3 cells (tumors) by 73% and 88% respectively.

Example 14 Kinase Inhibitory Activity Resulting from Administration of FGFR3-TACC3 Fusion Polypeptide Inhibitor Against Tumors of FGFR3-TACC3_v1 Expression/NIH3T3 Cells, FGFR3-TACC3_v2 Expression/NIH3T3 Cells, and FGFR3-TACC3_v3 Expression/NIH3T3 Cells As described below, the kinase inhibitory activity of AZD4547 and BGJ398 was observed in the same manner as in Example 13. The FGFR3-TACC3_v1 expression/NIH3T3 cells were inoculated in a number of $3\times10^6$, and three days after the inoculation, AZD4547 and BGJ398 were started to be administered. For the test, 5 mice were assigned to each of the vehicle group and the compound group, and 4 hours after the final administration, tumors were extracted by dissection. Thereafter, by using a lysis solution (Cell Lysis Buffer; Cell Signaling Technology, Inc., Phosphatase Inhibitor Cocktail; Thermo Fisher Scientific Inc., Complete; Roche, Ltd.), protein extracts of the tumors were rapidly prepared, and the total FGFR3 level and a phosphorylated FGFR3 level of the tumors were measured using an ELISA kit (R&D Systems). ELISA was performed according to the attached procedure manual, but detection was performed in a different way in which the chemiluminescence detection is conducted using a chemiluminescent reagent (BM chemiluminescence ELISA substrate; Roche, Ltd.) and a luminometer (ARVO; PerkinElmer Inc.).

A level obtained by correcting the phosphorylated FGFR3 level by using the total FGFR3 level (phosphorylated FGFR3 level/total FGFR3 level) was taken as a phosphorylation level. The phosphorylation level of the vehicle group was regarded as being 0% inhibition, and an absolute value 0 was regarded as being 100% inhibition, thereby calculating an inhibition rate of tyrosine auto-phosphorylation in each compound group. As a result, it was confirmed that in the group of AZD4547 and the group of BGJ398, tyrosine auto-phosphorylation of FGFR3-TACC3 fusion polypeptide v1 in the tumor was reduced by 58% and 77% respectively, compared to the vehicle group.

For the FGFR3-TACC3_v2 expression/NIH3T3 cells and the FGFR3-TACC3_v3 expression/NIH3T3 cells, examination was performed in the same manner as above. As a result, it was confirmed that in the group of AZD4547 and the group of BGJ398, tyrosine auto-phosphorylation of FGFR3-TACC3_v2 in the tumor was reduced by 54% and 66% respectively, and tyrosine auto-phosphorylation of FGFR3-TACC3_v3 in the tumor was reduced by 78% and 85% respectively, compared to the vehicle group.

From these results, it was confirmed that the anti-tumorigenic activity of AZD4547 and BGJ398 in the above animal model is based on the activity inhibiting the kinase activity of the FGFR3-TACC3 fusion polypeptide in the tumor.

Example 15 Isolation of FGFR3-TACC3_v1 from RT-112 Cell Line Derived from a Patient with Bladder Cancer An RNA sample purified from RT-112 cell line derived from a patient with bladder cancer (purchased from Leibniz-institut DSMZ-Deutsche Sammlung von Mikroorganismen and Zellkulturen GmbH) was reverse-transcribed into cDNA with a reverse transcriptase (SuperScript III, Life Technologies Corporation) and an oligo (dT) primer (Oligo (dT) 20 Primer, Life Technologies Corporation) according to the protocol of the kit.

Next, 25 cycles of PCR reaction (reaction condition: 98° C. for 15 seconds, 60° C. for 15 seconds, and 68° C. for 3 minutes and 30 seconds) were performed using primers of FGFR3-TACC3_cloning_F represented by SEQ ID NO: 11 and FGFR3-TACC3_cloning_R represented by SEQ ID NO: 12, the cDNA obtained as above as a template, and a DNA polymerase (KOD-plus-Ver. 2; TOYOBO CO., LTD.). Subsequently, 25 cycles of PCR reaction (reaction condition: 98° C. for 15 seconds, 55° C. for 15 seconds, and 68° C. for 3 minutes and 30 seconds) were performed using the a product of the PCR reaction diluted by 10-fold as a template, primers of FGFR3_TACC3_cloning_BamHI_F represented by SEQ ID NO: 13 and FGFR3_TACC3_cloning_EcoRI_R represented by SEQ ID NO: 14, and the same DNA polymerase. After the PCR reaction, electrophoresis was performed, thereby obtaining a PCR product of about 2.9 kbp. The PCR product was cloned into a cloning vector (TOPO XL PCR Cloning Kit; Life Technologies Corporation), and sequencing of an insert was performed by a dideoxy sequencing method (BigDye Terminator v3.1 Cycle Sequencing Kit; Life Technologies Corporation). As a result, it was clearly revealed that the PCR product is the same as the transcription product (FGFR3-TACC3_v1) (SEQ ID NO: 1) in which a sequence from the 5'-terminal of CDS to the 3'-terminal of exon 18 of an FGFR3 gene registered in NCBI (NM_001163213.1) has been fused with a sequence from the 5'-terminal of exon 11 to the 3'-terminal of CDS of a TACC3 gene (NM_006342.1).

Example 16 Inhibitory Action of FGFR3-TACC3 Fusion Polypeptide Inhibitor Against Anchorage-Independent Proliferation Activity of RT-112 Cell Lines Derived from a Patient with Bladder Cancer The RT-112 cells were seeded into a 96-well spheroid plate (Sumilon Cell-Tight Spheroid 96U; SUMITOMO BAKELITE CO., LTD.) with an RPMI 1640 medium containing 10% fetal bovine serum, such that the cell count in each well became $2\times10^3$. Moreover, as a positive control, a well added only with the medium was prepared. After the cells were cultured overnight at 37° C. in the presence of 5% $CO_2$, Dovitinib, AZD4547, and BGJ398 were added thereto at a final concentration of 100 nM. As a negative control, DMSO as a vehicle of the compound was added thereto at the same concentration (0.1%) at the time of adding the compound. Thereafter, the cells were cultured for 5 days at 37° C. in the presence of 5% $CO_2$, and a reagent for cell count measurement (CellTiter-Glo™ Luminescent Cell Viability Assay; Promega Corporation) was added thereto. The resultant was stirred for 20 minutes, and the cell count was measured using a luminometer. The inhibition rate of the positive control and the negative control was regarded as being 100% and 0% respectively to calculate the growth inhibition rate (%) of each compound. As a result, the inhibition rate (%) of Dovitinib, AZD4547, and BGJ398 was 80%, 90%, and 90% respectively.

Example 17 Detection of FGFR3-TACC3 Fusion Polypeptide

A method for detecting an FGFR3-TACC3 fusion polypeptide in cells was established as below. FGFR3-TACC3_v1 expression/NIH3T3 cells and NIH3T3 cells as a negative control were cultured. After being washed once with PBS, the cells were lysed for 10 minutes with a lysis solution (Cell Lysis Buffer; Cell Signaling Technology, Inc., Phosphatase Inhibitor Cocktail; Thermo Fisher Scientific, Inc., Complete; Roch, Ltd.) on ice. After centrifugation, anti-FGFR3 antibodies (Sigma-Aldrich Co, LLC.) were added to the obtained lysate, and the mixture was incubated overnight at 4° C. Thereafter, protein G beads (Protein G Sepharose 4 Fast Flow; GE Healthcare) were added thereto, and immunoprecipitation was performed for 4 hours. After centrifugation, the precipitates were washed 4 times with a washing solution (having the same composition as the aforementioned lysis solution), an SDS solution was added thereto, and the mixture was boiled for 5 minutes and suspended the precipitates. After centrifugation, the supernatant was subjected to immunoblotting by using anti-TACC3 antibodies (R&D Systems). As a result, FGFR3-TACC3 fusion polypeptide v1 was detected in the immunoprecipitates of the FGFR3-TACC3_v1 expression/NIH3T3 cells, but the FGFR3-TACC3 fusion polypeptide v1 was not detected in the NIH3T3 cells. The FGFR3-TACC3_v2 expression/NIH3T3 cells and the FGFR3-TACC3_v3 expression/NIH3T3 cells were examined in the same manner. As a result, in the immunoprecipitates of the FGFR3-TACC3_v2 expression/NIH3T3 cells and the FGFR3-TACC3_v3 expression/NIH3T3 cells, the FGFR3-TACC3 fusion polypeptide v2 and the FGFR3-TACC3 fusion polypeptide v3 were detected respectively. Moreover, RT-112 cells were examined in the same manner, and as result, the FGFR3-TACC3 fusion polypeptide v1 was detected.

The above results clearly showed that by using the anti-FGFR3 antibody and the anti-TACC3 antibody in combination, the existence of the polypeptide of the present invention in cancer cells or cancer tissues expressing the FGFR3-TACC3 fusion polypeptide can be detected, and a patient positive for the polypeptide of the present invention can be screened.

Example 18 Detection of an FGFR3-TACC3 Fusion Polynucleotide (mRNA) in Formalin Fixed Paraffin Embedded (FFPE) Slices of FGFR3-TACC3_v1 Expression/NIH3T3 Cells, FGFR3-TACC3_v2 Expression/NIH3T3 Cells, and FGFR3-TACC3_v3 Expression/NIH3T3 Cells by Means of In-Situ Hybridization (ISH) Method The FGFR3-TACC3_v1 expression/NIH3T3 cells, the FGFR3-TACC3_v2 expression/NIH3T3 cells, and the FGFR3-TACC3_v3 expression/NIH3T3 cells were subcutaneously inoculated in a number of $3\times10^6$ into 4-week-old male nude mice (CAnN.Cg-Fox n1nu/CrlCrlj (nu/nu), Charles River Laboratories Japan). After 15 days, the proliferation of cell clusters was confirmed, thereby preparing tumor-bearing mice.

From the prepared tumor-bearing mice, tissues comprising proliferating cancer cells were cut out. The tissues were washed with physiological saline, fixed with 10% neutral buffered formalin (Sigma-Aldrich Co, LLC.) for 48 hours to 144 hours at room temperature, dehydrated according to the conventional method with an automatic embedding apparatus (Tissue Tek VIP, Sakura Finetek Japan Co., Ltd.), and then embedded in paraffin (Tissue Prep, FALMA Co., Ltd.). The tissue samples embedded in paraffin were cut in a thickness of 5 μm, thereby preparing FFPE slices.

The prepared FFPE slices were heated for 15 minutes at 60° C. on a heating block (MG-2200; TOKYO RIKAKIKAI CO., LTD.), and fixed with 10% formalin (Wako Pure Chemical Industries, Ltd.) for 30 minutes at room temperature. The FFPE slices were washed 3 times with PBS (Invitrogen), dried completely, and treated with xylene (Wako Pure Chemical Industries, Ltd.) for 10 minutes at room temperature. Thereafter, the FFPE slices were washed 3 times with PBS and boiled for 10 minutes at 100° C. in Pretreatment Solution (Affymetrix, Inc). Subsequently, the slices were washed twice with purified water and then once with PBS, and then treated with Protease Solution (Affymetrix, Inc.) for 20 minutes at 40° C. in an incubator (HybEZ Hybridization System; Advanced Cell Diagnostics.). Next, the slices were washed 3 times with PBS, fixed with 4% formalin (Wako Pure Chemical Industries, Ltd.) for 5 minutes at room temperature, and washed 3 times with PBS. A branched DNA probe (QuantiGene ViewRNA Probe Set Type 4; Affymetrix, Inc.) specific to nucleotide positions 2851 to 4281 in the nucleotide sequence of an FGFR3 gene (GenBank accession number: NM_000142.3), which is common to all variants of FGFR3, and a branched DNA probe (QuantiGene ViewRNA Probe Set Type 1; Affymetrix, Inc.) specific to nucleotide positions 2220 to 2838 in the nucleotide sequence of a TACC3 gene (GenBank accession number: NM_006342.1) were diluted with Probe Set Diluent QT (Affymetrix, Inc.) by 40-fold, thereby preparing a Probe Set Solution. The solution was added to the FFPE slices, and hybridized with a polynucleotide (mRNA) for 2 hours at 40° C. in an incubator. Thereafter, the FFPE slices were washed 3 times with Wash Buffer (Affymetrix, Inc.) and reacted with PreAmplifier Mix QT (Affymetrix, Inc.) for 25 minutes at 40° C. in an incubator. Moreover, the FFPE slices were washed 3 times with Wash Buffer and reacted with Amplifier Mix QT (Affymetrix, Inc.) for 15 minutes at 40° C. in an incubator. The slices were then washed 3 times with Wash Buffer and reacted with Label Probe Diluent QT (Affymetrix, Inc.), which contained Label Probe Mix (Affymetrix, Inc.) in an amount of ⅟25 in terms of the volume, for 30 minutes at 40° C. in an incubator. Thereafter, the slices were washed twice with Wash Buffer and then once with PBS, and reacted with PBS containing a fluorescence dye DAPI (Affymetrix, Inc.) for 15 minutes at room temperature. After being washed twice with PBS, the slices were encapsulated using an encapsulating agent EcoMount (Biocare Medical, LLC), and the fluorescence thereof was observed with a confocal laser microscope (LSM700; Carl Zeiss). In all of the FFPE slices of the FGFR3-TACC3_v1 expression/NIH3T3 cells, the FGFR3-TACC3_v2 expression/NIH3T3 cells, and the FGFR3-TACC3_v3 expression/NIH3T3 cells, signals of FGFR3 and signals of TACC3 were detected, and most of the signals of FGFR3 and signals of TACC3 colocalized. This result showed that in the FFPE slice containing cells forcedly caused to express the FGFR3-TACC3 fusion genes, the signals of FGFR3 and the signals of TACC3 colocalize.

Example 19 Detection of FGFR3-TACC3 Fusion Polynucleotide (mRNA) in RT-112 Cells by Means of ISH Method According to the same procedure as in Example 18, FFPE samples of RT-112 cells as a cell line derived from a patient with bladder cancer and HSC-39 cells as a cell line derived from a patient with gastric cancer were prepared, and detection of an FGFR3-TACC3 fusion polynucleotide (mRNA) by means of the ISH method was performed. The samples were treated with the method performed after the treatment using the heating block in Example 18, and fluorescence of the encapsulated samples was observed. The obtained images were analyzed using IN Cell Analyzer 2000 (GE Healthcare). As a result, in the FFPE slices of the RT-112 cells (Example 15) expressing FGFR3-TACC3_v1, a large number of colocalizing signals of FGFR3 and TACC3 were detected, but in the FFPE slices of the HSC-39 cells which had been confirmed not to express the FGFR3-TACC3 fusion polynucleotide (mRNA) by RT-PCR described in Example 23, colocalizing signals of FGFR3 and TACC3 were practically not detected. These results clearly showed that in the FFPE slices containing the cells intrinsically expressing the FGFR3-TACC3 fusion gene, the signals of FGFR3 and the signals of TACC3 colocalize, and in the cells not expressing the FGFR3-TACC3 fusion gene, the signals do not colocalize. It clearly showed that by measuring such colocalizing signals, the existence or absence of the FGFR3-TACC3 fusion gene can be determined.

Example 20 Detection of FGFR3-TACC3 Fusion Polynucleotide (mRNA) in FFPE Slice Derived from Patient with Bladder Cancer by Means of ISH Method FFPE slices of tissues derived from patients with bladder cancer which were purchased from Asterand USA were treated by the method performed after the treatment using the heating block in Example 18, and the fluorescence of the encapsulated slices was observed. The obtained images were analyzed using IN Cell Analyzer 2000 (GE Healthcare). As a result, it was clearly revealed that the number of the colocalizing signals of FGFR3 and TACC3 is markedly greater in the FFPE slices derived from tissues of patients with bladder cancer which were confirmed to express FGFR3-TACC3_v2 by the RT-PCR method described in Example 23, than in the FFPE slices derived from tissues of patients with bladder cancer which were confirmed not to express the FGFR3-TACC3 fusion polynucleotide (mRNA) by the RT-PCR method described in Example 23.

For FFPE slices derived from tissues of several patients with bladder cancer which were purchased from Tissue Solutions UK, colocalization of the signals of FGFR3 and TACC3 was examined by the same method. As a result, it was clearly revealed that the number of colocalizing signals of FGFR3 and TACC3 is markedly greater in the FFPE slices derived from tissues of patients with bladder cancer confirmed to express the FGFR3-TACC3 fusion polynucleotide (mRNA) by the RT-PCR method described in Example 23, than in the FFPE slices derived from tissues of patients with bladder cancer confirmed not to express the FGFR3-TACC3 fusion polynucleotide (mRNA) by the RT-PCR method described in Example 23.

These results clearly showed that even in the FFPE slices derived from tissues of patients with bladder cancer, by observing colocalizing signals, the existence or absence of the FGFR3-TACC3 fusion gene can be decided.

Example 21 Inhibitory Action of Compounds Against In Vitro Kinase Activity of FGFR3-TACC3 Fusion Polypeptide (1) Establishment of FLAG tag fusion expression plasmids (FGFR3-TACC3_v1 (N-FLAG)/pcDNA3.1/Zeo (+), FGFR3-TACC3_v2 (N-FLAG)/pcDNA3.1/Zeo (+), and FGFR3-TACC3_v3 (N-FLAG)/pcDNA3.1/Zeo (+))

In order to obtain an FGFR3-TACC3 fusion polynucleotide in which a FLAG tag has been fused with the 5'-terminal, PCR reaction for adding a FLAG tag to the 5'-terminal was performed using the vectors cloned in Examples 1, 2, and 3 as templates. 12 cycles of PCR reaction (reaction condition: 98° C. for 15 seconds, 55° C. for 15 seconds, and 68° C. for 3 minutes and 30 seconds) were performed using primers of FGFR3_N_FLAG BamHI represented by SEQ ID NO: 21 and FGFR3_TACC3_cloning_EcoRI_R represented by SEQ ID NO: 14 and a DNA polymerase (KOD-plus-Ver. 2; TOYOBO CO., LTD.). The PCR products were cloned into a cloning vector (TOPO XL PCR Cloning Kit; Life Technologies Corporation), and sequencing of an insert was performed by a dideoxy sequencing method (BigDye Terminator v3.1 Cycle Sequencing Kit; Life Technologies Corporation). As a result, it was confirmed that the PCR products have nucleic acid sequences in which 3 bases (ATG) encoding the first methionine have been deleted from the sequences described in SEQ ID NO: 1, SEQ ID NO: 3, and SEQ ID NO: 5, and a nucleic acid sequence (SEQ ID NO: 22) encoding start codon and the FLAG tag has been added to the 5'-terminal. The polypeptides encoded by the PCR products are designated as FGFR3-TACC3_v1 (N-FLAG) fusion polypeptide, FGFR3-TACC3_v2 (N-FLAG) fusion polypeptide, and FGFR3-TACC3_v3 (N-FLAG) fusion polypeptide respectively, and these are collectively designated as FGFR3-TACC3 (N-FLAG) fusion polypeptides. In order to establish expression vectors which express, as a protein, a full length of ORF of FGFR3-TACC3_v1 (N-FLAG), FGFR3-TACC3_v2 (N-FLAG), and FGFR3-TACC3_v3 (N-FLAG) to which the above FLAG sequence has been added, a DNA fragment treated with a restriction enzyme which was obtained by subjecting the above cloning vector to an enzymatic reaction for 3 hours at 37° C. by using a restriction enzyme BamHI was purified, and a DNA fragment treated with a restriction enzyme which was obtained by subjecting the above cloning vector to an enzymatic reaction for 3 hours at 37° C. by using EcoRI was purified. These DNA fragments comprising ORF were cloned into the position between a BamHI site and an EcoRI site present in a multicloning site of an expression vector (pcDNA3.1/Zeo (+), Life Technologies Corporation), thereby establishing expression plasmids (FGFR3-TACC3_v1 (N-FLAG)/pcDNA3.1/Zeo (+), FGFR3-TACC3_v2 (N-FLAG)/pcDNA3.1/Zeo (+), and FGFR3-TACC3_v3 (N-FLAG)/pcDNA3.1/Zeo (+)).

(2) Acquisition of FGFR3-TACC3 (N-FLAG) Fusion Polypeptide

From the day before transfection was performed, HEK293 cells were cultured in D-MEM containing 10% fetal bovine serum with total ten collagen coated dishes with 15 cm diameter in a number of $0.5 \times 10^7$ per dish. On the day of transfection, the HEK 293 cells were transfected with the FGFR3-TACC3_v1 (N-FLAG)/pcDNA3.1/Zeo (+), the FGFR3-TACC3_v2 (N-FLAG)/pcDNA3.1/Zeo (+), and the FGFR3-TACC3_v3 (N-FLAG)/pcDNA3.1/Zeo (+), by using an amount of 27 µg of each plasmid and 81 µL of a transfection reagent (FUGENE (registered trademark) HD; Roche, Ltd.) for each dish. Twenty four hours after transfection, the medium was removed, and the cells were washed 3 times with PBS. Thereafter, 1 mL of PBS was added thereto, the cells were scrapped off with a cell scraper (Corning Incorporated) and collected into a polypropylene tube. After removing supernatant by centrifugation for 5 minutes at 1,200 rpm, the cells were lysed by incubation on ice for 30 minutes with 150 µL of a cell lysis solution (50 mM Tris HCl (pH 8.0), 150 mM NaCl, 1% NP-40, 1 mM EDTA, protease inhibitor cocktail complete (Roche-Diagnostics)). Each of the FGFR3-TACC3_v1 (N-FLAG) fusion polypeptide, FGFR3-TACC3_v2 (N-FLAG) fusion polypeptide, and FGFR3-TACC3_v3 (N-FLAG) fusion polypeptide in the supernatant obtained by centrifugation of the cell lysate was purified using an M2 antibody affinity gel (ANTI-FLAG M2 Affinity Gel; Sigma-Aldrich Co, LLC.) according to the method described in the product information. For washing and elution, a washing solution (50 mM Tris HCl (pH 8.0), 150 mM NaCl, 1% NP-40, 1 mM EDTA, protease inhibitor cocktail complete (Roche-Diagnostics)) and an eluent (20 mM Tris HCl (pH 7.4), 10 mM $MgCl_2$, 10 mM $MnCl_2$, 0.5 mg/mL FLAG peptide) were used respectively, thereby obtaining 100 µL of an eluate. The eluate was subjected to immunoblotting and silver staining by using anti-FGFR3 antibodies (Cell Signaling Technology, Inc.) and anti-FLAG M2 antibodies (Sigma-Aldrich Co, LLC.), thereby confirming that the FGFR3-TACC3_v1 (N-FLAG) fusion polypeptide, the FGFR3-TACC3_v2 (N-FLAG) fusion polypeptide, and the FGFR3-TACC3 (N-FLAG) fusion polypeptide were obtained.

(3) Detection of In Vitro Kinase Activity of FGFR3-TACC3 (N-FLAG) Fusion Polypeptide The phosphorylation activity of the FGFR3-TACC3_v1 (N-FLAG) fusion polypeptide, the FGFR3-TACC3_v2 (N-FLAG) fusion polypeptide, and the FGFR3-TACC3_v3 (N-FLAG) fusion polypeptide, which were purified as above, to a peptide substrate was examined using a kinase activity detection kit (HTRF KinEASE-TK; Cisbio Bioassays). A 384-well Low-volume Black plate (Corning Incorporated) was used, and a 1-fold diluted solution, a 3-fold diluted solution, or a 10-fold diluted solution of the above eluent was used respectively in an amount of 1 µL as an enzyme source. Moreover, a reaction solution was prepared by adding DDT and $Mg^{2+}$ to 5× Kinase buffer included in the kit such that the final concentration thereof became 1 mM and 5 mM respectively. As a substrate, TK Substrate included in the kit was added to the plate such that the final concentration thereof became 2.0 µM. Furthermore, some of the wells were not supplemented with ATP while some of the wells were supplemented with ATP such that the final concentration thereof became 100 µM, and a reaction was performed for 1 hour at room temperature by controlling the final volume to be 5.0 µL. After the reaction, an Sa-XL 665 solution and a TK Antibody-Eu (K) solution were prepared according to the method that the kit suggested, and each of the solutions was added to wells in an amount of 2.5 µL each, followed by incubation for 1 hour at room temperature, and count of HTRF (that is, phosphorylation of the peptide substrate) was detected. As a result, it was clearly revealed that when 1 µL of the 1-fold diluted solution of each eluate containing the FGFR3-TACC3_v1 (N-FLAG) fusion polypeptide, the FGFR3-TACC3_v2 (N-FLAG) fusion polypeptide, or the FGFR3-TACC3_v3 (N-FLAG) fusion polypeptide was added to the wells supplemented with ATP, the count of HTRF was increased by about 38-fold, 40-fold, and 38-fold respectively, compared to the wells not supplemented with ATP; when the 1 µL of the 3-fold diluted solution of the eluate was added to the wells supplemented with ATP, the count of HTRF was increased by about 27-fold, 34-fold, and 31-fold respectively; and when 1 µL of the 10-fold diluted solution of the eluate was added to the wells supplemented with ATP, the count of HTRF was increased by 5-fold, 18-fold, and 11-fold respectively.

As described above, the use of a kinase activity detection kit made it possible to detect in vitro kinase activity of the FGFR3-TACC3 (N-FLAG) fusion polypeptide.

(4) Inhibitory Activity of Compound Against In Vitro Kinase Activity of FGFR3-TACC3 (N-FLAG) Fusion Polypeptide The inhibitory activity of compounds Dovitinib, AZD4547, BGJ398, and LY2874455 against in vitro kinase activity of the FGFR3-TACC3_v1 (N-FLAG) fusion polypeptide, the FGFR3-TACC3_v2 (N-FLAG) fusion polypeptide, and the FGFR3-TACC3_v3 (N-FLAG) fusion polypeptide was examined using the above kinase activity detection kit and the same 384-well plate as above. 1.0 µL of solutions of the respective compounds were added to the wells such that the final concentration of the DMSO (as a solvent) became 0.1%, and the final concentration of the compound Dovitinib became 1 µM, 100 nM, and 10 nM; the final concentration of AZD4547 and BGJ398 became 100 nM, 10 nM, and 1 nM respectively; and the final concentration of LY2874455 became 10 nM, 1 nM, and 0.1 nM. Alternatively, as a control, only DMSO was added to the wells such that the concentration thereof became 0.1%. Moreover, for the FGFR3-TACC3_v1 (N-FLAG) fusion polypeptide 1 µL of a 2-fold diluted solution of the eluate was used; for the FGFR3-TACC3_v2 (N-FLAG) fusion polypeptide 1 µL of a 3-fold diluted solution of the eluate was used; and for the FGFR3-TACC3_v3 (N-FLAG) fusion polypeptide 1 µL of a 3-fold diluted solution of the eluate was used. Subsequently, as a substrate, TK Substrate included in the kit was added to the wells such that the final concentration thereof became 2.0 µM, and a reaction was performed for 15 minutes at room temperature. Thereafter, some of the wells were not supplemented with ATP while some of the wells supplemented with ATP such that the final concentration thereof became 100 µM, and a reaction was performed for 1 hour at room temperature by controlling the final volume to be 5.0 µL. In addition, each of the Sa-XL665 solution and the TK Antibody-EU (K) solution prepared in the same manner as in the above section (3) was added to the wells in an amount of 2.5 µL each, followed by incubation for 1 hour at room temperature, and the count of HTRF was detected. The counts of phosphorylation in the wells not supplemented with ATP and in the wells supplemented with ATP in the absence of the compound (in this case DMSO was added at a concentration of 0.1% same as the case of adding the compound) were regarded as having 100% inhibition and 0% inhibition respectively, and the inhibition rate (%) of the compounds against the kinase activity of the FGFR3-TACC3_v1 (N-FLAG) fusion polypeptide, the FGFR3-TACC3_v2 (N-FLAG) fusion polypeptide, and the FGFR3-TACC3_v3 (N-FLAG) fusion polypeptide was calculated by the following formula.

[Kinase activity inhibition rate of compound (%)]=
(1−[count of phosphorylation at the time when compound and ATP are added−count of phosphorylation at the time when neither compound nor ATP is added]/[count of phosphorylation at the time when ATP is added but compound is not added−count of phosphorylation at the time when neither compound nor ATP is added])× 100

As a result, it was found that the phosphorylation activity of the purified FGFR3-TACC3_v1 (N-FLAG) fusion polypeptide, FGFR3-TACC3_v2 (N-FLAG) fusion polypeptide, and FGFR3-TACC3_v3 (N-FLAG) fusion polypeptide to the peptide substrate was inhibited by the compounds Dovitinib, AZD4547, BGJ398, and LY2874455. The inhibition rates (%) of the respective compounds at the respective final concentrations against the peptide substrate are shown in Table 1.

TABLE 1

| Compound | Final concentration | Inhibition against peptide substrate FGFR3-TACC3 | | |
|---|---|---|---|---|
| | | v1 | v2 | v3 |
| Dovitinib | 1 µM | 94% | 94% | 93% |
| | 100 nM | 36% | 37% | 43% |
| | 10 nM | 15% | 9% | 7% |
| AZD4547 | 100 nM | 69% | 77% | 74% |
| | 10 nM | 46% | 50% | 52% |
| | 1 nM | 13% | 16% | 9% |
| BGJ398 | 100 nM | 58% | 79% | 75% |
| | 10 nM | 47% | 44% | 38% |
| | 1 nM | 26% | 8% | 13% |
| LY2874455 | 10 nM | 77% | 87% | 83% |
| | 1 nM | 46% | 64% | 57% |
| | 0.1 nM | 12% | 15% | 3% |

Example 22 Anchorage-Independent Cell Proliferation Inhibitory Activity of LY2874455 Against FGFR3-TACC3_v1 Expression/NIH3T3 Cells, FGFR3-TACC3_v2 Expression/NIH3T3 Cells, and FGFR3-TACC3_v3 Expression/NIH3T3 Cells The inhibitory activity against the proliferation of the FGFR3-TACC3_v1 expression/NIH3T3 cells, the FGFR3-TACC3_v2 expression/NIH3T3 cells, and the FGFR3-TACC3_v3 expression/NIH3T3 cells was evaluated in the same manner as in Example 9, except that the final concentration of LY2874455 was controlled to be 10 nM. As a result, the inhibition rate (%) of LY2874455 was confirmed to be 88%, 90%, and 89% respectively.

The above results show that LY2874455, which is FGFR3-TACC3 fusion polypeptide inhibitor, can inhibit the proliferation of cancer cells or tumors expressing FGFR3-TACC3_v1, FGFR3-TACC3_v2, and FGFR3-TACC3_v3.

Example 23 Isolation of FGFR3-TACC3_v5a and FGFR3-TACC3_v5b from a Specimen of Invasive Human Bladder Cancer A specimen of invasive human bladder cancer (Tissue Solutions UK) was reverse-transcribed into cDNA with a reverse transcriptase kit (Super Script III First Strand Synthesis Super Mix; Life Technologies Corporation) by using an oligo dT primer.

Next, PCR reaction (reaction condition: 94° C. for 2 minutes followed by 40 cycles of a reaction consisting of 98° C. for 10 seconds and 68° C. for 3.5 minutes) was performed using an FGFR3_F002 primer (SEQ ID NO: 23), a TACC3_R002 primer (SEQ ID NO: 24), the cDNA obtained as above as a template, and a DNA polymerase (PrimeSTAR; TAKARA BIO INC.).

These primers correspond to 5' UTR of the FGFR3 gene and 3' UTR of the TACC3 gene respectively. Accordingly, if a fusion gene composed of FGFR3 and TACC3 existed in a specimen, it would be possible to detect all fusion genes regardless of the variant.

The obtained PCR product was cloned into a cloning vector (Zero blunet TOPO PCR Kit; Life Technologies Corporation), and sequencing of an insert was performed by a dideoxy sequencing method (BigDye Terminator v3.1 Cycle Sequencing Kit; Life Technologies Corporation). As a result, it was clearly revealed that the PCR product was identical to a transcription product (FGFR3-TACC3_v5a) in which a sequence from 5' of CDS to the middle of exon 18 (from the $257^{th}$ base to the $2498^{th}$ base) of an FGFR3 gene registered in NCBI (NM_001163213.1) had been fused with the middle of exon 7 of CDS of a TACC3 gene (from the $1771^{st}$ base to the $2672^{nd}$ base of NM_006342.1), except for a single base (SEQ ID NO: 25). The position of the single base was the $1980^{th}$ base of an FGFR3 gene registered in NCBI (NM_001163213.1). Although the base had been registered as C, it was found to be G by sequencing. Furthermore, it was clearly revealed that there was also a transcription product (FGFR3-TACC3_v5b) (SEQ ID NO: 27) having a sequence from which a sequence (from the $690^{th}$ base to the $701^{st}$ base) of the 3' side of exon 4 of an FGFR3 gene (NM_001163213.1) had been deleted, and into which a CAG sequence had been inserted between exon 10 and exon 11. The polypeptide encoded by SEQ ID NO: 25 is shown in SEQ ID NO: 26, and the polypeptide encoded by SEQ ID NO: 27 is shown in SEQ ID NO: 28.

Example 24 Preparation of Retrovirus Solution of FGFR3-TACC3_v5a and FGFR3-TACC3_v5b In order to express a full length ORF of FGFR3-TACC3_v5a and FGFR3-TACC3_v5b as a protein, expression plasmids for preparing a retrovirus solution were established as below. 15 cycles of PCR reaction (reaction condition: 98° C. for 15 seconds, 55° C. for 15 seconds, and 68° C. for 3 minutes and 30 seconds) were performed using the cloned vectors prepared in Example 23 as templates respectively, primers of FGFR3_TACC3_cloning_BamHI_F represented by SEQ ID NO: 7 and FGFR3-TACC3_cloning_EcoRI F represented by SEQ ID NO: 8, and a DNA polymerase (KOD-plus-Ver. 2; TOYOBO CO., LTD.). After the PCR reaction, electrophoresis was performed, thereby obtaining PCR products having intended sizes respectively. The PCR products were cloned into a cloning vector (TOPO XL PCR Cloning Kit; Life Technologies Corporation), and sequencing of an insert was performed by a dideoxy sequencing method (BigDye Terminator v3.1 Cycle Sequencing Kit; Life Technologies Corporation). As a result, it was confirmed that each of the PCR products comprises SEQ ID NO: 25 or SEQ ID NO: 27. In order to express a full length ORF of FGFR3-TACC3_v5a and FGFR3-TACC3_v5b as a protein, a DNA fragment treated with a restriction enzyme which was obtained by subjecting the above cloning vector to an enzymatic reaction for 3 hours at 37° C. by using a restriction enzyme BamHI was purified, and a DNA fragment treated with a restriction enzyme which was obtained by subjecting the above cloning vector to an enzymatic reaction for 3 hours at 37° C. by using EcoRI was purified. The DNA fragments including ORF were cloned into position between a BamHI site and an EcoRI site present in a multicloning site of an expression vector (pMXs-puro; Cosmobio Co., Ltd.), thereby establishing expression plasmids (FGFR3-TACC3_v5a/pMXs-puro and FGFR3-TACC3_v5b/pMXs-puro).

By using the vectors established as above, retrovirus solutions were prepared according to the method of Example 7.

Example 25 Examination on Anchorage-Independent Proliferation-Accelerating Activity of FGFR3-TACC3_v5a and FGFR3-TACC3_v5b By using the virus solutions prepared in Example 24 with the FGFR3-TACC3_v5a/pMXs-puro and the FGFR3-TACC3_v5b/pMXs-puro, NIH3T3 cells stably expressing FGFR3-TACC3_v5a and FGFR3-TACC3_v5b were obtained according to the method of Example 8 (the cells were designated as FGFR3-TACC3_v5a expression/NIH3T3 cells and FGFR3-TACC3_v5b expression/NIH3T3 cells respectively).

In order to examine anchorage-independent proliferation-accelerating ability of the FGFR3-TACC3_v5a expression/NIH3T3 cells and the FGFR3-TACC3_v5b expression/NIH3T3 cells, the same method as in Example 8 was used. It was confirmed that while the cell count of the Mock/NIH3T3 cells did not increase from Day 1 to Day 4, the cell count of the FGFR3-TACC3_v5a expression/NIH3T3 cells increased by about 2.6-fold from Day 1 to Day 4. It was also confirmed that the cell count of the FGFR3-TACC3_v5b expression/NIH3T3 cells increased by about 2.7-fold from Day 1 to Day 4. These results clearly show that the FGFR3-TACC3_v5a expression/NIH3T3 cells and the FGFR3-TACC3_v5b expression/NIH3T3 cells exhibit anchorage-independent cell proliferation-accelerating activity.

Example 26 Detection of FGFR3-TACC3 Fusion Polypeptide in Formalin Fixed Sample of FGFR3-TACC3_v1 Expression/NIH3T3 Cells by Means of Immunostaining Method (1) Preparation of Sample The FGFR3-TACC3_v1 expression/NIH3T3 cells and the NIH3T3 cells prepared in Example 8 were cultured overnight on cover glass. On the next day, the culture medium was removed, and then the cells were fixed with 3.7% formaldehyde for 10 minutes at room temperature. After being washed with PBS, the cells were treated with 0.2% Triton X-100 (Nakalai Tesque) for 10 minutes at room temperature and then treated with 0.5% SDS for 25 minutes at room temperature. After being washed with PBS, the cells were blocked by a Blocking solution (Olink Bioscience).

(2) Detection of Target Fusion Polypeptide

The sample prepared in the section (1) was incubated at 4° C. overnight with FGFR3 antibodies (host: mouse, Santacruz Biotechnology, Inc.) and TACC3 antibodies (host: goat, R&D Systems) diluted with Can Get Signal immunostain Solution A (TOYOBO CO., LTD.).

On the next day, the sample was washed with Wash buffer A (Olink Bioscience). Thereafter, the cover glass was dipped in Duolink inSitu PLA probe anti-Mouse MINUS and Duolink InSitu PLA probe anti-Goat PLUS (all manufactured by Olink Bioscience) diluted with Can Get Signal immunostain Solution A for 1 hour at room temperature. After being washed with Wash buffer A, the sample was dipped in a Ligation-Ligase solution (Olink Bioscience) included in Duolink II reagent kit and incubated for 30 minutes at 37° C. By this step, a cyclic oligonucleotide is formed between two kinds of InSitu PLA probe antibodies present in positions sufficiently close to each other. After the sample was washed with Wash buffer A, an Amplification-Polymerase solution (Olink Bioscience) included in the same kit was added thereto, and the sample was incubated for 100 minutes at 37° C. By this step, a nucleic acid is elongated by using the cyclic oligonucleotide as a template, and a fluorescence-labeled oligonucleotide is hybridized with the elongated nucleic acid. After being washed twice with Wash buffer B (Olink Bioscience) and washed once with a solution obtained by diluting the Wash buffer B with water by 100-fold, the sample was encapsulated in Duolink Mounting Medium with DAPI (Olink Bioscience), and the fluorescence thereof was observed with a confocal laser microscope (LSM700; Carl Zeiss). In the FGFR3-TACC3_v1 expression/NIH3T3 cells, cells having a large number of fluorescent dots were observed. On the contrary, in the NIH3T3 cells, a fluorescent dot was practically not observed. The fluorescent dot results from the fluorescence-labeled oligonucleotide having been hybridized with the nucleic acid which has been elongated by using the cyclic oligonucleotide as a template, and is observed when two kind of antigens, that is, FGFR3 and TACC3 are in a state of being sufficiently close to each other, that is, in a state of existing in the same molecule. Accordingly, it was confirmed that by observing the existence of the fluorescent dot by means of the method of the present example, it is possible to decide (detect) the existence or absence of the FGFR3-TACC3 fusion polypeptide.

Example 27 Detection of FGFR3-TACC3 Fusion Polypeptide in Formalin Fixed Paraffin Embedded (FFPE) Sample of RT-112 Cells by Means of Immunostaining Method (1) Preparation of Sample FFPE samples of the RT-112 cells expressing FGFR3-TACC3_v1 and the HSC-39 cells not expressing FGFR3-TACC3_v1 which were prepared in Example 19 were dipped 3 times in each of xylene and ethanol respectively for 8 minutes so as to remove paraffin, and then the samples were dipped in Immunosaver (Nissin EM Corporation) and boiled. After being washed with PBS, the slices were treated with 0.2% Triton X-100 for 10 minutes at room temperature.

Thereafter, the slices were washed with PBS, and blocking was performed using Protein Block Serum-Free (Dako).

(2) Detection of Target Fusion Polypeptide

According to the same procedure as in the section (2) of Example 26, detection was performed by the immunostaining method, and the fluorescence of the sample was observed. In the RT-112 cells expressing FGFR3-TACC3_v1, a large number of fluorescent dots were observed. On the contrary, in the HSG-39 cells not expressing FGFR3-TACC3_v1, such fluorescent dots were practically not observed. Accordingly, it was confirmed that by observing fluorescent dots in an FFPE slice containing cells intrinsically expressing the FGFR3-TACC3 fusion gene, it is possible to decide (detect) the existence or absence of the FGFR3-TACC3 fusion polypeptide.

Example 28 Detection of FGFR3-TACC3 Fusion Polypeptide in FFPE Slices Derived from Patients with Bladder Cancer by Means of Immunostaining (1) Preparation of Sample FFPE slices of clinical specimens of bladder cancer which were purchased from Tissue Solutions UK were dipped 3 times in each of xylene and ethanol respectively for 8 minutes so as to remove paraffin, and then the slice was dipped in Immunosaver (Nissin EM Corporation) and boiled. The FFPE slices were washed with a Milli-Q solution and then incubated at room temperature for 30 minutes with 3% aqueous hydrogen peroxide. After being washed with PBS, the slices were treated with 0.2% Triton X-100 for 10 minutes at room temperature and then treated with a 0.5% SDS solution for 20 minutes. Thereafter, the slices were washed with PBS, and blocking was performed using Protein Block Serum-Free (Dako).

(2) Detection of Target Fusion Polypeptide

The FFPE slices were incubated overnight at 4° C. with FGFR3 antibodies (host: mouse, Santacruz Biotechnology, Inc.) and TACC3 antibodies (host: goat, R&D Systems) diluted with Can Get Signal immunostain Solution A (TOYOBO CO., LTD.).

On the next day, the slices were washed with Wash buffer A (Olink Bioscience). Thereafter, the FFPE slices were dipped in Duolink inSitu PLA probe anti-Mouse MINUS and Duolink InSitu PLA probe anti-Goat PLUS (all manufactured by Olink Bioscience) diluted with Can Get Signal immunostain Solution A for 1 hour at room temperature. After being washed with Wash buffer A, the slices were dipped in a Ligation-Ligase solution (Olink Bioscience) included in Duolink II Bright field reagent kit and incubated for 30 minutes at 37° C. By this step, the cyclic oligonucleotide is formed as in Examples 26 and 27. After being washed with Wash buffer A, the slices were incubated for 120 minutes at 37° C. in an Amplification-Polymerase solution (Olink Bioscience) included in the same kit. By this step, a nucleic acid is elongated by using the cyclic oligonucleotide as a template. After being washed with Wash buffer A, the slices were dipped in a Detection Bright Field solution included in the same kit for 1 hour at room temperature. By this step, an oligonucleotide labeled with Horseradish peroxidase (HRP) is hybridized with the nucleic acid elongated in the above step. After being washed with Wash buffer A, the slices were supplemented with a Substrate solution included in the same kit and reacted for 10 to 15 minutes at room temperature. Subsequently, after being washed with a Milli-Q solution, the slices were supplemented with a Nuclear stain solution included in the same kit, reacted for 2 minutes at room temperature, and washed with tap water. Thereafter, after being dehydrated and clarified by using ethanol and xylene, the slices were encapsulated.

As a result of performing brightfield observation by using a microscope (BZ-9000; KEYENCE Co., Ltd.), in the FFPE slice derived from tissues of patients with bladder cancer which were confirmed to express FGFR3-TACC3_v1 by the method of Example 23, portions stained red were observed. On the contrary, in the slice derived from tissues of patients which were confirmed not to express a fusion gene composed of FGFR3 and TACC3 by the method of Example 23, portions stained red were not observed. The portions stained red result from the HRP-labeled oligonucleotide hybridized with the nucleic acid which was elongated using the cyclic oligonucleotide as a template, and observed when FGFR3 and TACC3 exist in the same molecule as in Examples 26 and 27. Accordingly, it was confirmed that in the slice in which the portions stained red is observed, FGFR3 and TACC3 exist in a state of being fused with each other. Consequentially, it was confirmed that even in the FFPE slice derived from tissues of patients with bladder cancer, by observing portions stained red, it is possible to decide (detect) the existence or absence of the FGFR3-TACC3 fusion polypeptide.

Example 29 Inhibitory Activity of Compounds a, B, C, D, and E Against In Vitro Kinase Activity of FGFR3-TACC3 (N-FLAG) Fusion Polypeptide According to the method of the section (4) of Example 21, inhibitory activity of Compounds A, B, C, D, and E against in vitro kinase activity of the FGFR3-TACC3_v1 (N-FLAG) fusion polypeptide, the FGFR3-TACC3_v2 (N-FLAG) fusion polypeptide, and the FGFR3-TACC3_v3 (N-FLAG) fusion polypeptide was examined. Here, each of the compounds was added such that the final concentration thereof became 100 nM, 10 nM, and 1 nM.

As a result, it was found that the phosphorylation activity of the purified FGFR3-TACC3_v1 (N-FLAG) fusion polypeptide, FGFR3-TACC3_v2 (N-FLAG) fusion polypeptide, and FGFR3-TACC3_v3 (N-FLAG) fusion polypeptide with respect to a peptide substrate was inhibited by Compounds A, B, C, D, and E. The inhibition rate (%) of the respective compounds at the respective final concentrations against the peptide substrate is shown in Table 2.

TABLE 2

| Compound | Final concentration | Inhibition against peptide substrate FGFR3-TACC3 | | |
| --- | --- | --- | --- | --- |
| | | v1 | v2 | v3 |
| A | 100 nM | 92% | 94% | 93% |
| | 10 nM | 77% | 86% | 85% |
| | 1 nM | 49% | 33% | 47% |
| B | 100 nM | 92% | 94% | 96% |
| | 10 nM | 79% | 74% | 81% |
| | 1 nM | 28% | 24% | 35% |
| C | 100 nM | 95% | 95% | 96% |
| | 10 nM | 79% | 73% | 86% |
| | 1 nM | 31% | 22% | 41% |
| D | 100 nM | 94% | 95% | 97% |
| | 10 nM | 80% | 80% | 85% |
| | 1 nM | 34% | 27% | 45% |
| E | 100 nM | 86% | 78% | 91% |
| | 10 nM | 40% | 25% | 55% |
| | 1 nM | 7% | 6% | 30% |

Example 30 Anchorage-Independent Cell Proliferation Inhibitory Activity of Compounds a, B, C, D, and E Against FGFR3-TACC3_v1 Expression/NIH3T3 Cells, FGFR3-TACC3_v2 Expression/NIH3T3 Cells, FGFR3-TACC3_v3 Expression/NIH3T3 Cells, and RT-112 Cell Lines Derived from a Patient with Bladder Cancer The FGFR3-TACC3_v1 expression/NIH3T3 cells, the FGFR3-TACC3_v2 expression/NIH3T3 cells, and the FGFR3-TACC3_v3 expression/NIH3T3 cells were seeded using the same medium as in Example 9. The RT-112 cell line derived from a patient with bladder cancer was seeded using an RPMI1640 medium containing 10% fetal bovine serum and 2 mM L-glutamine, such that the cell count per well became 1×10³. Moreover, the respective compounds were added such that the final concentration thereof became 100 nM, 10 nM, and 1 nM. Conditions other than these were set to be the same as in the method of Example 9, and the inhibitory activity of Compounds A, B, C, D, and E against the proliferation of the FGFR3-TACC3_v1 expression/NIH3T3 cells, the FGFR3-TACC3_v2 expression/NIH3T3 cells, the FGFR3-TACC3_v3 expression/NIH3T3 cells, and RT-112 cell line derived from a patient with bladder cancer was evaluated. As a result, it was found that the anchorage-independent proliferation-accelerating activity of the FGFR3-TACC3_v1 expression/NIH3T3 cells, the FGFR3-TACC3_v2 expression/NIH3T3 cells, the FGFR3-TACC3_v3 expression/NIH3T3 cells, and RT-112 cell line derived from a patient with bladder cancer was inhibited by Compounds A, B, C, D, and E. The inhibition rate (%) of the respective compounds at the respective final concentrations against the cell growth is shown in Table 3.

The above result clearly shows that the proliferation of cancer cells or tumors expressing FGFR3-TACC3_v1, FGFR3-TACC3_v2, and FGFR3-TACC3_v3 can be inhibited by Compounds A, B, C, D, E, and F.

TABLE 3

| Ex | | v1 | v2 | v3 | RT-112 |
|---|---|---|---|---|---|
| A | 100 nM | 92% | 91% | 91% | 90% |
|   | 10 nM  | 84% | 79% | 78% | 83% |
|   | 1 nM   | 22% | 21% | 20% | 29% |

TABLE 3-continued

| Ex | | v1 | v2 | v3 | RT-112 |
|---|---|---|---|---|---|
| B | 100 nM | 91% | 91% | 87% | 89% |
|   | 10 nM  | 53% | 42% | 32% | 77% |
|   | 1 nM   | 4%  | 2%  | 3%  | 23% |
| C | 100 nM | 91% | 90% | 86% | 89% |
|   | 10 nM  | 44% | 31% | 24% | 72% |
|   | 1 nM   | 5%  | 0%  | 3%  | 21% |
| D | 100 nM | 90% | 88% | 89% | 89% |
|   | 10 nM  | 84% | 79% | 79% | 80% |
|   | 1 nM   | 26% | 23% | 25% | 23% |
| E | 100 nM | 84% | 79% | 81% | 81% |
|   | 10 nM  | 28% | 29% | 20% | 33% |
|   | 1 nM   | 7%  | 11% | 6%  | 5%  |

INDUSTRIAL APPLICABILITY

The detection method of the present invention can be used for determining a patient positive for either the fusion gene of the present specification or the polypeptide of the present invention. Moreover, the detection kit, the primer set, and the probe set of the present invention can be used for the detection method. Furthermore, a substance inhibiting the polypeptide of the present invention can be used as a pharmaceutical composition for treating cancer (particularly, lung cancer or bladder cancer) which is positive for either a fusion gene composed of an FGFR3 gene and a TACC3 gene or the polypeptide of the present invention.

FREE TEXT OF SEQUENCE LISTING

The section titled with number <223> in the following sequence listing includes a description of "Artificial Sequence". In particular, each of the nucleotide sequences represented by SEQ ID NO:13, SEQ ID NO: 14, and SEQ ID NO: 21 of the sequence listing is an artificially synthesized primer sequence. The nucleotide sequence represented by SEQ ID NO: 22 of the sequence listing is an artificially synthesized FLAG tag sequence.

The invention claimed is:

1. A method for treating cancer which is positive for either a fusion gene composed of a portion of a fibroblast growth factor receptor 3 (FGFR3) gene and a portion of a transforming acidic coiled-coil containing protein 3 (TACC3) gene (FGFR3/TACC3 fusion gene) or a fusion protein composed of a portion of a FGFR3 protein and a portion of a TACC3 protein (FGFR3/TACC3 fusion protein), comprising administering to a subject an effective amount of a substance that inhibits the FGFR3/TACC3 fusion protein, wherein the FGFR3/TACC3 fusion protein has tumorigenicity and comprises an amino acid sequence having 90% or more identity to the amino acid sequence represented by amino acid numbers 461 to 947 of SEQ ID NO: 2, amino acid numbers 461 to 982 of SEQ ID NO: 4, or amino acid numbers 461 to 996 of SEQ ID NO: 6, wherein the FGFR3/TACC3 gene encodes the FGFR3/TACC protein, and wherein the substance is a low-molecular weight compound having inhibitory activity against FGFR3.

2. The method of claim 1, wherein the FGFR3/TACC3 fusion protein comprises an amino acid sequence selected from the group consisting of the amino acid sequence represented by amino acid numbers 461 to 947 of SEQ ID NO: 2, the amino acid sequence represented by amino acid numbers 461 to 982 of SEQ ID NO: 4, the amino acid sequence represented by amino acid numbers 461 to 996 of SEQ ID NO: 6, an amino acid sequence having a deletion, substitution, and/or insertion of 1 to 10 amino acids in amino acid numbers 461 to 947 of SEQ ID NO: 2, an amino acid sequence having a deletion, substitution and/or insertion of 1 to 10 amino acids in amino acid numbers 461 to 982 of SEQ ID NO: 4, and an amino acid sequence having a deletion, substitution and/or insertion of 1 to 10 amino acids in amino acid numbers 461 to 996 of SEQ ID NO: 6.

3. The method of claim 1, wherein the FGFR3/TACC3 fusion protein consists of an amino acid sequence represented by amino acid numbers 461 to 947 of SEQ ID NO: 2, amino acid numbers 461 to 982 of SEQ ID NO: 4, or amino acid numbers 461 to 996 of SEQ ID NO: 6.

4. A method for treating cancer which is positive for either a FGFR3/TACC3 fusion gene or a FGFR3/TACC3 fusion protein, comprising administering to a subject an effective amount of a substance that inhibits the FGFR3/TACC3 fusion protein, wherein the FGFR3/TACC3 fusion protein has tumorigenicity and comprises an amino acid sequence having 90% or more identity to SEQ ID NO: 2; an amino acid sequence having 90% or more identity to SEQ ID NO: 4; or an amino acid sequence having 90% or more identity to SEQ ID NO: 6, wherein the FGFR3/TACC3 gene encodes the FGFR3/TACC protein, and wherein the substance is a low-molecular weight compound having inhibitory activity against FGFR3.

5. The method of claim 4, wherein the FGFR3/TACC3 fusion protein comprises an amino acid sequence selected from the group consisting of the amino acid sequence represented by SEQ ID NO: 2, the amino acid sequence represented by SEQ ID NO: 4, the amino acid sequence represented by SEQ ID NO: 6, an amino acid sequence having deletion, substitution, and/or insertion of 1 to 10 amino acids in the amino acid sequence represented by SEQ ID NO: 2, an amino acid sequence having deletion, substitution, and/or insertion of 1 to 10 amino acids in the amino acid sequence represented by SEQ ID NO: 4, and an amino acid sequence having deletion, substitution, and/or insertion of 1 to 10 amino acids in the amino acid sequence represented by SEQ ID NO: 6.

6. The method of claim 4, wherein the FGFR3/TACC3 fusion protein consists of the amino acid sequence represented by SEQ ID NO: 2, SEQ ID NO: 4, or SEQ ID NO: 6.

7. The method of claim 1, wherein the substance is selected from among dovitinib, AZD4547, BGJ398, and LY2874455.

8. The method of claim 4, wherein the substance is selected from among dovitinib, AZD4547, BGJ398, and LY2874455.

9. The method of claim 1, wherein the cancer is lung cancer or bladder cancer.

10. The method of claim 4, wherein the cancer is lung cancer or bladder cancer.

\* \* \* \* \*